(12) United States Patent
Felsher et al.

(10) Patent No.: US 10,894,988 B2
(45) Date of Patent: Jan. 19, 2021

(54) METHOD OF DETERMINING THE PROGNOSIS OF HEPATOCELLULAR CARCINOMAS USING A MULTIGENE SIGNATURE ASSOCIATED WITH METASTASIS

(71) Applicant: The Board of Trustees of the Leland Stanford Junior University, Palo Alto, CA (US)

(72) Inventors: Dean Felsher, San Mateo, CA (US); Meital Ryan, Mountain View, CA (US); Robert Tibshirani, Palo Alto, CA (US)

(73) Assignee: THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 193 days.

(21) Appl. No.: 15/758,544

(22) PCT Filed: Sep. 9, 2016

(86) PCT No.: PCT/US2016/050880
§ 371 (c)(1),
(2) Date: Mar. 8, 2018

(87) PCT Pub. No.: WO2017/044694
PCT Pub. Date: Mar. 16, 2017

(65) Prior Publication Data
US 2019/0040469 A1 Feb. 7, 2019

Related U.S. Application Data

(60) Provisional application No. 62/292,485, filed on Feb. 8, 2016, provisional application No. 62/217,181, filed on Sep. 11, 2015.

(51) Int. Cl.
*C12Q 1/68* (2018.01)
*C12Q 1/6886* (2018.01)

(52) U.S. Cl.
CPC ..... *C12Q 1/6886* (2013.01); *C12Q 2600/158* (2013.01)

(58) Field of Classification Search
None
See application file for complete search history.

(56) References Cited

U.S. PATENT DOCUMENTS

| | | |
|---|---|---|
| 2005/0271654 A1 | 12/2005 | Webb |
| 2014/0121130 A1 | 5/2014 | Felsher et al. |
| 2015/0147761 A1 | 5/2015 | Meyer et al. |

OTHER PUBLICATIONS

Cajusot et al. "Exome sequencing reveals frequent inactivating mutations in ARID1A, ARID1B, ARID2 and ARI04A in microsatellile unstable colorectal cancer." International journal of cancer 135.3 (2014): 61 1-623.

Hadley et al. "Structure and function of nucleotide sugar transporters: current progress." Computational and structural biotechnology journal 10.16 (2014): 23-32.

GenBank Accession No. EF036497 Homo sapiens aldolase A mRNA, partial cds. (Apr. 3, 2007) [found online Feb. 2, 2017 at https:/twww.ncbi.nlm.nih.gov/nuccore/134254705?sat=4&satkey=16846972].

GenBank Accession No. AY888707 Synthetic construct Homo sapiens clone FLH023719.01X lectin galactoside-binding soluble 1 (LGALSI) mRNA, complete cds (Mar. 29, 2005) [found online Feb. 2, 2017 at https://www.ncbi.nlm.nih.govlnuccoreiAY888707].

GenBank Accession No. M60278 Human heparin-binding EGF-like growth factor mRNA, complete cds, HUMHBEGF (Apr. 27, 1993) [found online Feb. 2, 2017 at https://www.ncbi.nlm.nih.gov/nuccore/M60278].

GenBank Accession No. M16110 Homo sapiens alpha-fetoprotein gene, complete cds, HUMAFP (Oct. 16, 2008) [found online Feb. 2, 2017 at https://www.ncbi .nlm.nih.gov/nuccore/M16110].

GenBank Accession No. CU693307 Synthetic construct Homo sapiens gateway clone Image:100017429 3' read AFP mRNA. (Feb. 23, 2008) [found online Feb. 2, 2017 at https://www.ncbi.nlm.nih.gov/nuccore/CU693307].

GenBank Accession No. KJ893212 Synthetic construct Homo sapiens clone ccsbBroadEn_02606 SLC35D2 gene, encodes complete protein. (Mar. 19, 2015) (found online Feb. 2, 2017 at https://www.ncbi.nlm.nih.gov/nuccore/KJ893212].

GenBank Accession No. M61855 Human cytochrome P4502C9 (CYP2C9) mRNA, clone 25 (Dec. 31, 1994) [found online Feb. 2, 2017 at https://www.ncbi.nlm.nih.gov/nuccore/M61855].

GenBank Accession No. KJ900586 Synthetic construct Homo sapiens clone ccsbBroadEn_09980 CYP4V2 gene, encodes complete protein. (Mar. 19, 2015) [found online Feb. 2, 2017 at https://www.ncbi.nlm.nih.gov/nuccore/KJ900586].

GenBank Accession No. AB451269 Homo sapiens LIMK2 mRNA for LIM domain kinase 2 isoform 2a, complete cds, clone: FLJ08094AAAN. (Sep. 2, 2008) [found online Feb. 2, 2017 at https://www.ncbi.nlm.nih.gov/nuccore/A6451269].

GenBank Accession No. AK299382 Homo sapiens eDNA FLJ51058 complete cds, highly similar to Lysosomal acid phosphatase precursor (EC 3.1.3.2). (Jan. 21, 2009) (found online Feb. 2, 2017 at https://www.ncbi.nlm.nih.gov/nuccore/AK299382].

GenBank Accession No. M64303 Human galactoside-binding protein mRNA. (Nov. 3, 1993) [found online Feb. 2, 2017 at https://www.ncbi.nlm.nih.gov/nuccore/M64303].

GenBank Accession No. CU678421 Synthetic construct Homo sapiens gateway clone Image:100017172 3' read NDRG1 mRNA. (Feb. 19, 2008) [found online Feb. 2, 2017 at https://www.ncbi.nlm.nih.gov/nuccore/CU678421].

*Primary Examiner* — Jehanne S Sitton
(74) *Attorney, Agent, or Firm* — Thomas | Horstemeyer, LLP

(57) ABSTRACT

Through genomic analysis a 12-gene signature comprising up-regulated genes and down-regulated genes has been identified that is highly predictive of metastasis and overall survival in human patients with HCC. Another aspect of the disclosure methods of determining the metastatic status of an hepatocellular carcinoma of a patient, comprising obtaining a first differential gene expression profile from a carcinoma sample from a subject having an hepatocellular carcinoma and creating a report summarizing the normalized data obtained by the first gene expression analysis and including a determination of the metastatic status of the hepatic carcinoma.

12 Claims, 39 Drawing Sheets

Specification includes a Sequence Listing.

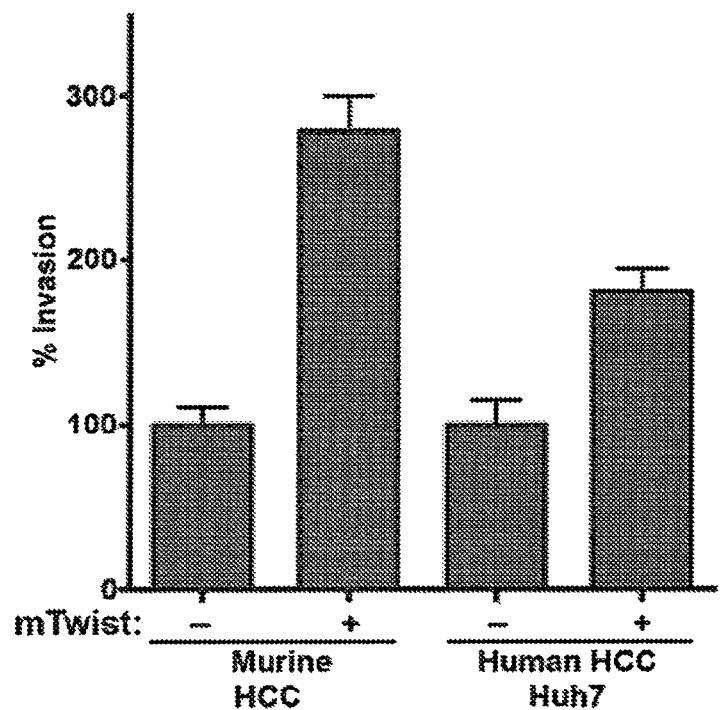
Fig. 14
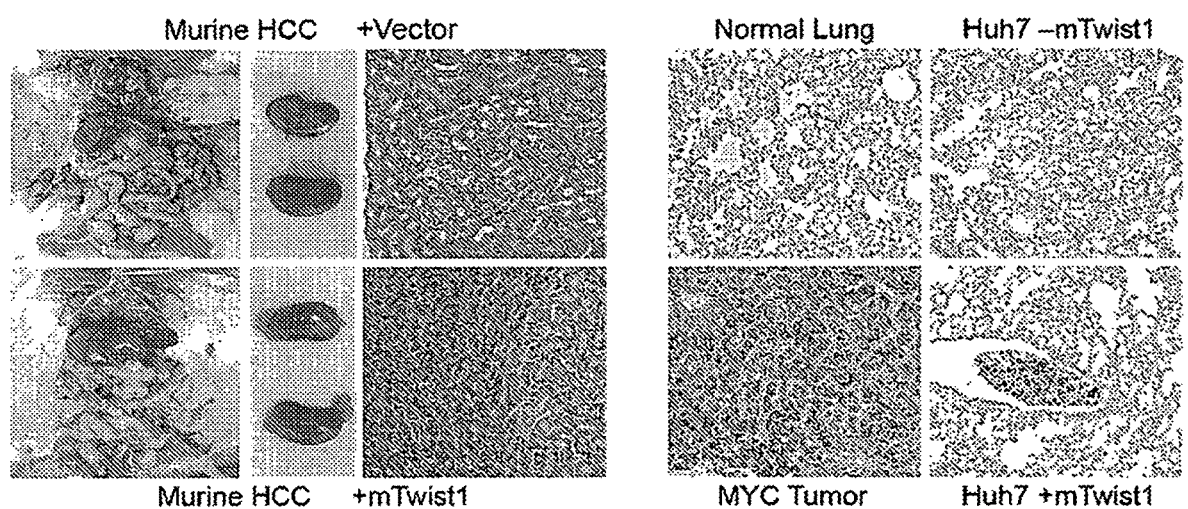
Fig. 15
Fig. 16

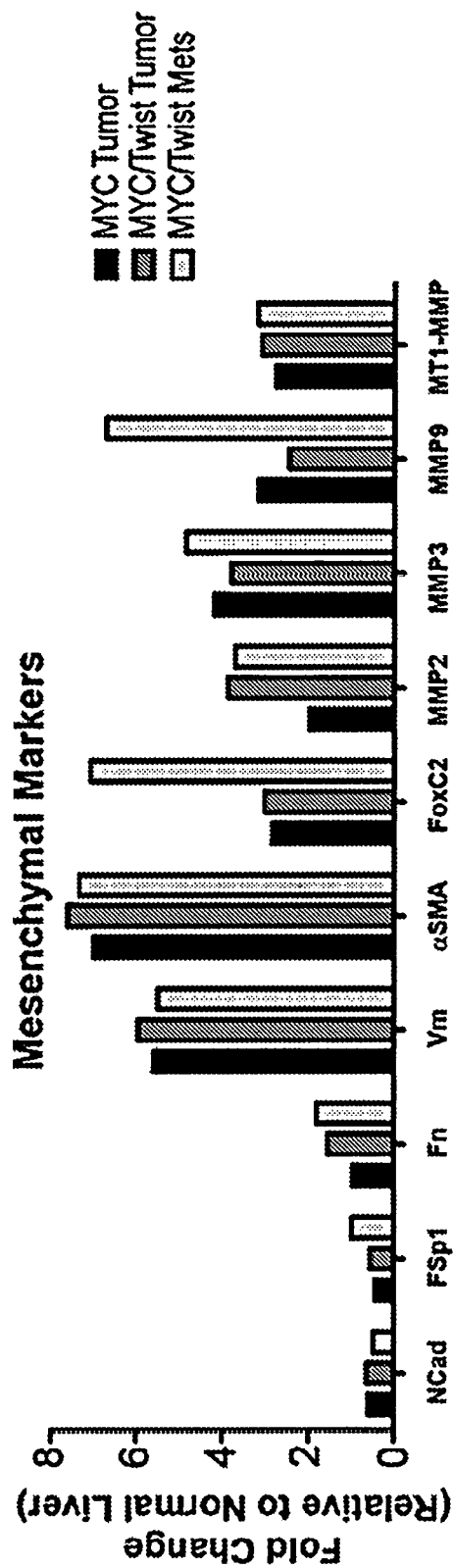
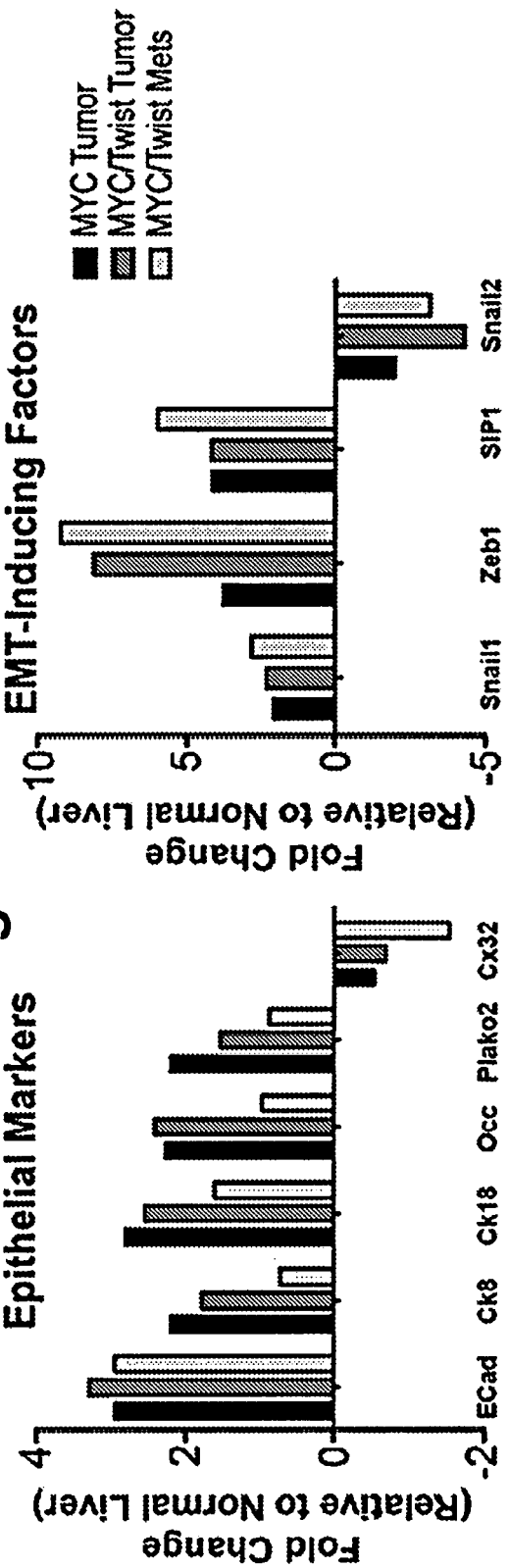
Fig. 17A
Fig. 17B
Fig. 17C

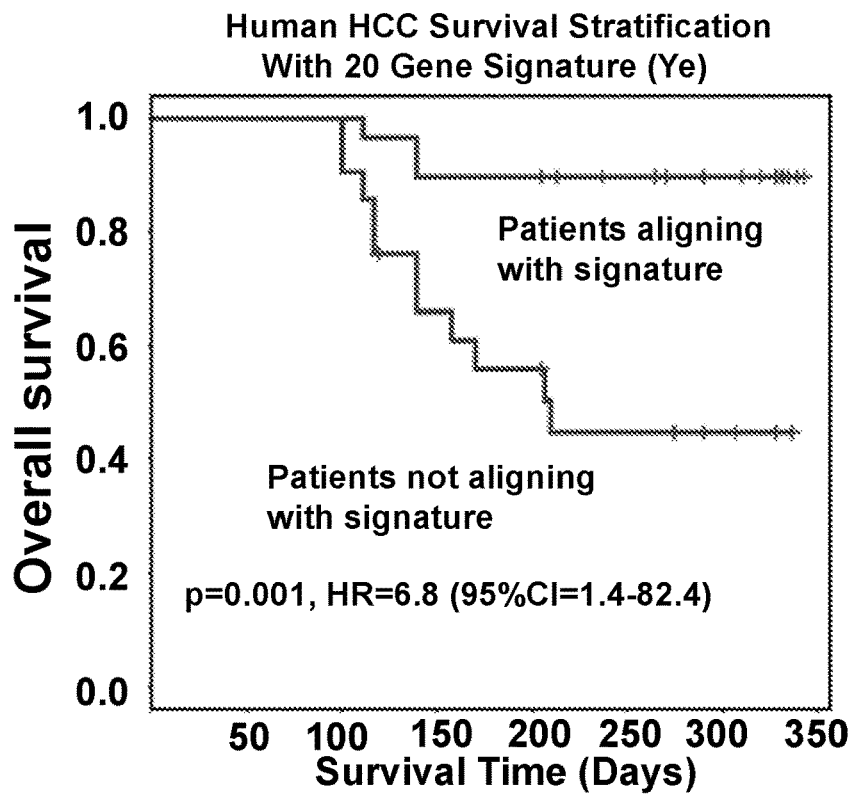
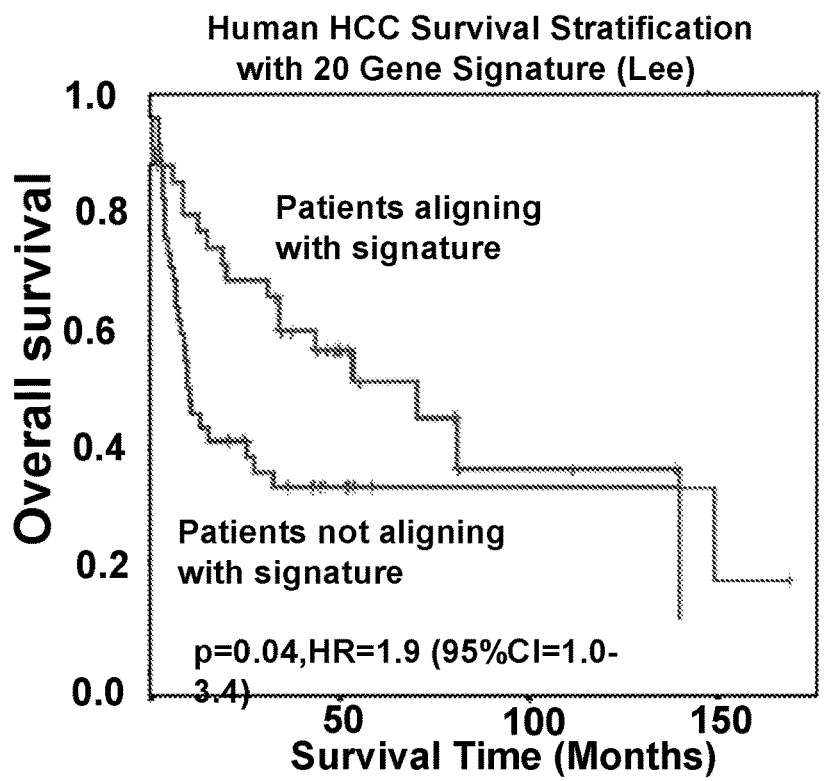
Fig. 24A

| Target Gene | SEQ ID NO | Forward Primer | SEQ ID NO | Reverse Primer | SEQ ID NO | Reporter-probe-quencher |
|---|---|---|---|---|---|---|
| ALDOA | 1 | AAGCGCTGCCAGTATGTGA | 2 | GTCACTCAGAGCCTTGTAGACA | 25 | CAGCCAGCACCTTCTC |
| ARID3A | 3 | GCTGCCCATGAGCATTCG | 4 | CGTCAGGTTCACAGCAGAGT | 26 | CCAAGCCTCCGAAAGC |
| LGALS1 | 5 | GAGGCTGTCTTTCCCTTCCA | 6 | GCAGCTTGACGGTCAGGTT | 27 | CAGAGGTGTGCATCACC |
| HBEGF | 7 | CCATGAGAATGCAAATATGTGAAGGA | 8 | TCAGCCCATGACACACCTCT | 28 | CCTGCATCTGCCACCC |
| HAFP | 9 | GCCAACTCAGTGAGGACAAACTATT | 10 | GGTTTACTGGAGTCATTTCATGTCTGA | 29 | AATGTCAGCCGCTCCC |
| SLC35D2 | 11 | TCCTCATCGTGCTTGTCAACAA | 12 | GCCATCTGTCCAATTCCAAGGAAA | 30 | CACCTACGGTTTCCC |
| CYP2C9 | 13 | CCATGCAGTGACCTGTGACATTAAA | 14 | ATGTAGCACAGAAGTCAGGAAATT | 31 | TCCCAAGGCACAACC |
| CYP4V2 | 15 | TGTTCCTTTATTTGCCCGTAGTGTT | 16 | CGGCTTCAGTGCCTTTTAGAACT | 32 | CTGTAACCTGCCACTTCAC |
| LIMK2 | 17 | GTGCTCCCTGCTGATGACA | 18 | CACTCTGGGTGGTACTTGAACTC | 33 | CCAGCCACCATAAAAG |
| ACP2 | 19 | CTGGAGACCGTCTGGAATGTC | 20 | GAGACGCTGCATGGTTTGG | 34 | CCGTGCGTTTGCTCAC |
| LGALS3 | 21 | GCCTCGCATGCTGATAACAATTC | 22 | GGCAACATCATTCCCTCTTTGA | 35 | AATGCAAACAGAATTGC |
| NDRG1 | 23 | GGACCCAACAAAGACCACTCT | 24 | GCCGGCTGGGAGATCTG | 36 | ACAGTCCGCCATCTTG |
| SCCPDH | 37 | GCAGCCATGACTCTTCTAAGTGAT | 38 | AGCTGCTCCAGGTGTGAAG | 65 | CCCCGCCCGCCTTA |
| KIFC1 | 39 | AGAAGCCAGTTCCTCCTGCTT | 40 | CCTGCCATGGGAGGAACAC | 66 | CTGATGTGCCAGACTTC |
| HMYC | 41 | CCCCTGGTCTGCTCCATGAG | 42 | CCTCTTTTCCACAGAAACAACATCGA | 67 | CCTCCTCCAGAGTCGCTG |
| HLPL | 43 | GCACACCAAGATACCATTCATCAAC | 44 | GGTAGAGATTGCCGCTATGAG | 68 | CCCTGGAGTGATTTC |
| IQGAP1 | 45 | CCCAAAGAACAAATACCAGGAACTG | 46 | CGGTACCTCCGCTGATTCC | 69 | ATTGCCAGGGATATTC |
| TBC1D1 | 47 | CAGCAGCATGCGATTCTTATTGAC | 48 | GGCAGAGAAGTATGGGTGTGTAG | 70 | CTTGGGCGAACCTTTC |
| TWIST1 | 49 | AGCGCGGCAAGAAGTCT | 50 | CGCACGTTGGCCATGAC | 71 | CAGCTCCTCGTAAGACTG |
| UAP1L1 | 51 | CAGCGACCCCGAGACA | 52 | CGGCCACCTTGTTCAGAGAA | 72 | TCTGACGGAAACCTTC |
| ENO2 | 53 | CGCGCCAGCCCTCAT | 54 | CAGGTTGTCCAGTTTCTCTTGCT | 73 | CAGCTCAGTCTCTCTG |
| MAP3K6 | 57 | GCTGCCCATGAGCATTCG | 56 | CGTCAGGTTCACAGCAGAGT | 74 | CCAAGCCTCCGAAAGC |
| PLP2 | 59 | GCACACCAAGATACCATTCATCAAC | 58 | GGTAGAGGATTGCCGCTATGAG | 75 | CCCTGGAGTGATTTC |
| PYGB | 61 | TGGAGAACTACCGTGTGTCCTT | 60 | TGCCTGCAGTGGAGATCTG | 76 | CCGGGATCACTTTCTC |
| HUBC | 63 | AAGGCAAAGATCCAAGACAAGGAA | 62 | CAGCTGTTTTCCGGCAAAGATC | 77 | CTGACCAGCAGAGGTT |
| CORO1C | 65 | TGTTCCTTTATTTGCCCGTAGTGTT | 64 | CGGCTTCAGTGCCTTTTAGAACT | 78 | CTGTAACCTGCCACTTCAC |

Fig 30

METHOD OF DETERMINING THE PROGNOSIS OF HEPATOCELLULAR CARCINOMAS USING A MULTIGENE SIGNATURE ASSOCIATED WITH METASTASIS

CROSS-REFERENCE TO RELATED APPLICATION

This application is the 35 U.S.C. § 371 national stage application of PCT Application No. PCT/US2016/050880, filed Sep. 9, 2016, where the PCT claims priority to and benefit of U.S. Provisional Application 62/217,181 titled "A METHOD OF DETERMINING THE PROGNOSIS OF HEPATOCELLULAR CARCINOMAS USING A MULTI-GENE SIGNATURE ASSOCIATED WITH METASTASIS" filed Sep. 11, 2015 and to U.S. Provisional Application 62/292,485 titled "A METHOD OF DETERMINING THE PROGNOSIS OF HEPATOCELLULAR CARCINOMAS USING A MULTIGENE SIGNATURE ASSOCIATED WITH METASTASIS" filed Feb. 8, 2016, the entire disclosures of which are incorporated herein by reference.

STATEMENT ON FUNDING PROVIDED BY THE U.S. GOVERNMENT

This invention was made with Government support under contracts CA184384 and TR001085 awarded by the National Institutes of Health. The Government has certain rights in the invention.

SEQUENCE LISTING

This application contains a sequence listing filed in electronic form as an ASCII.txt file entitled "2219072400_ST25" created on Sep. 6, 2016. The content of the sequence listing is incorporated herein in its entirety.

TECHNICAL FIELD

The present disclosure is generally related to a gene signature predictive of the outcome of a hepatocellular carcinoma, and to methods of identifying predictive members of the gene signature. The present disclosure is also related to identifying a target gene associated with regression of a metastatic hepatocellular carcinoma

BACKGROUND

Hepatocellular carcinoma (HCC) is a major global cancer health problem (Jemal et al., (2010) *CA Cancer J. Clin.* 60: 277-300; Altekruse et al., *J. Clin. Oncol.* 27:1485-1491), HCC has a dismal prognosis because it is usually diagnosed after widespread local invasion and/or distant metastasis (Sherman, M. (2008) *New Engl. J. Med.* 359: 2045-2047; Tang, Z. Y. (2001) *World J. Gastroenterol.* 7: 445-454). Methods that identify mechanisms and/or predict invasiveness of HCC would be of substantial clinical importance (Bruix & Sherman (2005) *Hepatology* 42: 1208-1236). Prior reports have identified gene signatures that are correlated with metastasis and invasion in HCC (Coulouarn et al., (2009) *Oncogene* 28, 3526-3536; Coulouarn et al., (2008) *Hepatology* 47: 2059-2067; Kaposi-Novak et al., (2006) *J. Clin. Invest.* 116: 1582-1595; Roessler et al., *Cancer Res.* 70, 10202-10212; Ye et al., (2003) *Nat. Med.* 9: 416-423) as well as in other cancer types (Barrier et al., (2006) *J. Clin. Onc.* 24: 4685-4691; Bos et al., (2009) *Nature* 459: 1005-1009; Bueno-de-Mesquita et al., (2007) *Lancet Oncol.* 8: 1079-1087; Kang et al., (2003) *Cancer Cell* 3: 537-549; Paik et al., (2004) *New Engl. J. Med.* 351: 2817-2826; Salazar et al., (2011) *J. Clin. Oncol.* 29: 17-24; Wan et al., (2005) *PLoS One* 5, e12222). Twist1 expression has been correlated with metastasis in multiple tumor types, including human HCC2-8 (Zhu et al., (2008) *J. Huazhong Univ. Sci. Technolog. Med. Sci.* 28: 144-146).

Twist1 is a member of a family of basic helix-loop-helix transcription factors that are associated with epithelial-mesenchymal transition (EMT), a process by which epithelial cells transdifferentiate into a more invasive phenotype. In human HCC, Twist1 expression has been correlated with advanced clinical stage of disease and poor prognosis (Lee et al., (2006) *Clin. Cancer Res.* 12: 5369-5376; Niu et al., (2007) *J. Exp. Clin. Cancer Res.* 26: 385-394; Sun et al., *Hepatology* 51: 545-556; Yang et al., (2009) *Hepatology* 50: 1464-1474; Ye et al., (2003) *Nat. Med.* 9: 416-423), as well as shown to induce increased invasion in tumor-derived cell lines in vitro (Lee et al., (2006) *Clin. Cancer Res.* 12: 5369-5376; Matsuo et al., (2009) *BMC Cancer* 9: 240; Sun et al., *Hepatology* 51: 545-556; Yang et al., (2009) *Hepatology* 50: 1464-1474; Zhao et al., *J. Cell Mol. Med.* 15: 691-700). However, a causal role for Twist1 in invasion and metastasis has yet to be demonstrated in vivo in any autochthonous tumor model.

SUMMARY

Gene expression profiling showed that the mouse model of HCC was representative of human disease. Through genomic analysis, a 12-gene signature comprising up-regulated genes and down-regulated genes has been identified that is highly predictive of metastasis and overall survival in human patients with HCC.

One aspect of the disclosure encompasses embodiments of a method for determining whether a hepatocellular carcinoma tissue of a patient has a differential gene expression signature of a metastatic hepatocellular carcinoma tissue, the method comprising the steps: (a) obtaining a first gene expression signature from a first tissue sample from a first subject by determining the levels of expression of the genes aldoa, arid3a, lgals1, hbegf, afp, slc35d2, cyp2c9, cyp4v2, limk2, acp2, lgals3, and ndrg1 in the first tissue sample, wherein the first tissue sample is a hepatocellular carcinoma; (b) obtaining a gene expression signature from a second tissue sample from a second subject by determining the levels of expression of the genes aldoa, arid3a, lgals1, hbegf, afp, slc35d2, cyp2c9, cyp4v2, limk2, acp2, lgals3, and ndrg1 in the second tissue sample, wherein the second tissue sample is from a subject not having an hepatocellular carcinoma or suspected of not having developed a metastatic hepatocellular carcinoma; wherein step (a) and step (b) each independently consists of the steps: (i) isolating RNA from the tissue sample and generating cDNA copies therefrom; (ii) quantitatively measuring the RNA levels expressed by the genes aldoa, arid3a, lgals1, hbegf, afp, slc35d2, cyp2c9, cyp4v2, limk2, acp2, lgals3, and ndrg1 by a Reverse Transcription Polymerase Chain Reaction (RT-PCR) assay, wherein the RT-PCR uses the PCR primer pairs: aldoa-specific SEQ ID NOs: 1 and 2; arid3a-specific SEQ ID NOs: 3 and 4; lgals1-specific SEQ ID NOs: 5 and 6; hbegf-specific SEQ ID NOs: 7 and 8; afp-specific SEQ ID NOs: 9 and 10; slc35d2-specific SEQ ID NOs: 11 and 12; cyp2c9-specific SEQ ID NOs: 13 and 14; cyp4v2-specific SEQ ID NOs: 15 and 16; limk2-specific SEQ ID NOs: 17 and 18; acp2-specific SEQ ID NOs: 19 and 20; lgals3-specific SEQ ID NOs: 21 and 22; and ndrg1-specific SEQ ID NOs: 23 and 24; and further uses the chemically-modified probes: aldoa-specific SEQ ID NO: 25; arid3a-specific SEQ ID NO: 26; lgals1-specific SEQ ID NO: 27; hbegf-specific SEQ ID NO: 28; afp-specific SEQ ID NO: 29; slc35d2-specific SEQ ID NO: 30; cyp2c9-specific SEQ ID NO: 31; cyp4v2-specific SEQ ID NO: 32; limk2-specific SEQ ID NO: 33; acp2-specific SEQ ID NO: 34; lgals3-specific SEQ ID NO: 35; and ndrg1-specific SEQ ID NO: 36, wherein each of the chemically-modified probes has a terminally attached fluorescent moiety and a terminally attached quenching moiety, and wherein the expression level of each gene is quantifiably measured by measuring the intensity of fluorescence from each of said gene-specific chemically-modified probes.

In some embodiments of this aspect of the disclosure, the method can further comprise the steps of: (c) comparing the levels of gene expression of the first and the second gene expression signatures, wherein the relative levels of gene expression indicate the presence or absence of metastatic hepatocellular carcinoma cells in the first subject suspected of having a metastatic hepatocellular carcinoma; and (d) generating a report indicating the metastatic status of a hepatocellular carcinoma of the patient, wherein: (i) if the expression of the genes aldoa, arid3a, lgals1, hbegf, afp, slc35d2 of the first tissue sample is elevated compared to the expression level of the same genes of the second tissue sample, there is a reduced likelihood of survival of the first subject development from the carcinoma in the patient; and (ii) if the expression of the genes cyp2c9, cyp4v2, limk2, acp2, lgals3, and ndrg1 in the first tissue sample is elevated compared to the expression level of the same genes of the second tissue sample, said levels indicate an extended period of the first subject survival.

In some embodiments of this aspect of the disclosure, the first and the second tissue samples are from the same subject and isolated therefrom at successive time-points.

Another aspect of the disclosure encompasses embodiments of a method of determining a mode of treatment of a hepatocellular carcinoma of a patient, comprising: (a) obtaining a first gene expression signature from a first tissue sample from a first subject by determining the levels of expression of the genes aldoa, arid3a, lgals1, hbegf, afp, slc35d2, cyp2c9, cyp4v2, limk2, acp2, lgals3, and ndrg1 in the first tissue sample, wherein the first tissue sample is a hepatocellular carcinoma; (b) obtaining a gene expression signature from a second tissue sample from a second subject by determining the levels of expression of the genes aldoa, arid3a, lgals1, hbegf, afp, slc35d2, cyp2c9, cyp4v2, limk2, acp2, lgals3, and ndrg1 in the second tissue sample, wherein the second tissue sample is from a subject not having an hepatocellular carcinoma or suspected of not having developed a metastatic hepatocellular carcinoma; wherein step (a) and step (b) each independently consists of the steps: (i) isolating RNA from the tissue sample and generating cDNA copies therefrom; (ii) quantitatively measuring the RNA levels expressed by the genes aldoa, arid3a, lgals1, hbegf, afp, slc35d2, cyp2c9, cyp4v2, limk2, acp2, lgals3, and ndrg1 by a Reverse Transcription Polymerase Chain Reaction (RT-PCR) assay, wherein the RT-PCR uses the PCR primer pairs: aldoa-specific SEQ ID NOs: 1 and 2; arid3a-specific SEQ ID NOs: 3 and 4; lgals1-specific SEQ ID NOs: 5 and 6; hbegf-specific SEQ ID NOs: 7 and 8; afp-specific SEQ ID NOs: 9 and 10; slc35d2-specific SEQ ID NOs: 11 and 12; cyp2c9-specific SEQ ID NOs: 13 and 14; cyp4v2-specific SEQ ID NOs: 15 and 16; limk2-specific SEQ ID NOs: 17 and 18; acp2-specific SEQ ID NOs: 19 and 20; lgals3-specific SEQ ID NOs: 21 and 22; and ndrg1-specific SEQ ID NOs: 23 and 24; and further uses the chemically-modified probes: aldoa-specific SEQ ID NO: 25; arid3a-specific SEQ ID NO: 26; lgals1-specific SEQ ID NO: 27; hbegf-specific SEQ ID NO: 28; afp-specific SEQ ID NO: 29; slc35d2-specific SEQ ID NO: 30; cyp2c9-specific SEQ ID NO: 31; cyp4v2-specific SEQ ID NO: 32; limk2-specific SEQ ID NO: 33; acp2-specific SEQ ID NO: 34; lgals3-specific SEQ ID NO: 35; and ndrg1-specific SEQ ID NO: 36, wherein each of the chemically-modified probes has a terminally attached fluorescent moiety and a terminally attached quenching moiety, and wherein the expression level of each gene is quantifiably measured by measuring the intensity of fluorescence from each of said gene-specific chemically-modified probes; (c) comparing the levels of gene expression of the first and the second gene expression signatures, wherein the relative levels of gene expression indicate the presence or absence of metastatic hepatocellular carcinoma cells in the first subject suspected of having a metastatic hepatocellular carcinoma; and (d) generating a report indicating the metastatic status of a hepatocellular carcinoma of the patient, wherein: (i) if the expression of the genes aldoa, arid3a, lgals1, hbegf, afp, slc35d2 of the first tissue sample is elevated compared to the expression level of the same genes of the second tissue sample, there is a reduced likelihood of survival of the first subject development from the carcinoma in the patient; and (ii) if the expression of the genes cyp2c9, cyp4v2, limk2, acp2, lgals3, and ndrg1 in the first tissue sample is elevated compared to the expression level of the same genes of the second tissue sample, said levels indicate an extended period of the first subject survival; and (e) adjusting a mode of treatment of a hepatocellular carcinoma of the patient from whom the first tissue sample was obtained.

Yet another aspect of the disclosure encompasses embodiments of a composition comprising at least one of the PCR primer pairs of the group consisting of: aldoa-specific SEQ ID NOs: 1 and 2; arid3a-specific SEQ ID NOs: 3 and 4; lgals1-specific SEQ ID NOs: 5 and 6; hbegf-specific SEQ ID NOs: 7 and 8; afp-specific SEQ ID NOs: 9 and 10; slc35d2-specific SEQ ID NOs: 11 and 12; cyp2c9-specific SEQ ID NOs: 13 and 14; cyp4v2-specific SEQ ID NOs: 15 and 16; limk2-specific SEQ ID NOs: 17 and 18; acp2-specific SEQ ID NOs: 19 and 20; lgals3-specific SEQ ID NOs: 21 and 22; and ndrg1-specific SEQ ID NOs: 23 and 24.

In some embodiments of this aspect of the disclosure, the composition further comprise at least one of the chemically-modified probes selected from the group consisting of: aldoa-specific SEQ ID NO: 25; arid3a-specific SEQ ID NO: 26; lgals1-specific SEQ ID NO: 27; hbegf-specific SEQ ID NO: 28; afp-specific SEQ ID NO: 29; slc35d2-specific SEQ ID NO: 30; cyp2c9-specific SEQ ID NO: 31; cyp4v2-specific SEQ ID NO: 32; limk2-specific SEQ ID NO: 33; acp2-specific SEQ ID NO: 34; lgals3-specific SEQ ID NO: 35; and ndrg1-specific SEQ ID NO: 36, wherein each of the chemically-modified probes has a terminally attached fluorescent moiety and a terminally attached quenching moiety.

In some embodiments of this aspect of the disclosure, the composition can comprise at least one of the PCR primer pairs and a chemically-modified probe of the group consisting of: aldoa-specific SEQ ID NOs: 1 and 2, and SEQ ID NO: 25; arid3a-specific SEQ ID NOs: 3 and 4, and SEQ ID NO: 26; lgals1-specific SEQ ID NOs: 5 and 6, and SEQ ID NO: 27; hbegf-specific SEQ ID NOs: 7 and 8, and SEQ ID NO: 28; afp-specific SEQ ID NOs: 9 and 10, and SEQ ID NO: 29; slc35d2-specific SEQ ID NOs: 11 and 12, and SEQ ID NO: 30; cyp2c9-specific SEQ ID NOs: 13 and 14, and SEQ ID NO: 31; cyp4v2-specific SEQ ID NOs: 15 and 16, and SEQ ID NO: 32; limk2-specific SEQ ID NOs: 17 and 18, and SEQ ID NO: 33; acp2-specific SEQ ID NOs: 19 and 20, and SEQ ID NO: 34; lgals3-specific SEQ ID NOs: 21 and 22, and SEQ ID NO: 35; and ndrg1-specific SEQ ID NOs: 23 and 24, and SEQ ID NO: 36.

Still another aspect of the disclosure encompasses embodiments of a kit comprising at least one container having at least one of the PCR primer pairs and a chemically-modified probe of the group consisting of: aldoa-specific SEQ ID NOs: 1 and 2, and SEQ ID NO: 25; arid3a-specific SEQ ID NOs: 3 and 4, and SEQ ID NO: 26; lgals1-specific SEQ ID NOs: 5 and 6, and SEQ ID NO: 27; hbegf-specific SEQ ID NOs: 7 and 8, and SEQ ID NO: 28; afp-specific SEQ ID NOs: 9 and 10, and SEQ ID NO: 29; slc35d2-specific SEQ ID NOs: 11 and 12, and SEQ ID NO: 30; cyp2c9-specific SEQ ID NOs: 13 and 14, and SEQ ID NO: 31; cyp4v2-specific SEQ ID NOs: 15 and 16, and SEQ ID NO: 32; limk2-specific SEQ ID NOs: 17 and 18, and SEQ ID NO: 33; acp2-specific SEQ ID NOs: 19 and 20, and SEQ ID NO: 34; lgals3-specific SEQ ID NOs: 21 and 22, and SEQ ID NO: 35; and ndrg1-specific SEQ ID NOs: 23 and 24, and SEQ ID NO: 36; and instructions for a method for determining whether a hepatocellular carcinoma tissue of a patient has a differential gene expression signature of a metastatic hepatocellular carcinoma tissue.

BRIEF DESCRIPTION OF THE DRAWINGS

Aspects of the present disclosure will be more readily appreciated upon review of the detailed description of its various embodiments, described below, when taken in conjunction with the accompanying drawings. The drawings are described in greater detail in the description and examples below.

FIG. 1A schematically illustrates the Tet system used to generate a transgenic mouse that co-expresses murine Twist1, human c-MYC, and firefly Luciferase (Luc) in hepatocytes. Hepatocellular carcinoma (HCC) was induced in adult animals by transgene activation upon removal of Doxycycline (Dox) from the water supply.

FIG. 1B is a graph illustrating that Twist1 cooperated with MYC to induce extra-hepatic HCC metastases in 52% of animals, with multiple target organs (n=21; p<0.001). MYC alone did not induce HCC metastasis (n=30).

FIG. 1C shows a series of digital images illustrating the gross anatomy of mice showed metastases in MYC/Twist1 animals (n=21) to the lymph nodes, spleen, and peritoneum (38%, p<0.001) and lungs (29%, p<0.001), and that MYC alone induced HCC without metastases, while Twist1 alone (n=15) had no discernible effect on liver weight or histology.

FIG. 1D shows a series of digital images illustrating immunohistochemistry (IHC) for MYC, which showed transgene expression at primary and metastatic sites, indicating that the metastases were derived from the MYC-induced primary tumors.

FIG. 1E shows a series of digital images illustrating immunohistochemistry shows that E-cadherin and β-catenin were expressed and localized to the cell periphery in MYC/Twist1 primary and metastatic HCC, and at levels comparable to normal liver, suggesting the maintenance of epithelial adherens junctions. MYC HCC showed heterogeneous and delocalized E-cadherin and β-catenin.

FIG. 2A shows a graph illustrating the abundance of circulating tumor cells (CTC's) in MYC/Twist1 mice during disease progression. Firefly Luciferase (FLuc) expression increased significantly during tumor onset (p=0.04), and then dramatically decreased upon MYC/Twist1 inactivation (p=0.0121) (after reintroducing Dox back to the water supply).

FIG. 2B shows a graph illustrating transgenic MYC (hMYC) expression used to assess the prevalence of CTC's and which showed an increase during disease onset (p=0.0335) and a significant decrease following MYC/Twist1 inactivation (p=0.0159).

FIG. 2C shows a series of digital images of X-ray computed tomography (microCT) during HCC progression. During tumor onset, lung metastases and an increase in liver size were detected. Upon MYC/Twist1 inactivation, lung metastases were no longer detectable, and the liver receded to pre-tumor size.

FIG. 2D shows a series of digital images of bioluminescent imaging (BLI) used on transplanted MYC/Twist1 HCC cells to investigate whether dormant tumor cells persist upon transgene inactivation. Tumors regressed and ceased to luminesce upon MYC/Twist1 inactivation. Reactivation of MYC and Twist1 induced rapid reemergence of luminescent tumors, indicating that dormant tumor cells persist following transgene inactivation.

FIGS. 3-6C illustrate a gene expression analysis of MYC/Twist1 primary versus metastatic tumors useful for the prediction of a clinical outcome in human HCC patients.

FIG. 3 is a graphical representation of gene clustering of significant genes from individual samples (ANOVA, p<0.05; >2-fold expression). NORMAL=normal liver, n=2; MYC HCC=MYC-induced HCC, n=2; MYC/Twist1 HCC=MYC/Twist1 HCC, n=6; MYC/Twist1 MET=MYC/Twist1 metastases, n=8.

FIG. 4 is a series of graphs illustrating that genes expressed in MYC/Twist1 HCC and MYC/Twist1 MET showed a strong enrichment in gene sets from two human MYC-related HCC data sets. Using gene lists established from comparing each tumor type to normal liver (unpaired t-test, p<0.05), GSEA analysis was conducted to compare murine HCC expression to human HCC and metastasis gene data sets.

FIG. 5 schematically illustrates tumor type comparison (unpaired t-test, p<0.05; >2-fold change from NORMAL) revealing gene signatures distinct to, or overlapping between, each tumor type.

FIG. 6C is a graphical boxplot separating HCC patient groups based on primary tumor metastasis using the MYC/Twist1 HCC+MET_UP signature (GSE364; unpaired t-test, p<0.00001).

FIG. 7 shows a Venn diagram of the comparison of genes between the mouse MYC/Twist1 HCC+MET_UP signature and a compilation of 5 existing human HCC metastasis signatures (Human HCC Total Metastasis Signature) that revealed 17 up-regulated genes that overlap between mouse and human HCC metastasis signatures.

FIGS. 8A and 8B are a pair of graphs illustrating that the 17-gene signature was prognostic of poor overall survival in human HCC patients (GSE364; Kaplan-Meier left curve; log-rank test, p=0.004). This finding was validated in an independent data set of human HCC patients, which showed similar poor prognosis for patients aligning with the 17 Gene Signature (GSE14520; Kaplan-Meier right curve; log-rank test, p=0.0012).

FIG. 8C is a graphical box plot demonstrating stratification of human HCC cohorts based on presence of metastases using the 17-gene signature (GSE364) (t-test of the means, p<0.00001).

FIG. 9A is a graph showing the results of qRT-PCR performed on 8 normal liver, and 40 cancer, samples from patients. A subset of human HCC has elevated Twist1 expression. Expression of Twist1 is variable across all 40 human HCC samples with some showing expression lower than, and some higher than, the spectrum of expression in normal liver.

FIG. 9B is a graphical box plot illustrating that the expression data of FIG. 9A was grouped into tissue type.

FIGS. 12-16 show that Twist1 increases migration, invasion, and metastasis of murine and human HCC cell lines.

FIG. 12 is a digital image of an immunoblot showing that the transduced cells express high levels of TWIST1 protein. Twist1 was retrovirally transduced into human Huh7 or a murine HCC cell line derived from LAP-tTA/TRE-MYC (MYC) mice.

FIG. 13 is a digital image of a scratch wound healing assay performed to demonstrate that Twist1 increases the migratory potential of murine and human HCC cells.

FIG. 14 is a graph showing a transwell collagen invasion assay wherein expression of Twist1 significantly increases the invasion of murine and human HCC cells in vitro (p<0.01 for each cell line).

FIG. 15 is a series of digital images showing that both MYC HCC (n=4) and MYC HCC transduced with Twist1 (n=4) were tumorigenic when injected intraperitoneally into immunocompromised SCID mice. Only MYC/Twist1 HCC exhibited evidence of metastases, with 2 of 4 mice showing tumorigenic growth on the kidneys.

FIG. 16 is a series of digital images showing that human HCC cell line Huh7 transduced with vector (n=4) or Twist1 (n=4) were injected intravenously into SCID mice to examine for metastatic growth. Twist1-expressing cells demonstrated metastatic lung growth in 3 of 4 mice, while animals injected with vector-transduced Huh7 showed no evidence of lung metastasis.

FIGS. 17A-17C show graphs illustrating that EMT markers are most highly expressed in MYC/Twist1 metastatic lesions.

FIG. 17A is a graph showing multiple mesenchymal markers associated with EMT examined by qRT-PCR. MYC/Twist1 primary and metastatic HCC were compared to MYC HCC. MMP2 showed a substantial increase in MYC/Twist1 primary HCC, although Fsp1, FoxC2, and MMP9 were increased in metastases relative to either MYC or MYC/Twist1 primary HCC. All values are shown as fold change relative to normal liver controls.

FIG. 17B is a graph showing an analysis of epithelial markers illustrating only modest reduction in expression of cytokeratins 8 and 18 (Ck8, Ck18), plakophilin-2 (Plako2), and connexin 32 (Cx32) in MYC/Twist1 compared to MYC HCC. These four markers together with occluding (Occ) showed significantly lower expression in MYC/Twist1 metastases.

FIG. 17C is a graph showing previously implicated inducers of EMT. Zeb1 showed the greatest increase between MYC and MYC/Twist1 primary HCC, and SIP1 showed an increase in metastases. Snail1 was largely unchanged between samples. Snail2/Slug showed reduced expression in MYC/Twist HCC and metastases relative to MYC HCC.

FIG. 18 is a box graph illustrating that peripheral blood collected from MYC/Twist1 mice analyzed by qRT-PCR for firefly luciferase (FLuc) as a marker of CTCs showed a 162-fold increase compared to normal control, and a 19-fold increase compared to MYC mice (p=0.0428). Expression was normalized to ubiquitin, averaged across multiple samples, and set relative to wild type mice.

FIG. 19 is a box graph illustrating that MYC/Twist1 mice showed a 2156-fold increase in transgenic human MYC (hMYC) expression compared to MYC mice (p=0.0007).

FIG. 21A is a graph showing that the MYC/Twist1 HCC+MET gene signature is a prognostic for poor overall survival in human HCC patients (GSE364; Kaplan-Meier left curve); in this particular human HCC cohort the survival comparison did not achieve statistical significance (log-rank test, p=0.12).

FIG. 21B is a graph showing that the 17-gene signature is prognostic for poor overall survival in human HCC patients (GSE1898; Kaplan-Meier right curve); in this particular human HCC cohort the survival comparison did not achieve statistical significance (log-rank test, p=0.16).

FIG. 26A is a schema showing that cell lines derived from the mouse Twist1/MYC HCC were generated and retrovirally transduced with constitutive MYC or Twist1 and injected intravenously (IV) into immunocompromised SCID mice.

FIG. 26B is a series of digital images showing that intravenous injection of HCC cells resulted in the formation of lung metastases when MYC and Twist1 are expressed.

FIG. 27 illustrates GSE364 (Ye et al., (2003) *Nat. Med.* 9: 416-423) Kaplan-Meier curve, lowest line; p=0.008). In the first dataset, the signature was highly prognostic. "High score" represents patient aligning with the 12-gene signature.

FIG. 28 illustrates a second dataset of HCC patients, where the signature predicted prognosis that trended towards significance. GSE1898; Kaplan-Meier curve, lower line; p=0.2).

FIG. 29 illustrates that the 12-gene signature was highly prognostic of poor survival in human HCC patients from the combined data sets (lower line; p=0.0002).

FIG. 30 illustrates the nucleotide sequences of forward and reverse primer pairs and the chemically modified gene-specific probes used in the Taqman™-based assays for the genes of the hepatocellular carcinoma-associated gene signature of the disclosure. The table also includes similar primer pairs and labeled probes for the detection of other genes tested in the experiments of the disclosure.

Figure 1A:
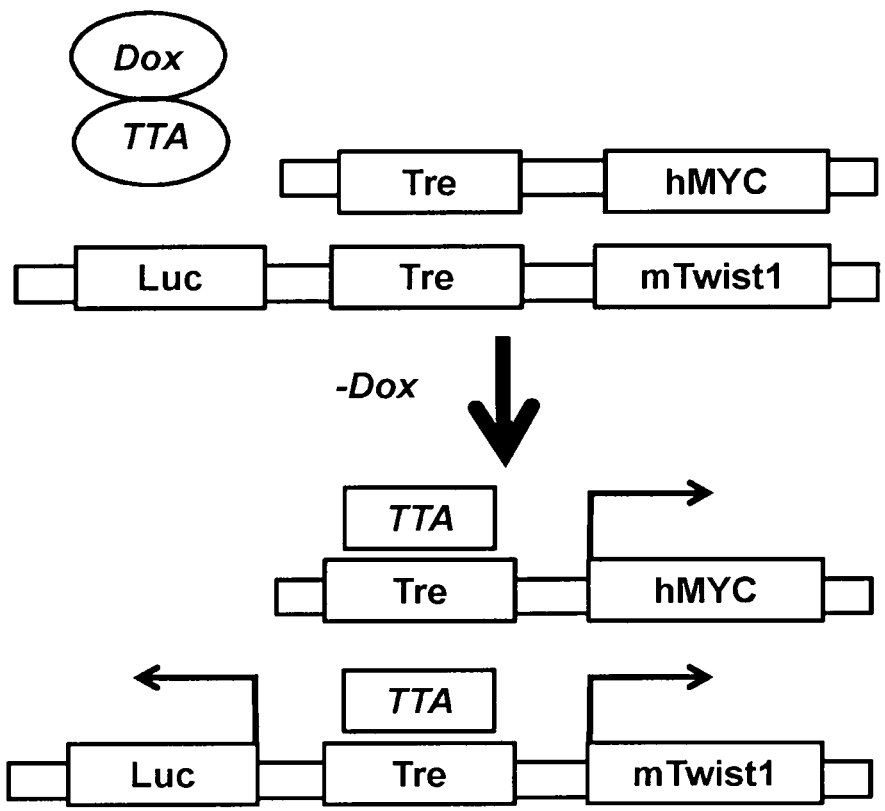
FIGS. 1A-1E illustrate that Twist1 facilitates metastasis of MYC-induced HCC.
Figure 1B:
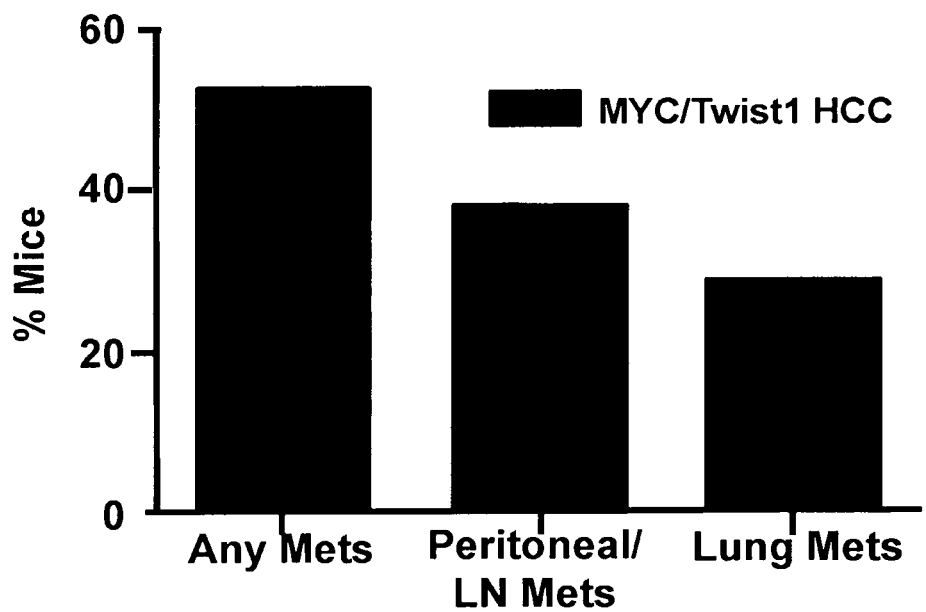
Figure 1C:
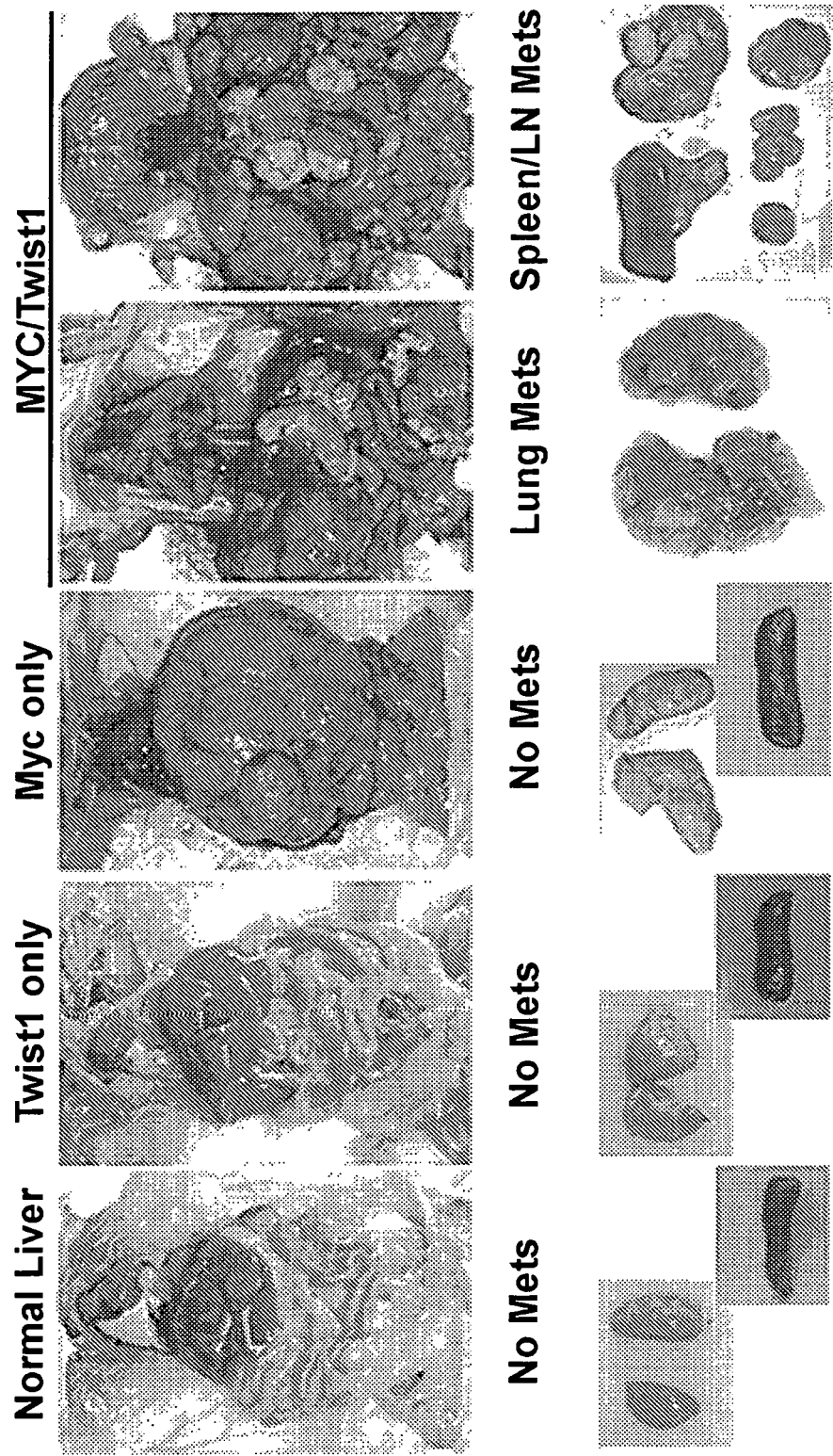
Figure 1D:
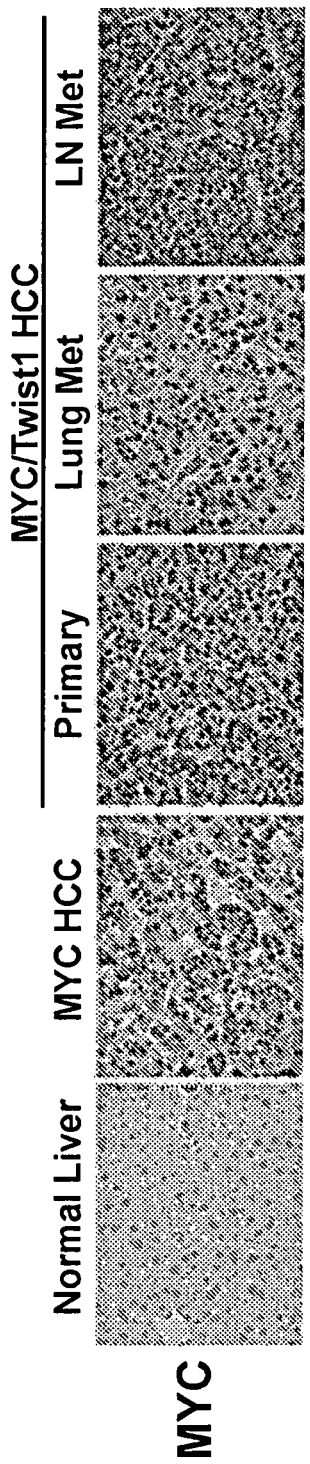
Figure 1E:
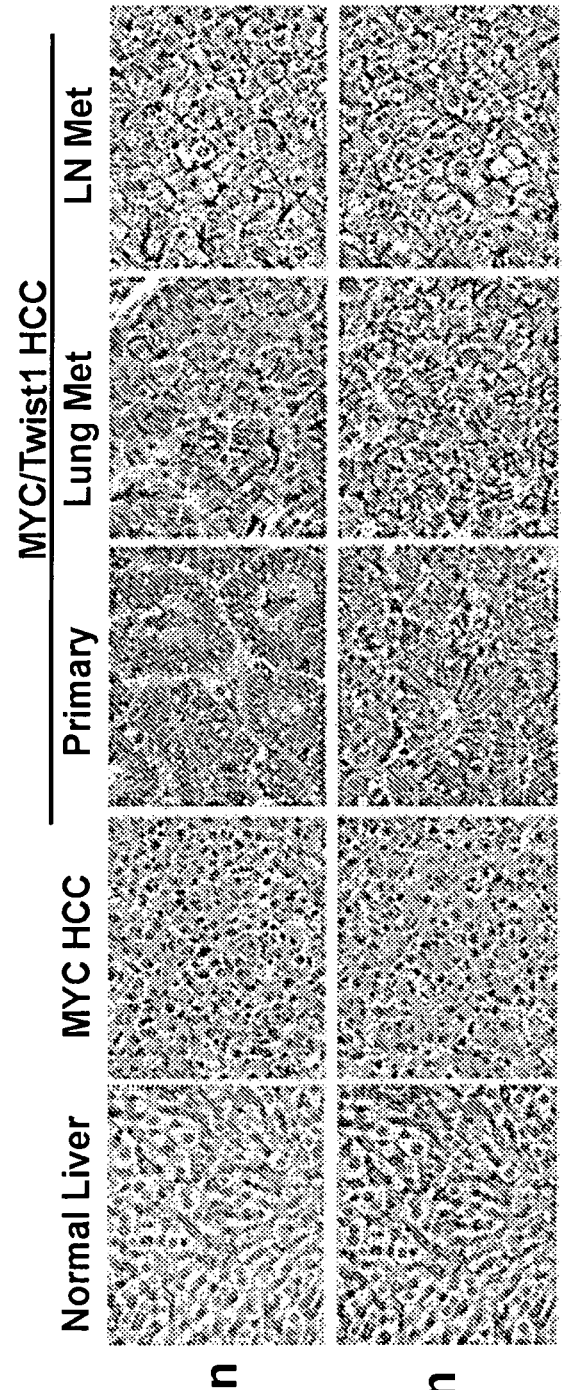
Figure 2A:
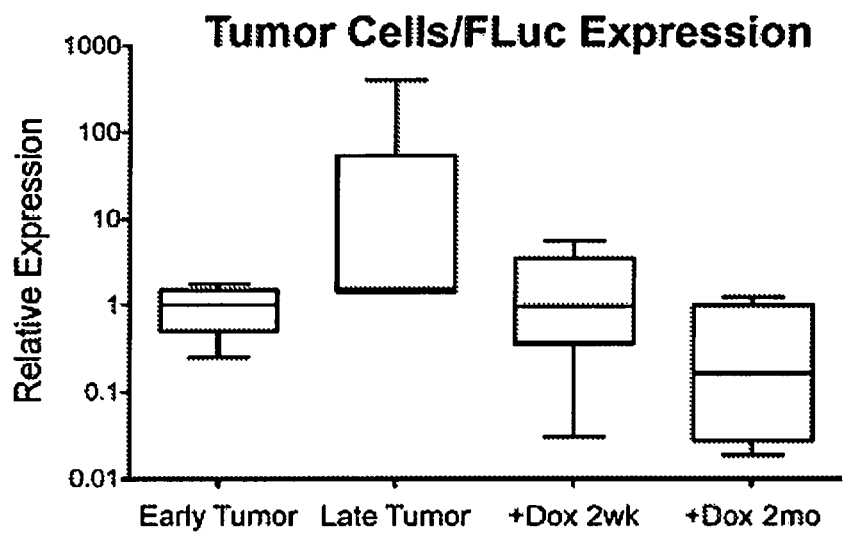
FIGS. 2A-2D illustrate metastatic HCC regression upon inactivation of Twist1 and MYC.
Figure 2B:
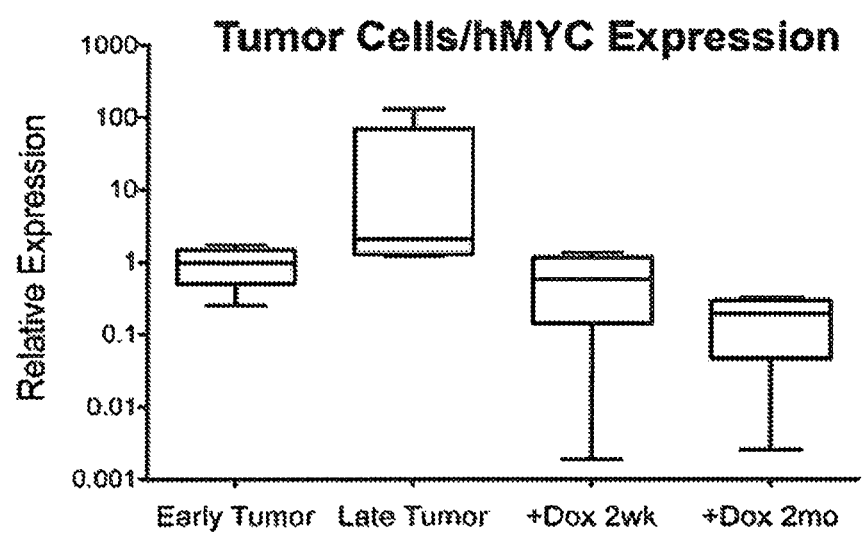
Figure 2C:
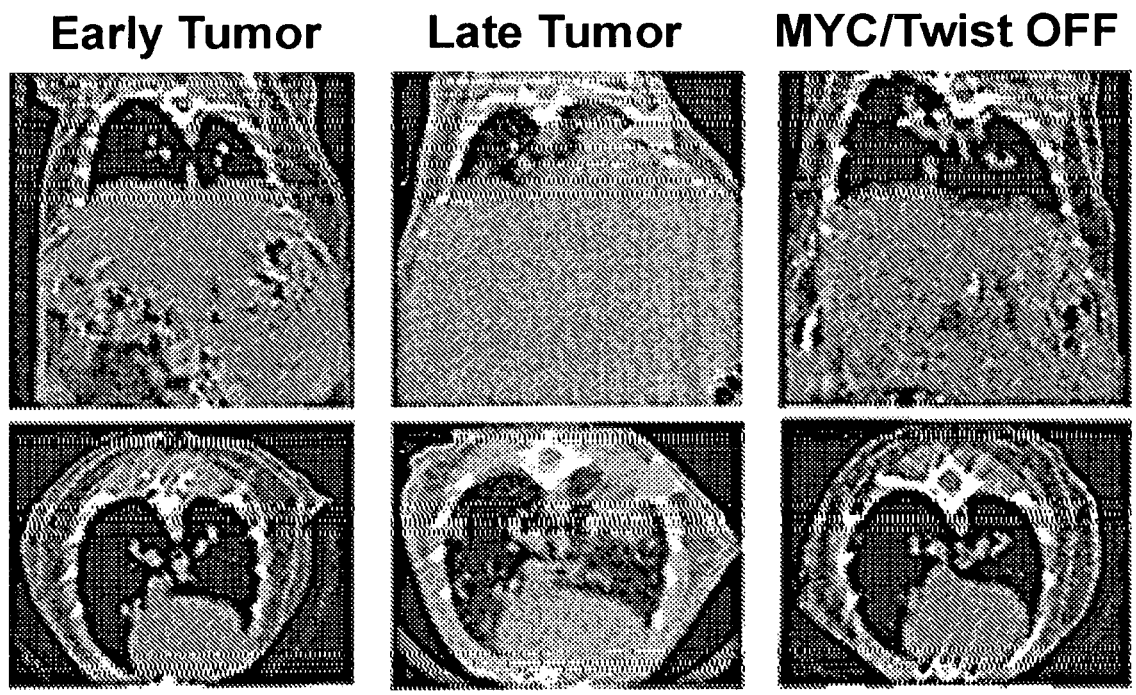
Figure 2D:
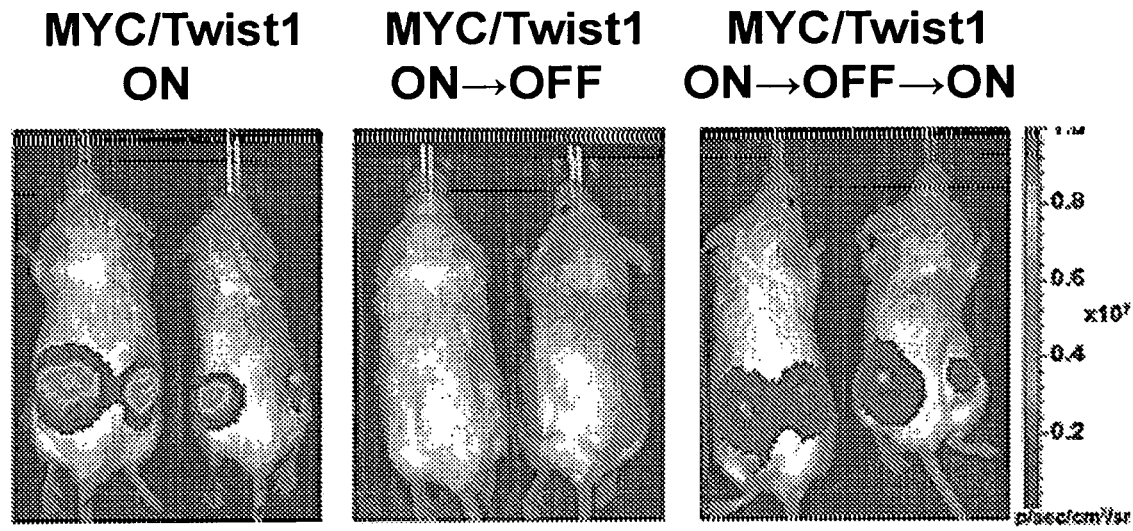

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

DESCRIPTION OF THE DISCLOSURE

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. Patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

Definitions

In describing and claiming the disclosed subject matter, the following terminology will be used in accordance with the definitions set forth below.

The term "gene" as used herein refers to a nucleic acid sequence that comprises control and coding sequences necessary for producing a polypeptide or precursor. The polypeptide may be encoded by a full length coding sequence or by any portion of the coding sequence. The gene may be derived in whole or in part from any source known to the art, including a plant, a fungus, an animal, a bacterial genome or episome, eukaryotic, nuclear or plasmid DNA, cDNA, viral DNA, or chemically synthesized DNA. A gene may contain one or more modifications in either the coding or the untranslated regions that could affect the biological activity or the chemical structure of the expression product, the rate of expression, or the manner of expression control. Such modifications include, but are not limited to, mutations, insertions, deletions, and substitutions of one or more nucleotides. The gene may constitute an uninterrupted coding sequence or it may include one or more introns, bound by the appropriate splice junctions.

The term "gene expression" refers to the process by which a nucleic acid sequence undergoes successful transcription and translation such that detectable levels of the nucleotide sequence are expressed.

The term "gene signature" as used herein refers to a group of genes expressed by a particular cell or tissue type wherein presence of the genes taken together, and particularly the differential expression of such genes, is indicative/predictive of a certain condition.

The terms "array" and "microarray" as used herein refer to the type of genes represented on an array by oligonucleotides, and where the type of genes s represented on the array is dependent on the intended purpose of the array (e.g., to monitor expression of human genes). The oligonucleotides on a given array may correspond to the same type, category, or group of genes. Genes may be considered to be of the same type if they share some common characteristics such as species of origin (e.g., human, mouse, rat); disease state (e.g., cancer); same biological process (e.g., apoptosis, signal transduction, cell cycle regulation, proliferation, differentiation). For example, one array type may be a "cancer array" in which each of the array oligonucleotides correspond to a gene associated with a cancer.

The term "differentially expressed" or "differential expression" as used herein refers to a difference in the level of expression of the biomarkers that can be assayed by measuring the level of expression of the products of the biomarkers, such as the difference in level of messenger RNA transcript expressed or proteins expressed of the biomarkers. In a preferred embodiment, the difference is statistically significant. The term "difference in the level of expression" refers to an increase or decrease in the measurable expression level of a given biomarker as measured by the amount of messenger RNA transcript and/or the amount of protein in a sample as compared with the measurable expression level of a given biomarker in a control. In one embodiment, the differential expression can be compared using the ratio of the level of expression of a given biomarker or biomarkers as compared with the expression level of the given biomarker or biomarkers of a control, wherein the ratio is not equal to 1.0. For example, an RNA or protein is differentially expressed if the ratio of the level of expression in a first sample as compared with a second sample is greater than or less than 1.0. For example, a ratio of greater than 1, 1.2, 1.5, 1.7, 2, 3, 3, 5, 10, 15, 20 or more, or a ratio less than 1, 0.8, 0.6, 0.4, 0.2, 0.1, 0.05, 0.001 or less. In another embodiment the differential expression is measured using p-value. For instance, when using p-value, a biomarker is identified as being differentially expressed as between a first sample and a second sample when the p-value is less than 0.1, preferably less than 0.05, more preferably less than 0.01, even more preferably less than 0.005, the most preferably less than 0.001.

The term "detectable" refers to an RNA expression pattern which is detectable via the standard techniques of polymerase chain reaction (PCR), reverse transcriptase-(RT) PCR, differential display, and Northern analyses, which are well known to those of skill in the art. The term "biological sample" refers to a sample obtained from an organism (e.g., a human patient) or from components (e.g., cells) of an organism. The sample may be of any biological tissue or fluid. The sample may be a "clinical sample" which is a sample derived from a patient. Such samples include, but are not limited to, sputum, blood, blood cells (e.g., white cells), amniotic fluid, plasma, semen, bone marrow, and tissue or fine needle biopsy samples, urine, peritoneal fluid, and pleural fluid, or cells therefrom. Biological samples may also include sections of tissues such as frozen sections taken for histological purposes. A biological sample may also be referred to as a "patient sample."

The term "quantitative real-Time PCR" as used herein, used interchangeably with the terms "quantitative PCR" (abbreviated "qPCR") and "real-time PCR (RT-PCR), refers to a method for simultaneous amplification, detection, and quantification of a target polynucleotide using double dye-labeled fluorogenic oligodeoxyribonucleotide probes during PCR and includes such methods as TaqMan, SYBR Green assays, and the like.

The term "TaqMan" as used herein refers to a PCR-based assay that utilizes an oligo-nucleotide probe containing a "fluorescent reporter"-"fluorescence quencher" pair, wherein the quencher molecule of the probe is designed to be located close enough to the reporter molecule to ensure that the fluorescence of the reporter molecule is quenched. The binding site of the probe is located between PCR primers used to amplify the target polynucleotide. Preferably, PCR is carried out using Taq DNA polymerase, AMPLITAQ (Perkin-Elmer, Norwalk, Conn.). During strand extension by Taq DNA polymerase, the annealed probe containing the reporter/quencher pair is digested by the 5'-3' exonuclease activity of the taq polymerase. Digestion of the probe results in the reporter molecule becoming separated from the quencher molecule; thus, the quencher molecule is no longer close enough to the reporter molecule to quench the reporter molecule's fluorescence. Therefore, as more and more annealed probes are digested during amplification, the number of unquenched reporter molecules in solution increases, resulting in a stronger and stronger fluorescent signal being produced during consecutive cycles. The primers according to the disclosure may also be useful as hybridization probes.

The fluorescently labeled probe contains a dye and quencher that are maintained in close proximity to one another by being attached to the same probe. When in close proximity, the dye is quenched by fluorescence resonance energy transfer to the quencher. Probes are designed that hybridize to a target nucleotide sequence. The detectably labeled probes may be optically labeled probes, such as fluorescently labeled probes. Examples of fluorescent labels include, but are not limited to Atto dyes: 4-acetamido-4'-isothiocyanatostiibene-2,2'disulfonic acid; acridine and derivatives: acridine, acridine isothiocyanate; 5-(2'-amino-ethyl)aminonaphthalene-1-sulfonic acid (EDANS); 4-amino-N-[3-vinylsulfonyl)phenyl]naphthalimide-3,5 disulfonate; N-(4-anilino-1-naphthyl)maleimide; anthranilamide; BODIPY; Brilliant Yellow; coumarin and derivatives: coumarin, 7-amino-4-methylcoumarin (AMC, Coumarin 120), 7-amino-4-trifluoromethylcouluarin (Coumaran 151); cyanine dyes; cyanosine; 4',6-diaminidino-2-phenylindole (DAPI); 5'5"-dibromopyrogallol-sulfonaphthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansylchloride); 4-dimethylaminophenylazophenyl-4'-isothiocyanate (DABITC); eosin and derivatives; eosin, eosin isothiocyanate, erythrosin and derivatives; erythrosin B, erythrosin, isothiocyanate; ethidium; fluorescein and derivatives; 5-carboxyfluorescein (FAM), 5-(4,6-dichlorotriazin-2-yl)aminofluorescein (DTAF), 2',7'-dimethoxy-4'5'-dichloro-6-carboxyfluorescein, fluorescein, fluorescein isothiocyanate, QFITC, (XRITC); fluorescamine; IR144; IR1446; Malachite Green isothiocyanate; 4-methylumbelliferoneortho cresol phthalein; nitrotyrosine; pararosaniline; Phenol Red; B-phycoerythrin; o-phthaldialdehyde; pyrene and derivatives: pyrene, pyrene butyrate, succinimidyl 1-pyrene; butyrate quantum dots; Reactive Red 4 (Cibacron™ Brilliant Red 3B-A) rhodamine and derivatives: 6-carboxy-X-rhodamine (ROX), 6-carboxyrhodamine (R6G), lissamine rhodamine B sulfonyl chloride rhodamine (Rhod), rhodamine B, rhodamine 123, rhodamine X isothiocyanate, sulforhodamine B, sulforhodamine 101, sulfonyl chloride derivative of sulforhodamine 101 (Texas Red); N,N,N', N'tetramethyl-6-carboxyrhodamine (TAMRA); tetramethyl rhodamine; tetramethyl rhodamine isothiocyanate (TRITC); riboflavin; rosolic acid; terbium chelate derivatives; Cy3; Cy5; Cy5.5; Cy7; IRD 700; IRD 800; La Jolta Blue; phthalo cyanine; and naphthalo cyanine. Preferred fluorescent labels are cyanine-3 and cyanine-5. Labels other than fluorescent labels are contemplated by the invention, including other optically-detectable labels.

Description

Embodiments of the methods of the present disclosure identify and validate a 12-member gene expression profile indicative of whether a hepatocellular carcinoma cancer has metastasized. In particular, the disclosure encompasses methods that employ novel chemically modified probes and primers that together may be incorporated into a PCR-based assay that determines the relative expressions of the genes hbegf, aldoa, arid3a, lgals1, hbegf, afp, slc35d2, cyp2c9, cyp4v2, limk2, acp2, lgals3, and ndrg1 of the 12-gene. panel. Co-expression or a co-reduction in gene expression in some or all of the genes of the 12-member gene panel usefully indicate whether the patient has a metastatic hepatocellular carcinoma and provides an indication of the likelihood of a metastasis The present method can utilize testing in which, in one track, those genes which are over-/under-expressed as compared to normal (non-cancerous) tissue samples are identified. Positive and negative controls may be employed to normalize the results, including eliminating those genes and proteins that also are differentially expressed in normal tissues from the same patients, and confirming that the gene expression profile is unique to the cancer of interest.

Gene expression profiles (GEPs) can be generated from biological samples based on total RNA. Briefly, the method involves isolating total RNA from the biological sample, amplifying the RNA, synthesizing cDNA, labeling the cDNA with a detectable label, hybridizing the cDNA with a genomic array, such as the AFFYMETRIX U133 GENECHIP™, and determining binding of the labeled cDNA with the genomic array by measuring the signal intensity from the detectable label bound to the array.

mRNAs in the tissue samples can be analyzed using the customized probes according to the disclosure, and in particular the chemically modified gene-specific probes that can specifically hybridize to and detect the mRNA expression products of the genes hbegf, aldoa, arid3a, lgals1, hbegf, afp, slc35d2, cyp2c9, cyp4v2, limk2, acp2, lgals3, and ndrg1, or oligonucleotide arrays, such as cDNA or oligonucleotide arrays. The use of these arrays allows for the measurement of steady-state mRNA levels of the 12 genes simultaneously, thereby presenting a powerful tool for identifying effects such as the onset, arrest or modulation of uncontrolled cell proliferation. Hybridization and/or binding of the probes on the arrays to the nucleic acids of interest from the cells can be determined by detecting and/or measuring the location and intensity of the signal received from the labeled probe or used to detect a DNA/RNA sequence from the sample that hybridizes to a nucleic acid sequence at a known location on the microarray. The intensity of the signal is proportional to the quantity of cDNA or mRNA present in the sample tissue. Numerous arrays and techniques are available and useful. Methods for determining gene and/or protein expression in sample tissues are described, for example, in U.S. Pat. Nos. 6,271,002; 6,218,122; 6,218,114; and 6,004,755; and in Wang et al., (2004) *J. Clin. Oncol.* 22: 1564-1671 (2004); Schena et al., (1995) *Science* 270: 467-470; all of which are incorporated herein by reference.

As a first step in the methods of the disclosure to identify the genes hbegf, aldoa, arid3a, lgals1, hbegf, afp, slc35d2, cyp2c9, cyp4v2, limk2, acp2, lgals3, and ndrg1 of the 12-gene panel, RNA can be isolated from the tissue samples and labeled. Parallel processes were run on the sample to develop data regarding an over- or under-expression of genes based on mRNA levels. Over- or under-expression of the genes in each cancer tissue sample can be compared to gene expression in the normal (non-cancerous) samples. Preferably, levels of up- and down-regulation are distinguished based on fold changes of the intensity measurements of hybridized microarray probes. A difference of about 2.0 fold or greater is preferred for making such distinctions, or a p-value of less than about 0.05. That is, before a gene is said to be differentially expressed in diseased versus normal cells, the diseased cell is found to yield at least about 2 times greater or less intensity of expression than the normal cells. Generally, the greater the fold difference (or the lower the p-value), the more preferred is the gene for use as a diagnostic or prognostic tool. Genes selected for the gene signatures of the present disclosure have expression levels that result in the generation of a signal that is distinguishable from those of the normal or non-modulated genes by an amount that exceeds background using clinical laboratory instrumentation.

Statistical values can be used to confidently distinguish modulated from non-modulated genes and noise. Statistical tests can identify the genes most significantly differentially expressed between diverse groups of samples. The Student's t-test is an example of a robust statistical test that can be used to find significant differences between two groups. The lower the p-value, the more compelling the evidence that the gene is showing a difference between the different groups. Nevertheless, since microarrays allow measurement of more than one gene at a time, tens of thousands of statistical tests may be asked at one time. Because of this, it is unlikely to observe small p-values just by chance, and adjustments using a Sidak correction or similar step as well as a randomization/permutation experiment can be made. A p-value less than about 0.05 by the t-test is evidence that the expression level of the gene is significantly different. More compelling evidence is a p-value less then about 0.05 after the Sidak correction is factored in. For a large number of samples in each group, a p-value less than about 0.05 after the randomization/permutation test is the most compelling evidence of a significant difference.

Another parameter that can be used to select genes that generate a signal that is greater than that of the non-modulated gene or noise is the measurement of absolute signal difference. Preferably, the signal generated by the differentially expressed genes differs by at least about 20% from those of the normal or non-modulated gene (on an absolute basis). It is even more preferred that such genes produce expression patterns that are at least about 30% different than those of normal or non-modulated genes.

This differential expression analysis can be performed using commercially available arrays, for example, AFFYMETRIX U133GENECHIP™ arrays (Affymetrix, Inc.). These arrays have probe sets for the whole human genome immobilized on the chip, and can be used to determine up- and down-regulation of genes in test samples. Other substrates having affixed thereon human genomic DNA or probes capable of detecting expression products, such as those available from Affymetrix, Agilent Technologies, Inc. or Illumina, Inc., also may be used. Currently preferred gene microarrays include Affymetrix U133 GENECHIP™ arrays and Agilent Technologies genomic cDNA microarrays. Instruments and reagents for performing gene expression analysis are commercially available. See, e.g., AFFYMETRIX GENECHIP™ System. The expression data obtained from the analysis then is input into the database. The analyses are carried out on the same samples from the same patients to generate parallel data. The same chips and sample preparation are used to reduce variability.

The expression of certain genes known as "reference genes" "control genes" or "housekeeping genes" can also be determined, preferably at the same time, as a means of ensuring the veracity of the expression profile. Reference genes are genes that are consistently expressed in many tissue types, including cancerous and normal tissues, and thus are useful to normalize gene expression profiles. See, e.g., Silvia et al., (2006) *BMC Cancer* 6: 200; Lee et al., (2002) *Genome Research*, 12: 292-297; Zhang et al., (2005) *BMC Mol. Biol.*, 6: 4). Determining the expression of reference genes in parallel with the genes in the unique gene expression profile provides further assurance that the techniques used for determination of the gene expression profile are working properly. The expression data relating to the reference genes also is input into the database. In a currently preferred embodiment, the following genes are used as reference genes: actb, gapdh, gusB, rplp0 and/or trfC.

The gene expression analysis identifies a gene expression profile (GEP) unique to the cancer samples, that is, those genes which are differentially expressed by the cancer cells. This GEP then is validated, for example, using real-time quantitative polymerase chain reaction (RT-qPCR), which may be carried out using commercially available instruments and reagents, such as those available from Applied Biosystems.

The term "prognosis" as used herein refers to the prediction of the likelihood of cancer-attributable death or progression, including recurrence, metastatic spread, and drug resistance, of a neoplastic disease, such as HCC. The predictive methods of the present invention can be used clinically to make treatment decisions by choosing the most appropriate treatment modalities for any particular patient. The predictive methods of the present invention are valuable tools in predicting if a patient is likely to respond favorably to a treatment regimen, such as surgical intervention, chemotherapy with a given drug or drug combination, and/or radiation therapy. The term "prognosis" is also used herein to refer to the prediction of the likelihood of cancer-attributable death or progression, including recurrence, metastatic spread, and drug resistance, of a neoplastic disease, such as HCC.

The term "tumor" as used herein refers to all neoplastic cell growth and proliferation, whether malignant or benign, and all pre-cancerous and cancerous cells and tissues.

The terms "cancer" and "cancerous" refer to or describe the physiological condition in mammals that is typically characterized by unregulated cell growth In the context of the present invention, reference to "at least one," "at least two," "at least five," etc. of the genes listed in any particular gene set means any one or any and all combinations of the genes listed.

The terms "expression threshold" and "defined expression threshold" are used interchangeably and refer to the level of a gene or gene product in question above which the gene or gene product serves as a predictive marker for patient survival without cancer recurrence. The threshold is defined experimentally from clinical studies such as those described in the Example below. The expression threshold can be selected either for maximum sensitivity, or for maximum selectivity, or for minimum error. The determination of the expression threshold for any situation is well within the knowledge of those skilled in the art.

Abbreviations

HCC, hepatocellular carcinoma; TRE, tetracycline responsive element; Luc, luciferase; ORF, open reading frame; BLI, bioluminescence imaging; LAP-tTA, liver-specific transactivator; GSEA, gene set enrichment analysis; H&E, hematoxylin and eosin; EMT, epithelial-mesenchymal transition; MET, metastasis; CTC, circulating tumor cell; Dox, Doxycycline; hbegf: gene encoding human heparin-binding EGF-like growth factor; aldoa: gene encoding aldolase A; lgals1: gene encoding galectin-1; plp2: gene encoding proteolipid protein 2; kifc1: gene encoding kinesin-like protein1; limk2: gene encoding LIM domain kinase 2; sccpdh: gene encoding saccharopine dehydrogenase; coro1c: gene encoding coronin-1C; ndrg1: gene encoding NDRG1 (N-myc downstream regulated 1); uap1l1: gene encoding UDP-N-acteylglucosamine pyrophosphorylase 1; iqgap1 gene encoding Ras GTPase-activating-like protein (p195); afp: gene encoding alpha-fetal protein (variously AFP, α-fetoprotein, alpha-1-fetoprotein, alpha-fetoglobulin); tbc1d1: gene encoding TBC1D1, a putative GTPase-activating protein of the Rab family protein), eno2: gene encoding enolase 2; lpl: gene encoding lipoprotein lipase; pygb: gene encoding phosphorylase, glycogen; brain; map3k6: gene encoding mitogen-activated protein kinase kinase kinase 6; acp2: gene encoding acid phosphatase 2; cyp4v2: gene encoding cytochrome P450, family 4, subfamily V, polypeptide 2; gstm6: gene encoding glutathione S-transferase mu 6.

Description

To directly interrogate the potential role and mechanism by which Twist1 contributes to metastasis a new conditional transgenic mouse model of Twist1/MYC-induced HCC has been generated. Twist1 can confer an invasive and metastatic phenotype in vivo. Importantly, the transgenic mouse models of non-metastatic and metastatic HCC of the disclosure could be used to identify a gene signature that is highly prognostic in human patients with HCC.

The practice of the present disclosure employs, unless otherwise indicated, conventional techniques of molecular biology (including recombinant techniques), microbiology, cell biology, and biochemistry, which are within the skill of the art. Such techniques are explained fully in the literature, such as, "Molecular Cloning: A Laboratory Manual", 2nd edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology", 4th edition (Weir & Blackwell, eds., Blackwell Science Inc., 1987); "Gene Transfer Vectors for Mammalian Cells" (Miller & Calos, eds., 1987); "Current Protocols in Molecular Biology" (Ausubel et al., eds., 1987); and "PCR: The Polymerase Chain Reaction", (Mullis et al., eds., 1994).

In general, methods of gene expression profiling can be divided into two large groups: methods based on hybridization analysis of polynucleotides, and methods based on sequencing of polynucleotides. The most sensitive and most flexible quantitative method is RT-PCR, which can be used to compare mRNA levels in different sample populations, in normal and tumor tissues, with or without drug treatment, to characterize patterns of gene expression, to discriminate between closely related mRNAs, and to analyze RNA structure.

The first step is the isolation of mRNA from a target sample. The starting material is typically total RNA isolated from human tumors or tumor cell lines, and corresponding normal tissues or cell lines, respectively. In embodiments of the present disclosure the total RNA samples can be isolated from cells that are of a metastatic HCC or a non-metastatic HCC, or both. Thus RNA can be isolated from a primary tumor. If the source of mRNA is a primary tumor, mRNA can be extracted, for example, from frozen or archived paraffin-embedded and fixed (e.g. formalin-fixed) tissue samples.

General methods for mRNA extraction are well known in the art and are disclosed in standard textbooks of molecular biology, including Ausubel et al., Current Protocols of Molecular Biology, John Wiley & Sons (1997). Methods for RNA extraction from paraffin-embedded tissues are disclosed, for example, in Rupp & Locker (1987) *Lab. Invest.* 56:A67 and De Andres et al., (1995) *BioTechniques* 18: 42-44. In particular, RNA isolation can be performed using a purification kit, buffer set and protease from commercial manufacturers, such as Qiagen, according to the manufacturer's instructions. For example, total RNA from cells in culture can be isolated using QIAGEN RNEASY™ mini-columns. Other commercially available RNA isolation kits include MASTERPURE™. Complete DNA and RNA Purification Kit (EPICENTRE™, Madison, Wis.) and Paraffin Block RNA Isolation Kit (Ambion, Inc.) were used. Total RNA from tissue samples can be isolated using RNA Stat-60 (Tel-Test). RNA prepared from a tumor can be isolated, for example, by cesium chloride density gradient centrifugation.

As RNA cannot serve as a template for PCR, the first step in gene expression profiling by RT-PCR is the reverse transcription of the RNA template into cDNA, followed by its exponential amplification in a PCR reaction. The two most commonly used reverse transcriptases are avian myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, Calif., USA), following the manufacturer's instructions. The derived cDNA can then be used as a template in the subsequent PCR reaction.

Although the PCR step can use a variety of thermostable DNA-dependent DNA polymerases, it typically employs Taq DNA polymerase, which has a 5'-3' nuclease activity but lacks a 3'-5' proofreading endonuclease activity. Thus, TAQMAN™ PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TAQMAN™ RT-PCR can be performed using commercially available equipment, such as, for example, the ABI PRISM 7700™ sequence detection system (Perkin-Elmer-Applied Biosystems, Foster City, Calif., USA), or LIGHT-CYCLER™ (Roche Molecular Biochemicals, Mannheim, Germany). The 5' nuclease procedure can be run on a real-time quantitative PCR device such as the ABI PRISM 7700™ sequence detection system. The system consists of a thermocycler, laser, charge-coupled device (CCD), camera and computer. The system amplifies samples in a 96-well format on a thermocycler. During amplification, laser-induced fluorescent signal is collected in real-time through fiber optics cables for all 96 wells, and detected at the CCD. The system includes software for running the instrument and for analyzing the data.

To minimize errors and the effect of sample-to-sample variation, RT-PCR is usually performed using an internal standard. The ideal internal standard is expressed at a constant level among different tissues, and is unaffected by the experimental treatment. RNAs most frequently used to normalize patterns of gene expression are mRNAs for the housekeeping genes glyceraldehyde-3-phosphate-dehydrogenase (GAPDH) and β-actin.

A more recent variation of the RT-PCR technique is the real time quantitative PCR, which measures PCR product accumulation through a dual-labeled fluorigenic probe (i.e., TAQMAN™ probe). Real time PCR is compatible both with quantitative competitive PCR, where internal competitor for each target sequence is used for normalization, and with quantitative comparative PCR using a normalization gene contained within the sample, or a housekeeping gene for RT-PCR. For further details see, e.g. Held et al., (1996) *Genome Research* 6: 986-994.

The steps of a representative protocol for profiling gene expression using fixed, paraffin-embedded tissues as the RNA source, including mRNA isolation, purification, primer extension and amplification are given in various published journal articles (for example: Godfrey et al., (2000) *J. Molec. Diagnostics* 2: 84-91; Specht et al., (2001) *Am. J. Pathol.* 158: 419-29). Briefly, a representative process starts with cutting about 10 µm thick sections of paraffin-embedded tumor tissue samples. The RNA is then extracted, and protein and DNA are removed. After analysis of the RNA concentration, RNA repair and/or amplification steps may be included, if necessary, and RNA is reverse transcribed using gene specific promoters followed by RT-PCR.

PCR primers and probes can be designed based upon intron sequences present in the gene to be amplified. In this embodiment, the first step in the primer/probe design is the delineation of intron sequences within the genes. This can be done by publicly available software, such as the DNA BLAT software developed by Kent, W. J., (2002) *Genome Res.* 12:v656-664, or by the BLAST software including its variations. Subsequent steps follow well established methods of PCR primer and probe design.

To avoid non-specific signals, it is important to mask repetitive sequences within the introns when designing the primers and probes. This can be easily accomplished by using the Repeat Masker program available on-line through the Baylor College of Medicine, which screens DNA sequences against a library of repetitive elements and returns a query sequence in which the repetitive elements are masked. The masked intron sequences can then be used to design primer and probe sequences using any commercially or otherwise publicly available primer/probe design packages, such as PRIMER EXPRESS™ (Applied Biosystems); MGB assay-by-design (Applied Biosystems); Primer3 (Rozen & Skaletsky (2000) in: Krawetz & Misener (eds) Bioinformatics Methods and Protocols: Methods in Molecular Biology. Humana Press, Totowa, N.J., pp 365-386).

The most important factors considered in PCR primer design include primer length, melting temperature (Tm), and G/C content, specificity, complementary primer sequences, and 3'-end sequence. In general, optimal PCR primers are generally 17-30 bases in length, and contain about 20-80%, such as, for example, about 50-60% G+C bases. Tm's between 50° C. and 80° C., e.g. about 50 to 70° C. are typically preferred.

For further guidelines for PCR primer and probe design see, e.g. Dieffenbach et al., "General Concepts for PCR Primer Design" in: PCR Primer, A Laboratory Manual, Cold Spring Harbor Laboratory Press, New York, 1995, pp. 133-155; Innis and Gelfand, "Optimization of PCRs" in: PCR Protocols, A Guide to Methods and Applications, CRC Press, London, 1994, pp. 5-11; and Plasterer, T. N. Primerselect: Primer and probe design. Methods Mol. Biol. 70:520-527 (1997), the entire disclosures of which are hereby expressly incorporated by reference.

Differential gene expression can also be identified, or confirmed using the microarray techniques according to the methods of the present disclosure. Thus, the expression profiles of metastasized and non-metastasized HCC-associated genes can be measured in either fresh or paraffin-embedded tumor tissue, using microarray technology. In these methods, polynucleotide sequences of interest (including cDNAs and oligonucleotides) are plated, or arrayed, on a microchip substrate. The arrayed sequences are then hybridized with specific DNA probes from cells or tissues of interest. Just as in the RT-PCR method, the source of mRNA typically is total RNA isolated from human tumors or tumor cell lines, and corresponding normal tissues or cell lines. Thus RNA can be isolated from a variety of primary tumors or tumor cell lines. If the source of mRNA is a primary tumor, mRNA can be extracted, for example, from frozen or archived paraffin-embedded and fixed (e.g. formalin-fixed) tissue samples, which are routinely prepared and preserved in everyday clinical practice.

In a specific embodiment of the microarray technique, but not intended to be limiting, PCR-amplified inserts of cDNA clones are applied to a substrate in a dense array. Preferably at least 10,000 nucleotide sequences can be applied to the substrate. The microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the chip is scanned by confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., (1996) Proc. Natl. Acad. Sci. USA 93: 106-149). Microarray analysis can be performed by commercially available equipment, following manufacturer's protocols, such as by using the AffymetrixGenChip technology, or Incyte's microarray technology. MYC/Twist1 HCC can be used to model human liver cancer The addition of a single gene, Twist1, is sufficient to cause non-metastatic MYC-induced HCC tumors to now metastasize. Accordingly, the transgenic mouse model of non-metastatic versus metastatic HCC of the present disclosure provides a means of identifying genes predictive of metastasis and poor outcome in human HCC.

Figure 3:
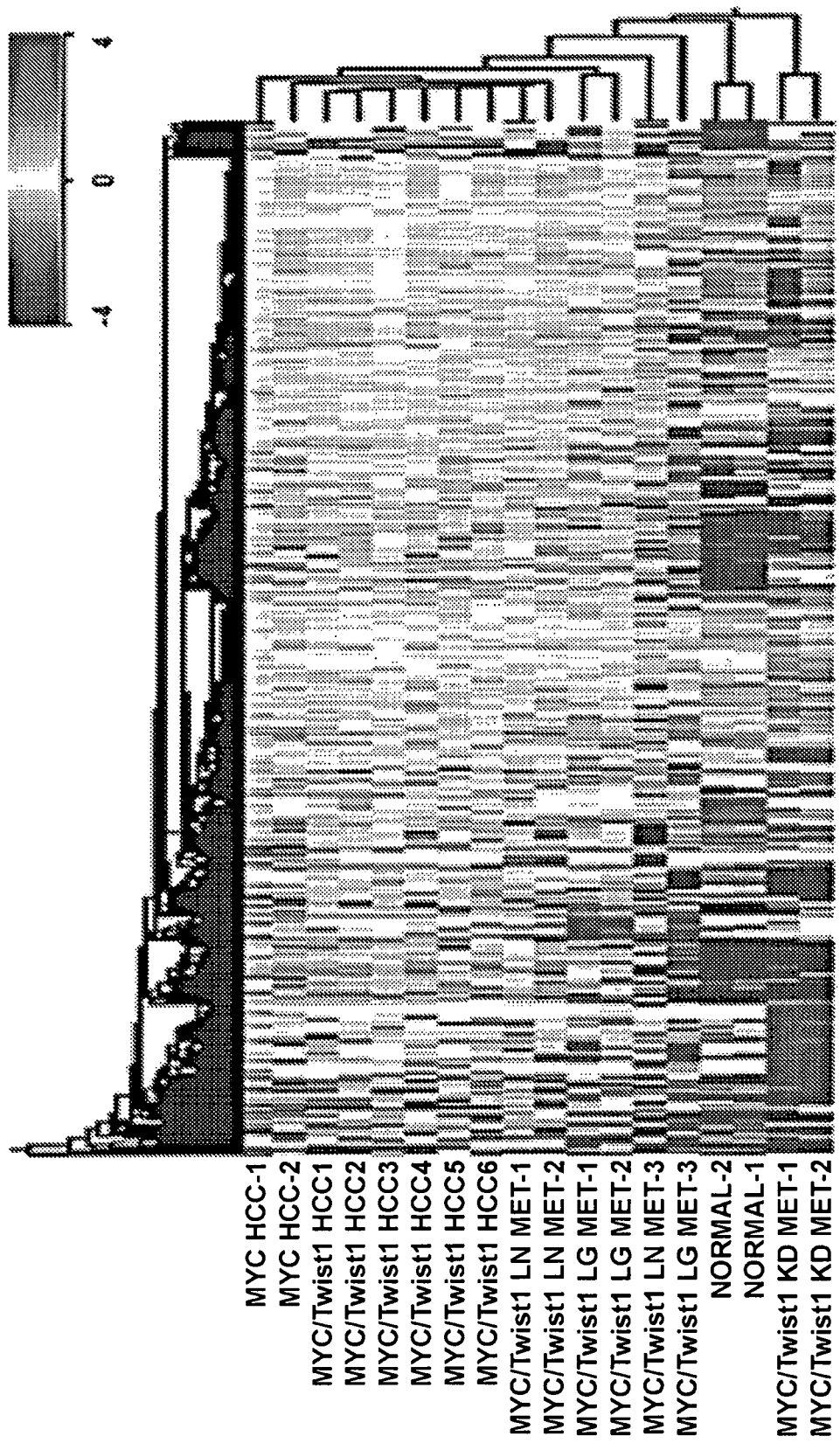
Figure 4:
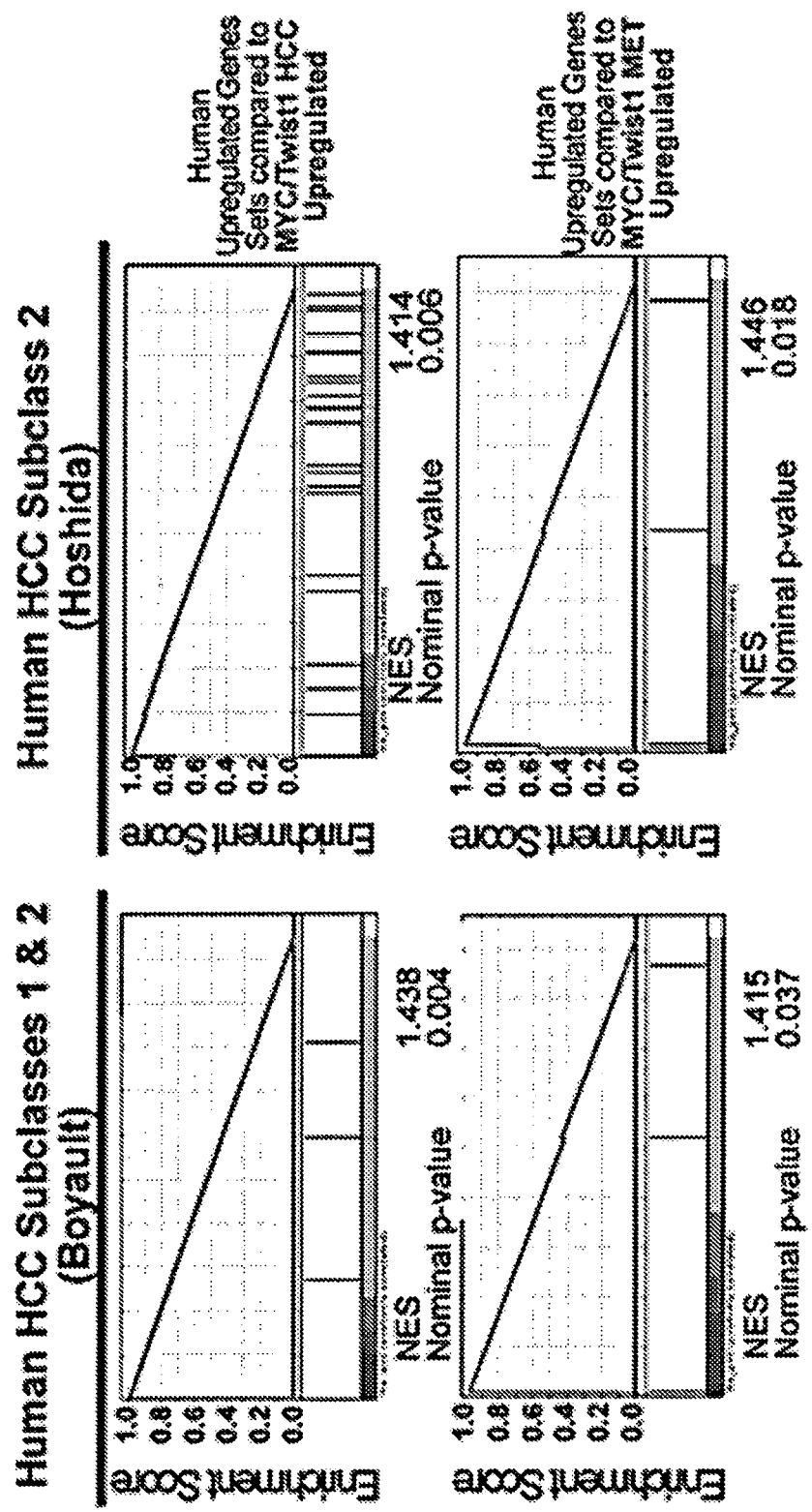
Figure 5:
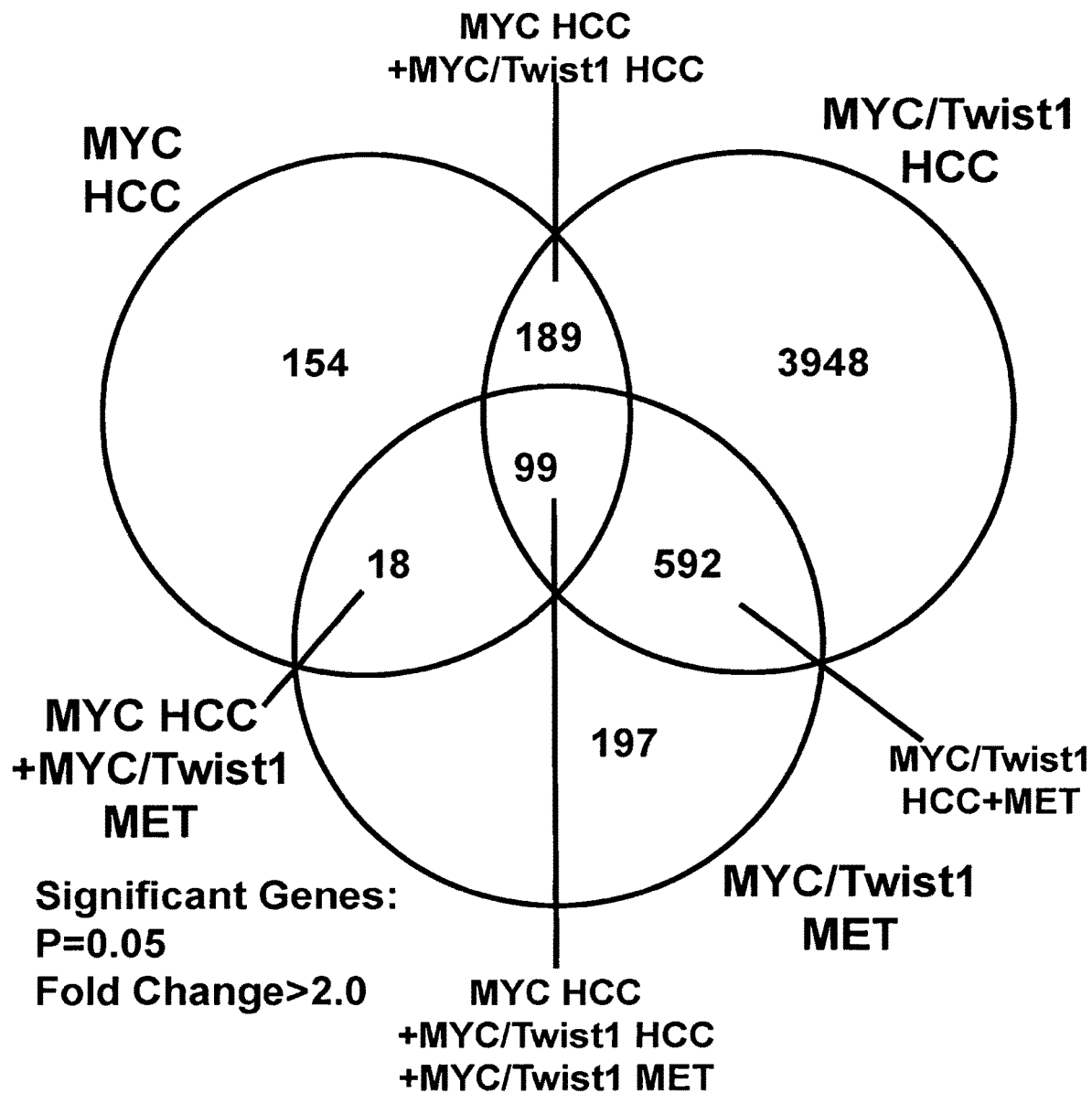

Expression microarrays were performed on MYC primary HCC (MYC HCC, n=2), MYC/Twist1 primary HCC (MYC/Twist1 HCC, n=6), MYC/Twist1 metastatic lesions (MYC/Twist1 MET, n=8), and normal liver (NORMAL, n=2). Data then were grouped and clustered (FIG. 3; ANOVA, p=0.05, FC>2, compared to NORMAL). Through the use of a GSEA ranked-list analysis, mouse and human HCC gene expressions were compared and found that MYC/Twist1 primary and metastatic tumors were highly similar to human HCC tumors associated with both MYC over-expression and poor prognosis (Boyault et al., (2007) Hepatology 45: 42-52; Hoshida et al., (2009) Cancer Res. 69: 7385-7392) (FIG. 4). Accordingly, the MYC and MYC/Twist1 transgenic models of the disclosure have gene expression programs that correspond to human HCC.

Genes were also identified that were uniquely and statistically significantly expressed in MYC/Twist1 primary HCC, or MYC/Twist1 Mets. From comparing these results to gene sets from MeSH term pathway analysis in Cytoscape, these genes were associated with EMT (p=0.0243), metastasis (p=0.0747), and invasion (p=0.0973), as shown in Tables 2 and 3). Thus, analysis of the mouse model of MYC/Twist1 induced HCC identified genes that are associated with invasion and metastasis.

Gene Signatures from Metastatic Mouse HCC are Prognostic in Human Patients

The MYC/Twist1 transgenic animal model of the present disclosure was examined to determine if it could be used to identify genes that could predict clinical outcome in patients with HCC. Microarray data from MYC-induced HCC primary tumors that are non-metastatic were compared with MYC/Twist1-induced HCC primary tumors, and MYC/Twist1-induced metastatic HCC. From these comparisons genes were identified that are differentially regulated only in MYC HCC (154 genes), MYC/Twist1 HCC (3948 genes), or MYC/Twist1 MET (197 genes), or genes whose expression overlapped between groups: MYC/Twist1 HCC+MYC/Twist MET (hereto referred to as MYC/Twist1 HCC+MET; 592 genes); MYC HCC+MYC/Twist1 HCC (189 genes) MYC HCC+MYC/Twist1 MET (18 genes), and MYC HCC+MYC/Twist1 HCC+MYC/Twist1 MET (99 genes; FIG. 3C).

These signatures were evaluated as to whether they were associated with clinical outcomes by analyzing them in the context of 4 prior studies of human HCC with microarray and survival data comprising a total of 273 patients. Whether the memberships of these gene sets were skewed towards genes whose expression level was correlated with good or poor prognosis was tested w, as assessed by their Z-score in Cox regression. The MYC/Twist1 HCC+MET gene signature was most strongly associated with poor survival in human HCC patients (p<0.00001, NES=1.749, FDR=0.0132 for 215 up-regulated genes; p<0.00001, NES=−2.018, FDR=6.33E-04 for 84 down-regulated genes) (Table 2).

Figure 18:
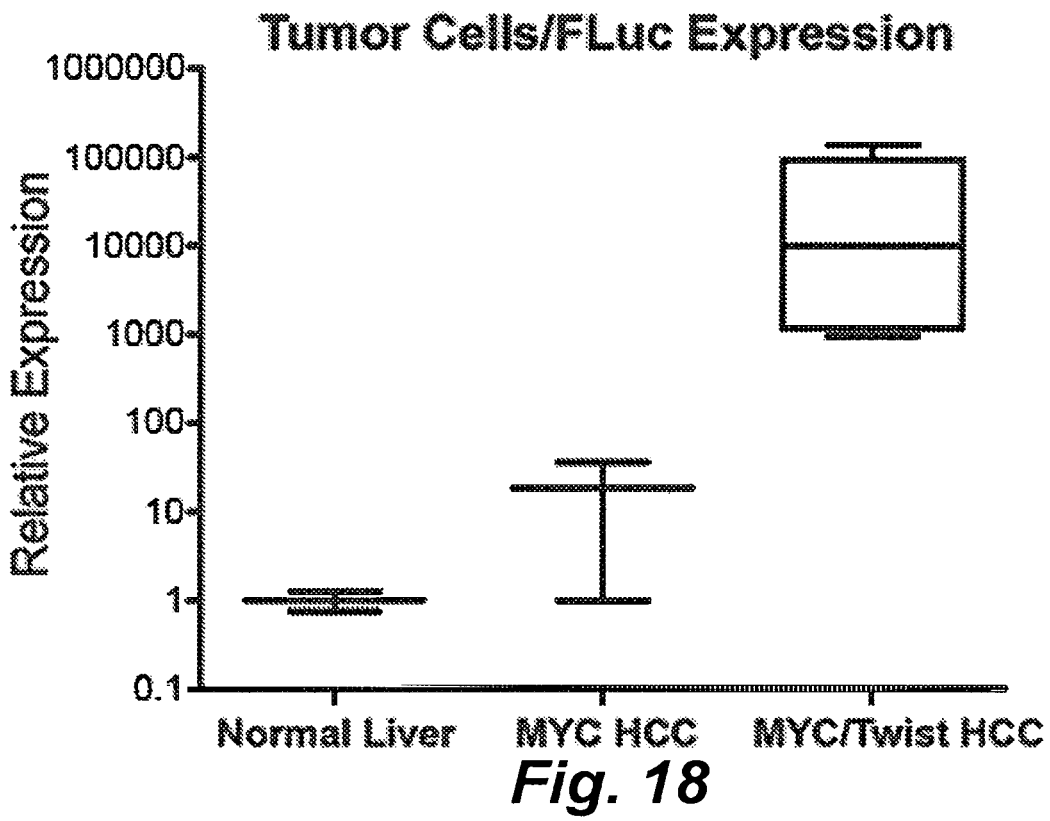
FIGS. 18 and 19 illustrate Twist1 increases the prevalence of circulating tumor cells (CTCs).
Figure 19:
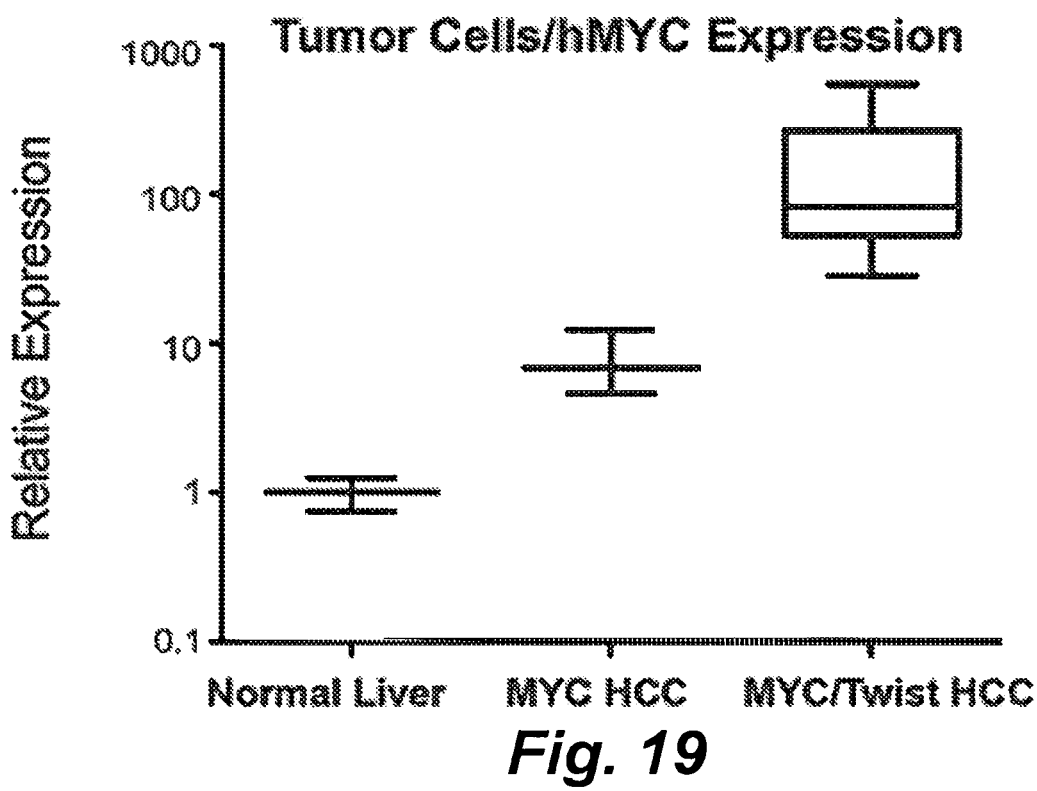

A Z-score analysis was used to compare these new signatures to five previously published gene signatures that have been reported to be prognostic of HCC metastasis and survival (Coulouarn et al., (2009) Oncogene 28: 3526-3536; Coulouarn et al., (2008) Hepatology 47: 2059-2067; Kaposi-Novak et al., (2006) J. Clin. Invest. 116: 1582-1595; Roessler et al., Cancer Res. 70: 10202-10212; Ye et al., (2003) Nat. Med. 9: 416-423) (Table 2, and FIGS. 18 and 19). The MYC/Twist1 HCC+MET signature performed as well or better than the previously defined human HCC metastasis signatures (Coulouarn et al., (2008) Hepatology 47: 2059-2067) at survival prognostication in human HCC cohorts.

Expression of genes in the MYC/Twist1 HCC+MET murine signature stratifying survival of patients with human HCC was investigated. For this analysis it was necessary to utilize individual datasets because the periods of follow-up and survival criteria precluded stratifying all cohorts together. Kaplan-Meier analysis showed that patients with higher expression of the MYC/Twist1 HCC+MET signature genes of the disclosure had worse overall survival than patients with lower expression of signature genes in a previously published cohort of 91 HCC samples (Lee et al., (2004) Nat. Genet. 36: 1306-1311).

Figure 6A:
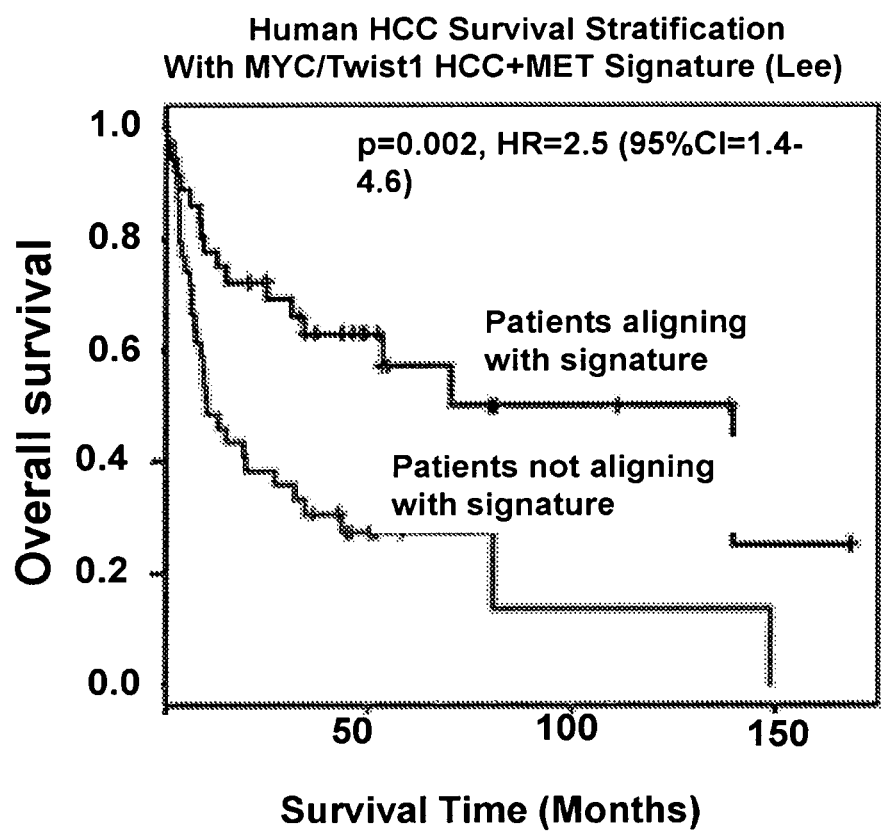
FIGS. 6A and 6B are a pair of graphs illustrating that signatures shown in FIG. 5 were split into up-regulated (_UP) or down-regulated (_DOWN) genes and used to perform a survival analysis in a human HCC cohort in which gene expression was correlated to clinical outcome. MYC/Twist1 HCC+MET_UP genes were associated with poor overall survival in HCC patients (GSE1898; Kaplan-Meier left curve, log-rank test, p=0.002). This finding was validated in an independent human HCC cohort, which showed similar poor prognosis for MYC/Twist1 HCC+MET_UP aligning patients (GSE14520; Kaplan-Meier curve right, log-rank test, p=0.0001).
Figure 6B:
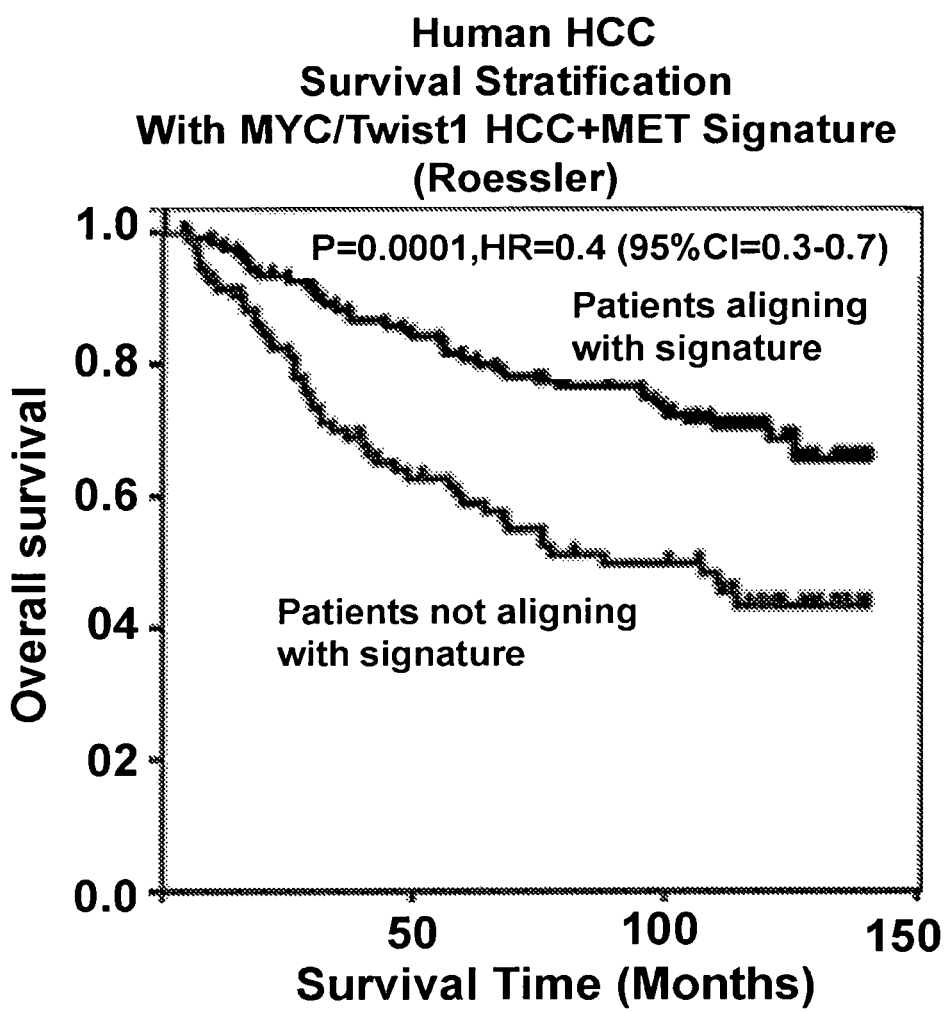
Figure 6C:
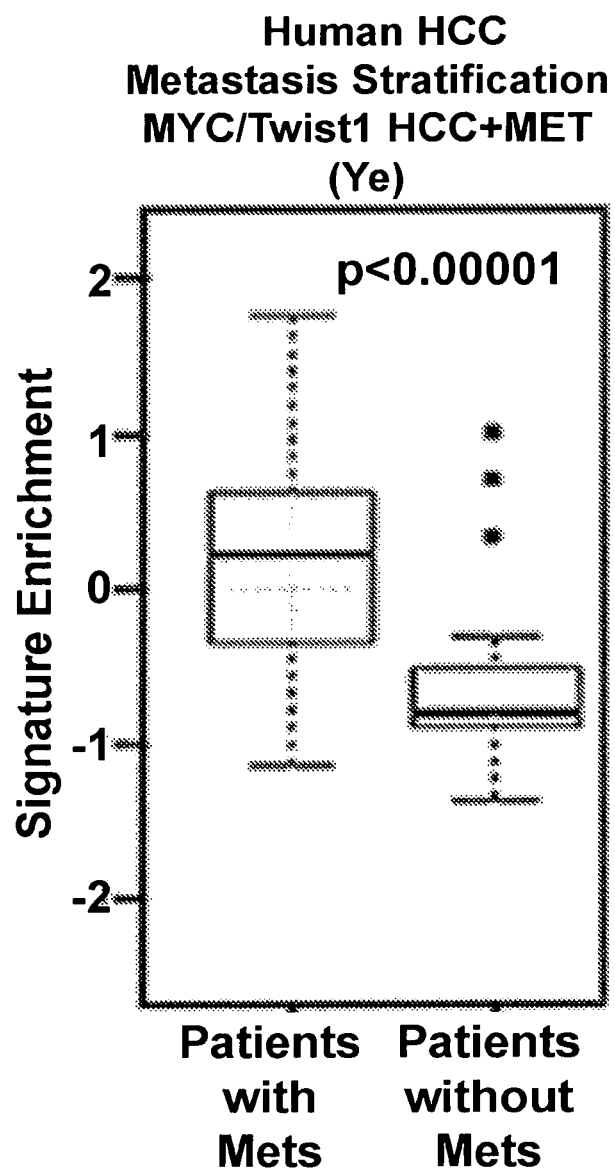
Figure 20:
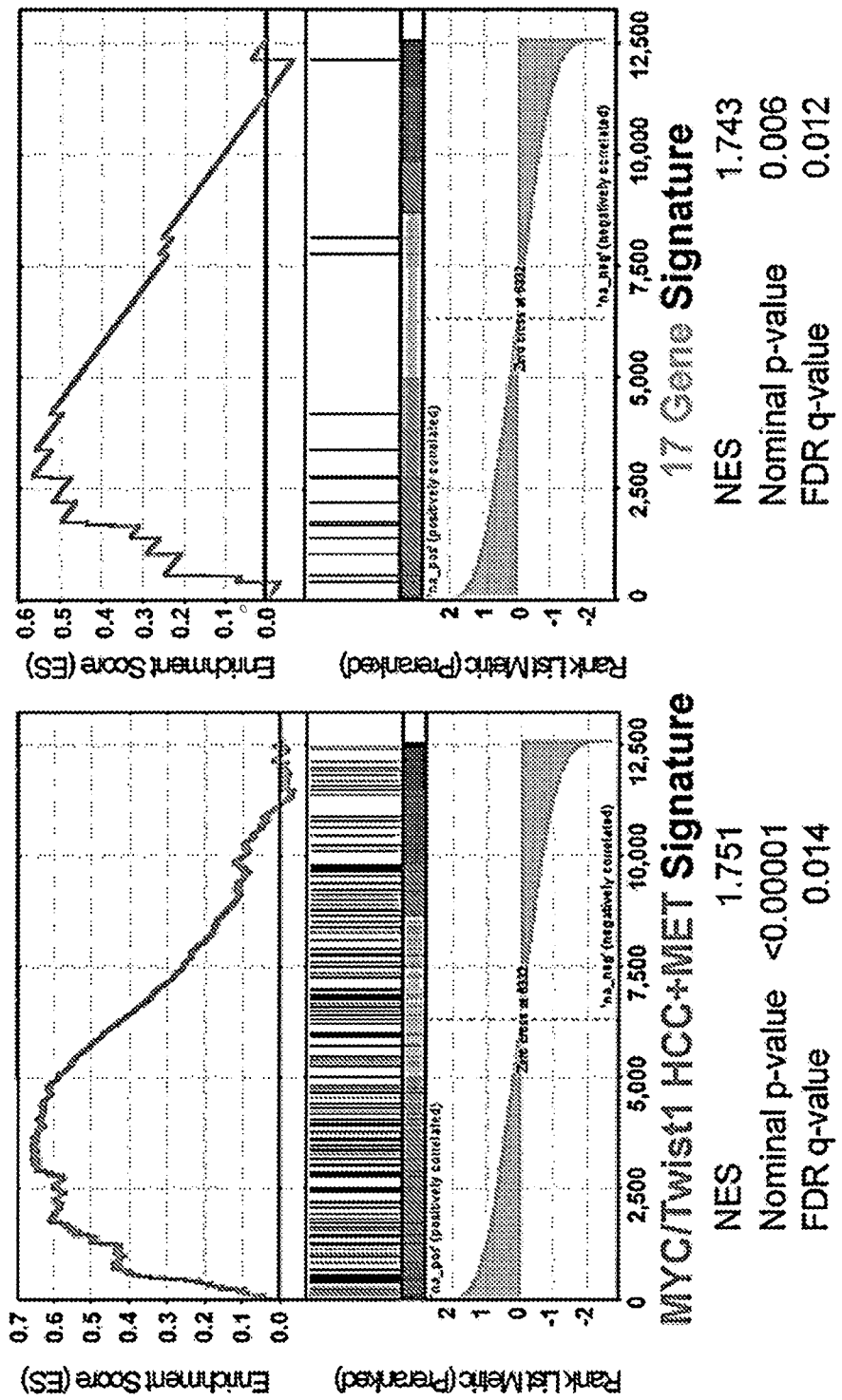
FIG. 20 illustrates a pair of GSEA pre-rank enrichment plots of human HCC Z-score survival analysis for best murine HCC model signature and best overall murine and human comparison signatures. Enrichment plots graphically show how the genes from MYC/Twist1 HCC+MET (best murine model signature) and 17-gene signature (best overlapping signature between murine and human HCC) are enriched within the positive Z-score range within the human HCC database. Enrichment in the positive Z-score spectrum indicates that these genes are associated with poor patient prognosis. This is also reflected in the cumulative NESs for MYC/Twist1 HCC+MET and 17-gene signature of 1.751 and 1.743, respectively. Both signatures achieve statistical significance via p-value (p<0.00001 and p=0.006, respectively) and FDR value (q=0.014 and q=0.012, respectively).
Figures 21A, 21B:
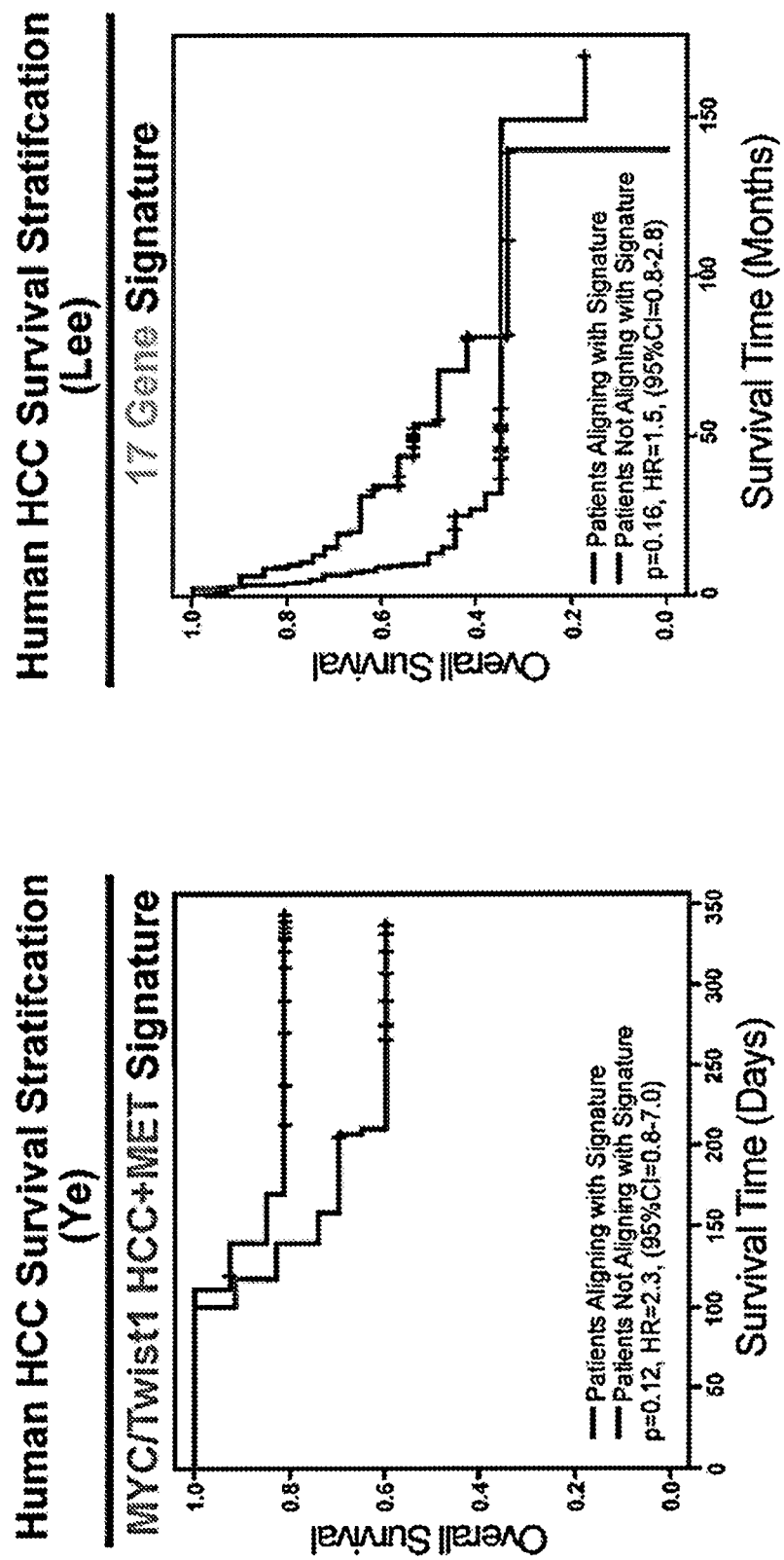
FIGS. 21A and 21B illustrate independent human HCC cohorts validating mouse tumor-derived signatures correlate with poor survival.
Figure 22:
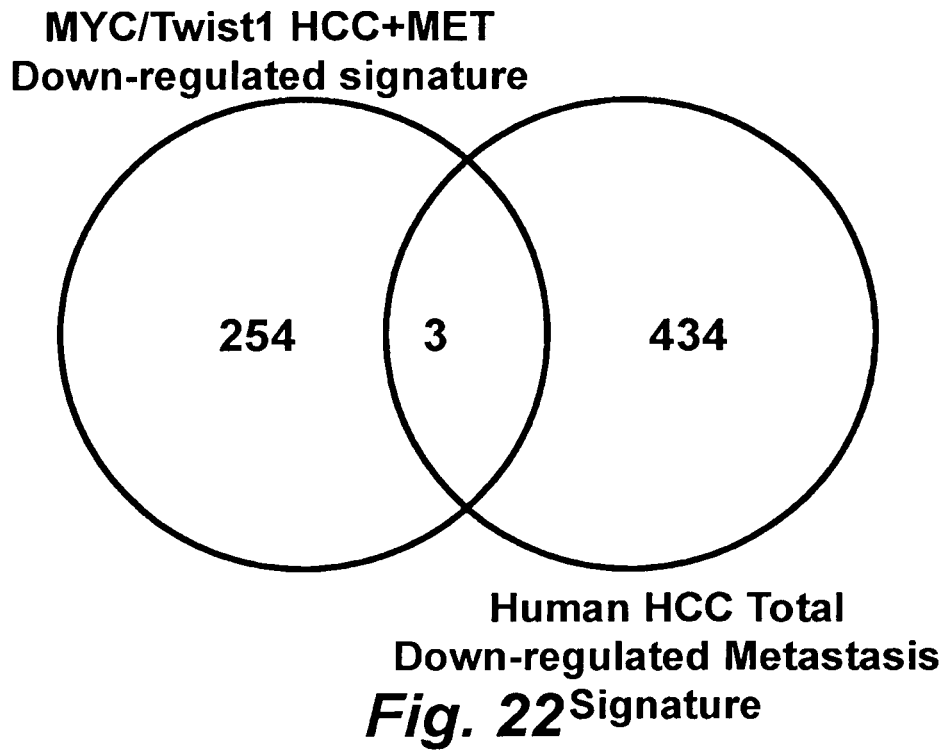
FIG. 22 shows a Venn diagram of the comparison of genes between the mouse MYC/Twist1 HCC+MET_DOWN signature and a compilation of existing human HCC metastasis signatures (Human HCC Down-regulated Metastasis Signature) that revealed 3 down-regulated genes that overlap between mouse and human HCC metastasis signatures.
Figure 23:
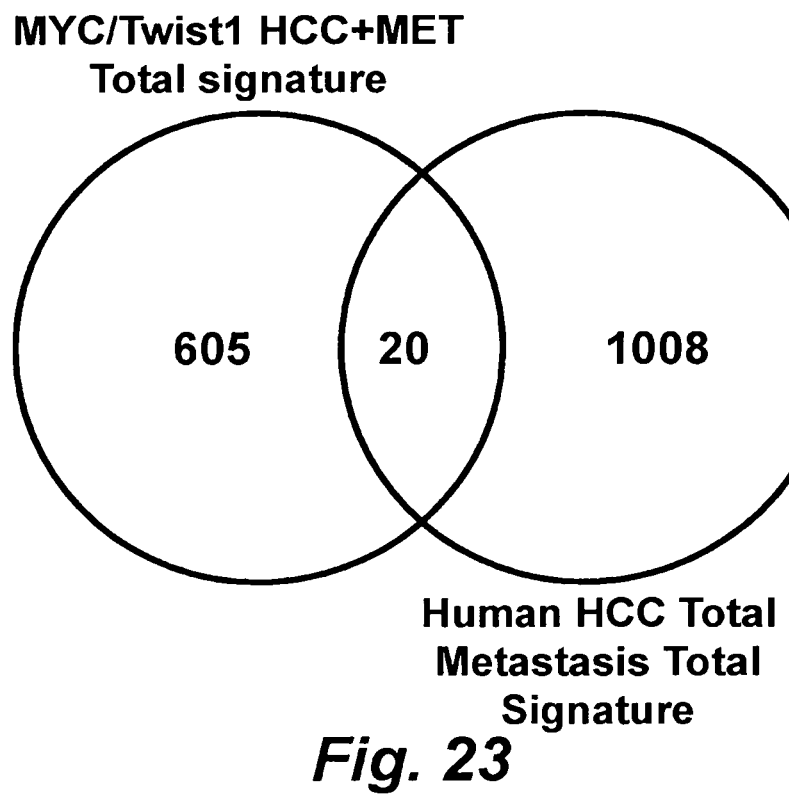
FIG. 23 shows a Venn diagram of the comparison of genes between the mouse MYC/Twist1 HCC+Total signature and a compilation of existing human HCC metastasis signatures (Human HCC Total Metastasis Signature) that revealed 20 differentially regulated genes that overlap between mouse and human HCC metastasis signatures.
Figure 24B:
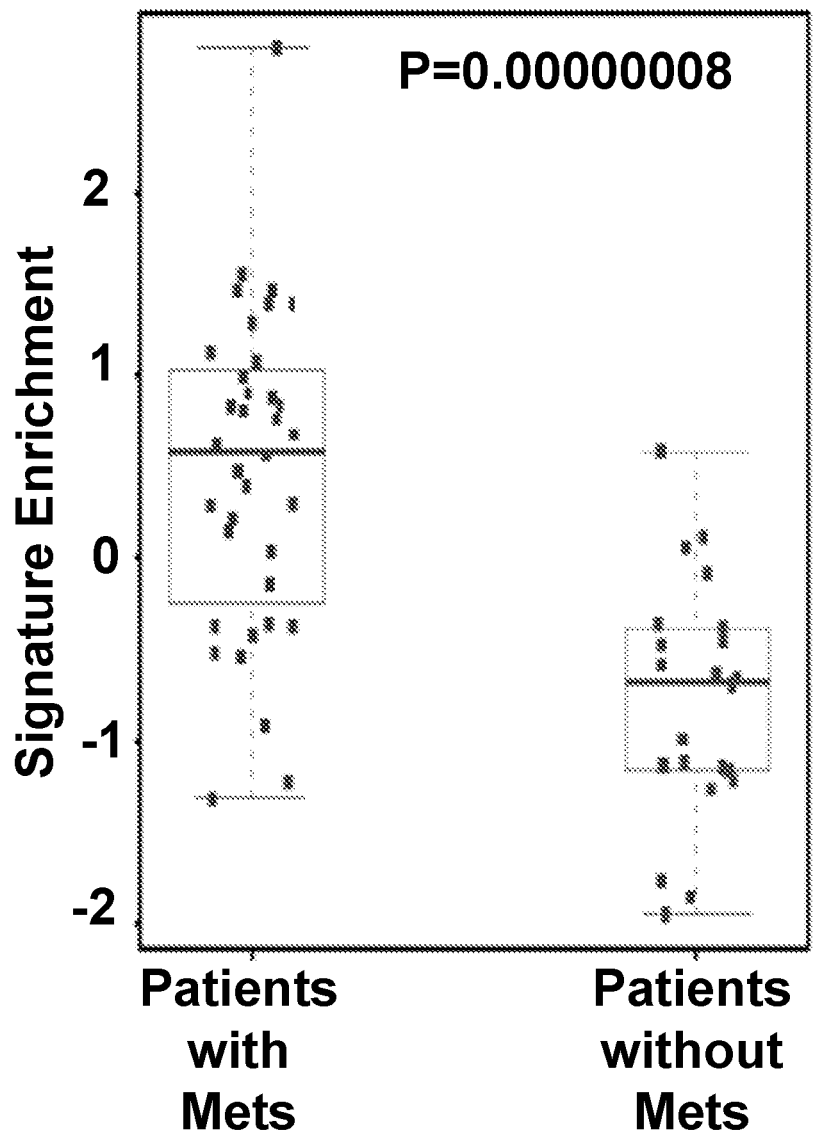
FIG. 24B is a graphical box plot demonstrating stratification of human HCC cohorts based on presence of metastases using the 20-gene signature (GSE364) (t-test of the means, p<0.00001).
Figure 24C:
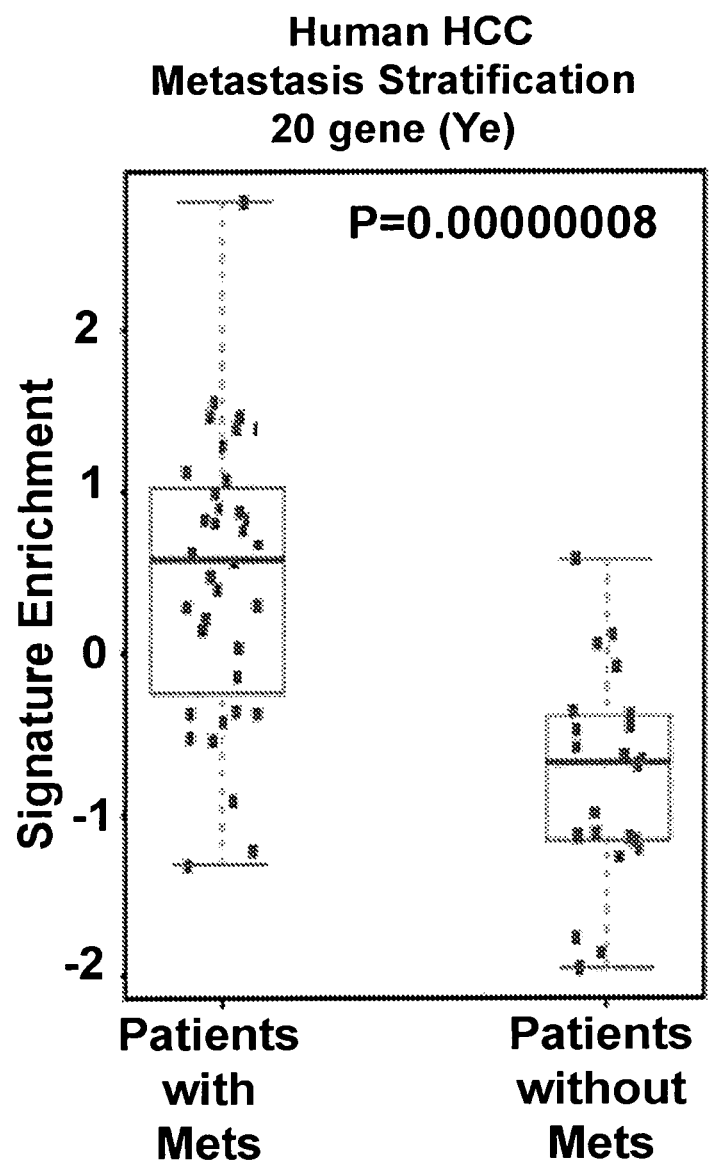
FIG. 24A shows a pair of graphs illustrating that the 20-gene signature was prognostic of poor overall survival in human HCC patients (GSE364; Kaplan-Meier left curve; log-rank test, p=0.004). This finding was validated in an independent data set of human HCC patients, which showed similar poor prognosis for patients aligning with the 20 Gene Signature (GSE14520; Kaplan-Meier right curve; log-rank test, p=0.0012).
Figure 25:
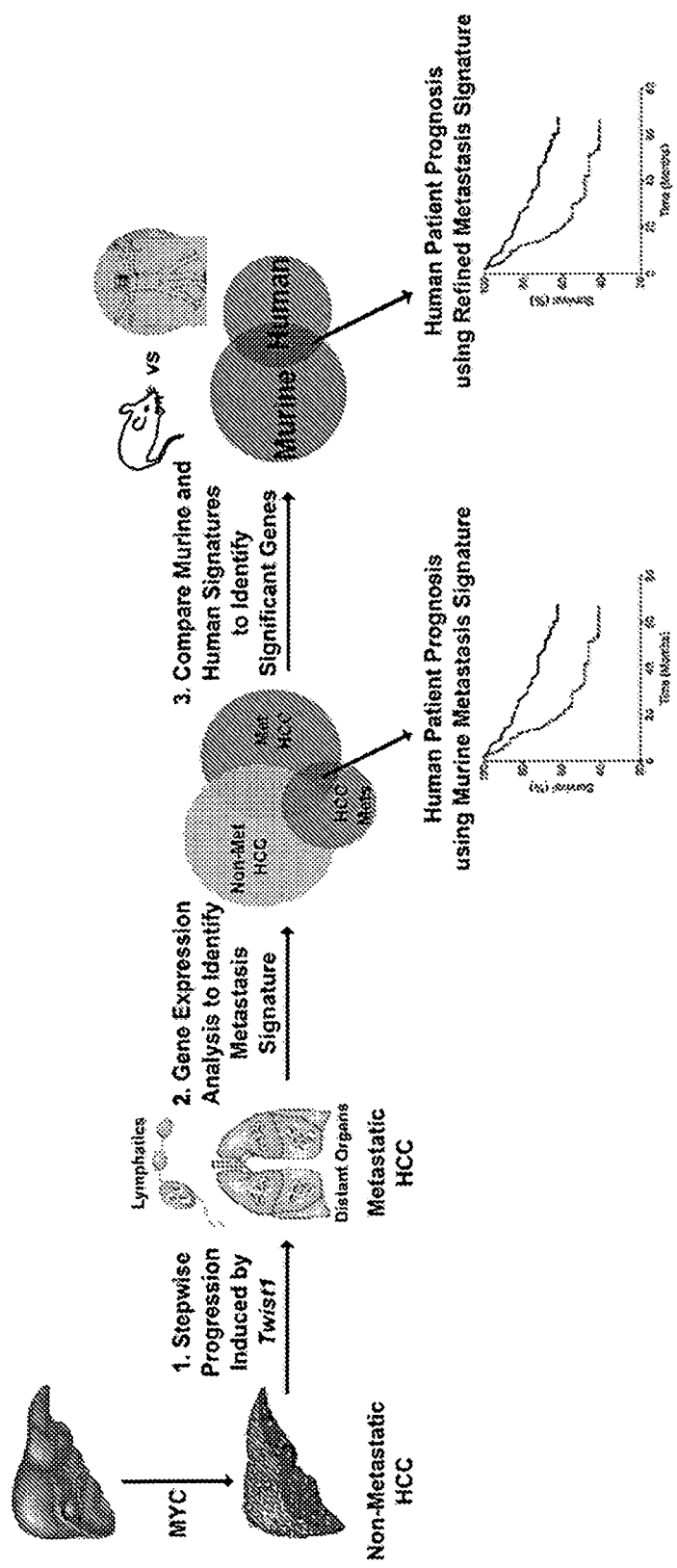
FIG. 25 is a schema illustrating identifying a Gene Signature Prognostic for Outcome in Human Hepatocellular Carcinoma.

Median overall survival of high MYC/Twist1 HCC+MET signature patients was 10 months, versus 70 months median survival of low-signature patients (FIGS. 6A and 6B; log-rank p=0.002; FIG. 20; Table 4). Kaplan-Meier analysis validated that the 17 gene-murine signature was highly predictive of poor patient prognosis in an independent cohort of 386 patients (Roessler et al., Cancer Res. 70: 10202-10212), median overall survival of high MYC/Twist1 HCC+MET signature patients was 42.2 months versus an undefined (not-reached) median survival for non-signature aligning patients (FIG. 6B; log-rank p=0.0001). Importantly, using a third, independent human HCC cohort (Ye et al., (2003) Nat. Med. 9: 416-423), it was determined that the murine MYC/Twist1 HCC+MET signature could predict the incidence of metastasis in human HCC based on expression profiles of the primary tumors (FIG. 6C, t-test of means, p<0.00001). Accordingly, from an analysis of the gene expression changes induced by Twist1 alone in an in vivo transgenic mouse model a signature has been produced that predicts metastasis and overall survival in human patients with HCC.

Figure 7:
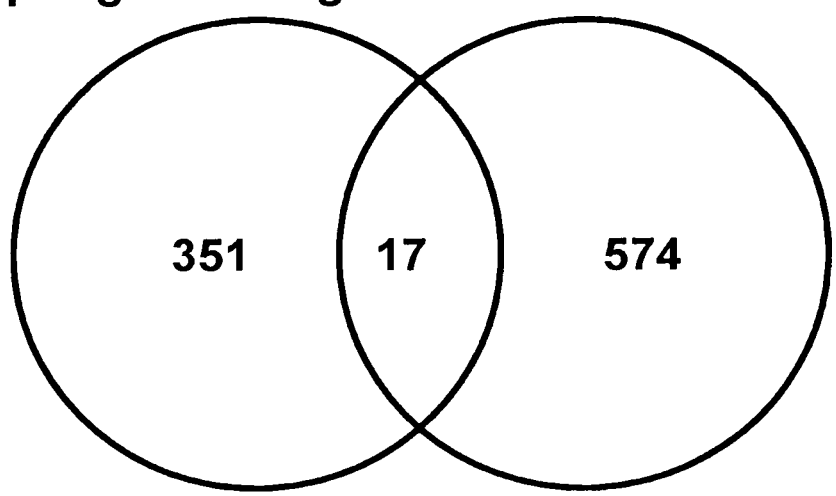
FIGS. 7 and 8A-8C illustrate a comparative analysis of mouse and human gene expression that identified a 17-gene signature that is highly prognostic for human HCC invasion and survival.
Figure 8A:
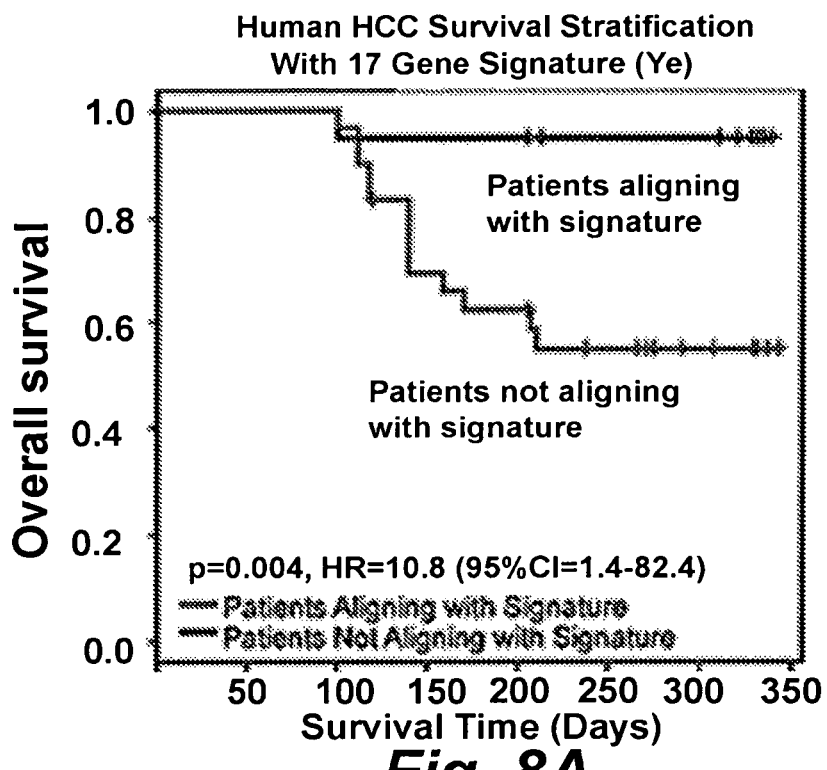
Figure 8B:
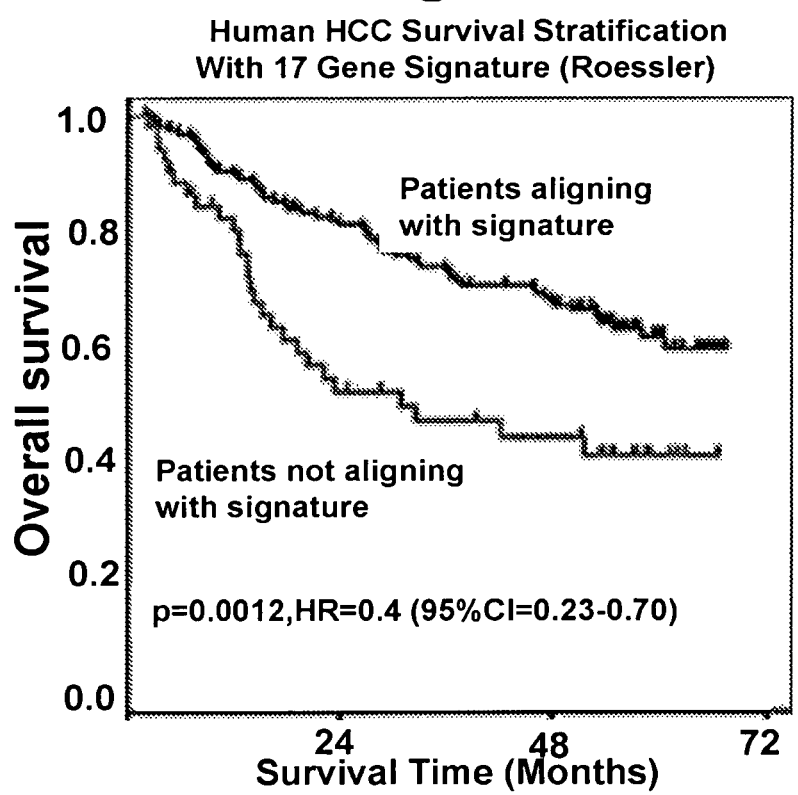
Figure 8C:
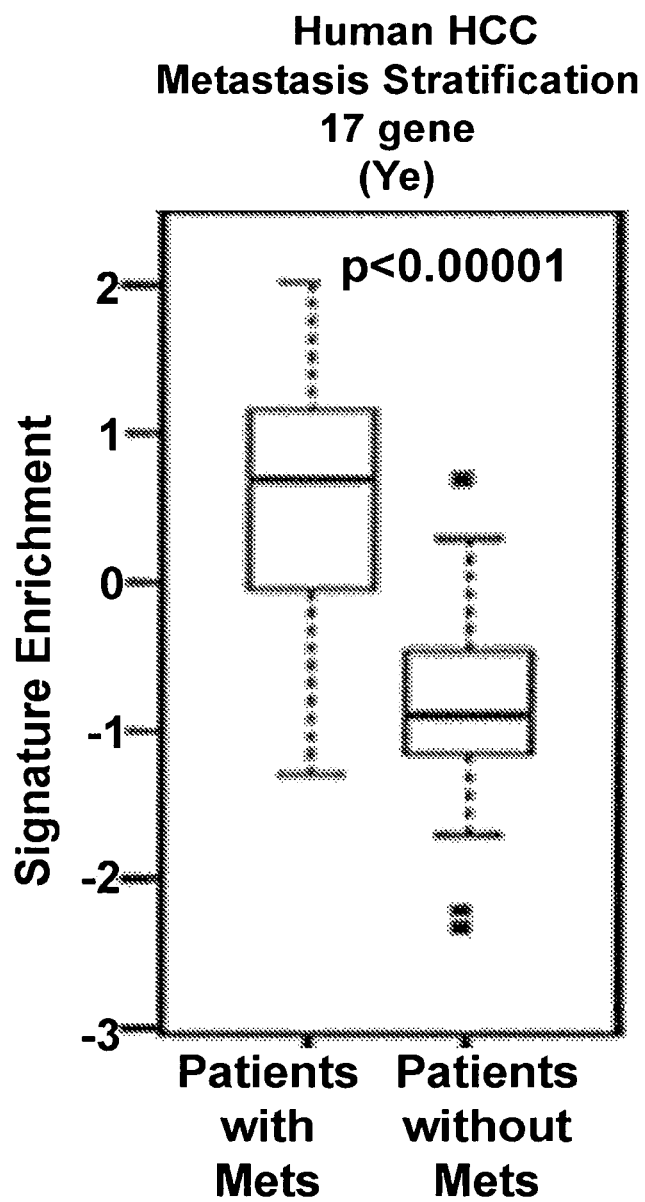
Figure 9B:
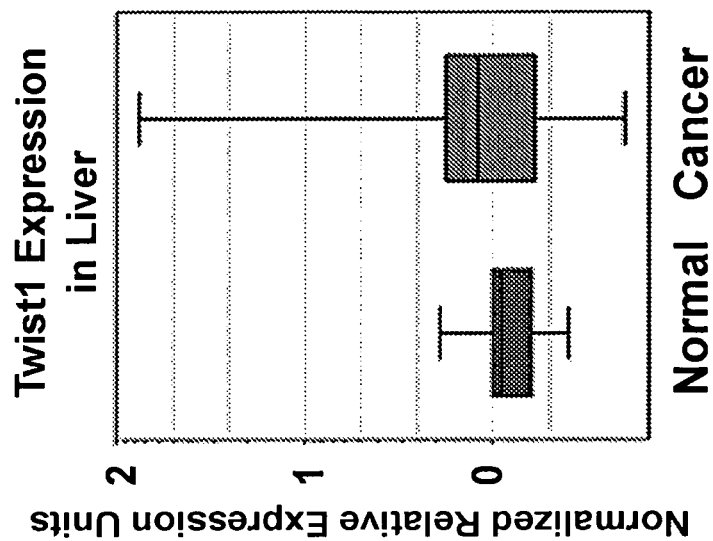
FIGS. 9A and 9B illustrate that Twist1 is expressed in human HCC.
Figure 9A:
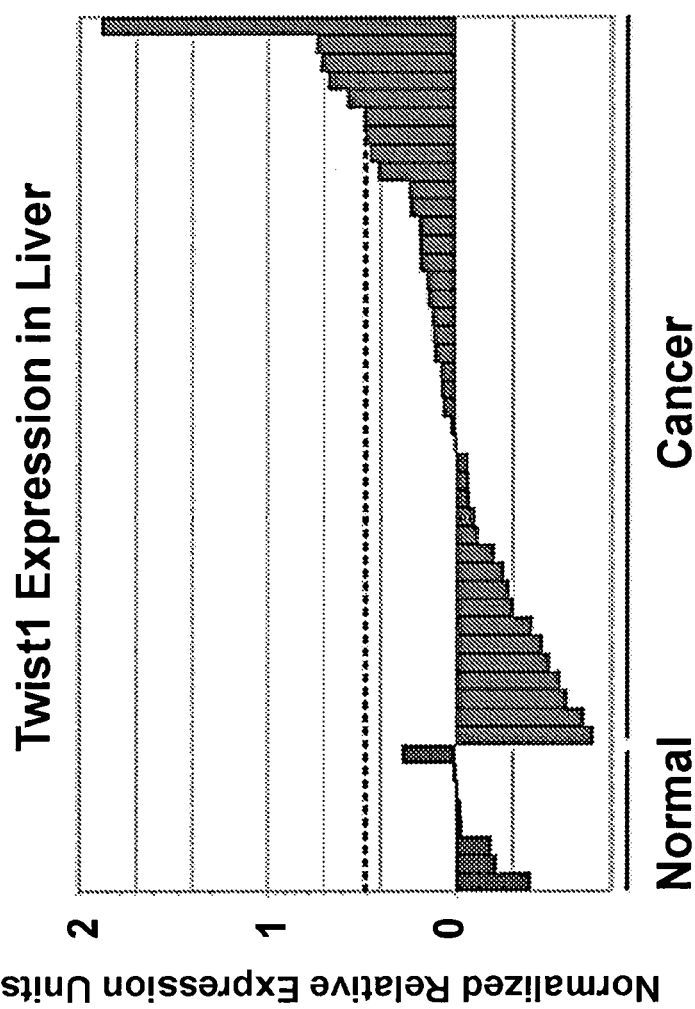
Figure 10:
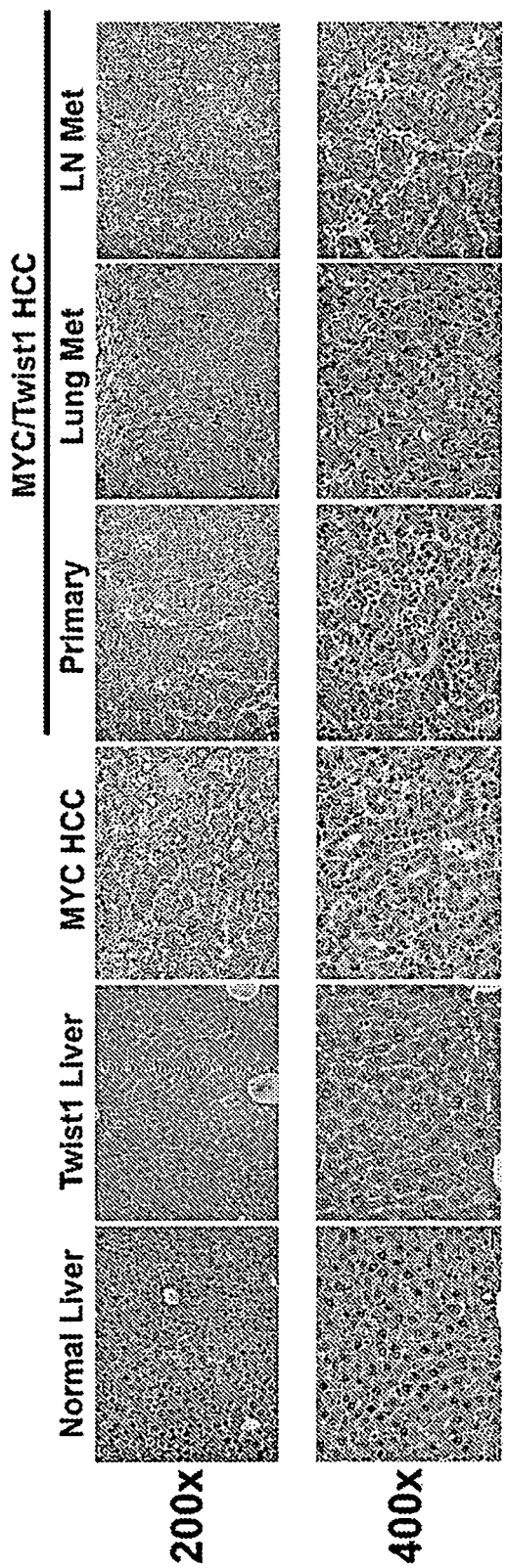
FIG. 10 is a series of digital images illustrating that Twist1 facilitates metastasis in MYC-induced HCC, but does not affect liver histology when expressed alone. H&E of normal versus Twist1-overexpressing liver showed no noticeable difference in tissue histology. MYC HCC primarily demonstrated poorly differentiated, adenoid histology. MYC/Twist1 primary HCC demonstrated adenoid histology similar to MYC HCC as well as trabecular histology. MYC/Twist1 HCC metastases to the lung and lymph nodes (LN) and showed trabecular and solid histology, respectively. All metastases were determined histologically to be HCC in origin.
Figure 11:
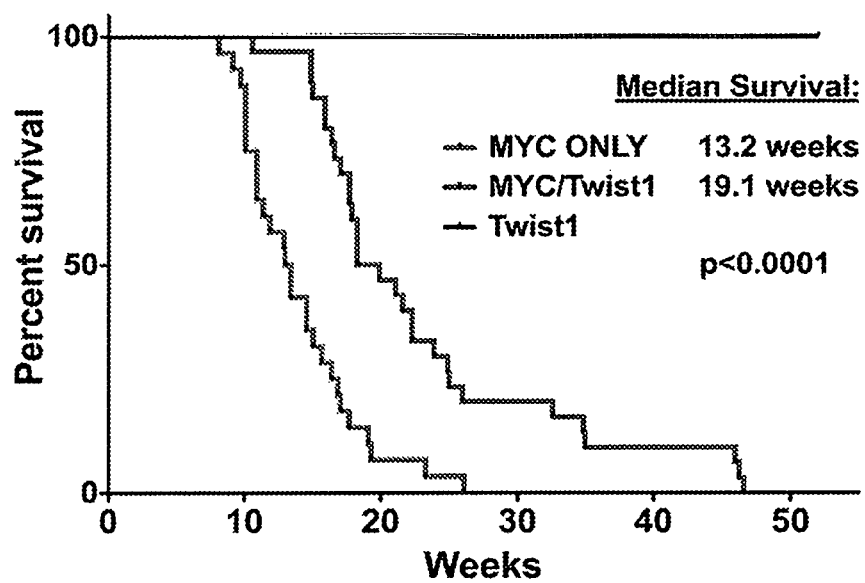
FIG. 11 is a graph showing that Twist1 increases survival in MYC-induced HCC. A Kaplan-Meier survival curve is shown for MYC, MYC/Twist1, and Twist1 mice. MYC mice (n=30) succumbed to HCC with a median time of 13.2 weeks. MYC/Twist1 mice (n=30) succumbed to HCC with a median time of 19.1 weeks (p<0.0001, log-rank test). Twist1 mice (n=15) never succumbed to disease and were healthy up to 18 months after transgene activation.
Figure 12:
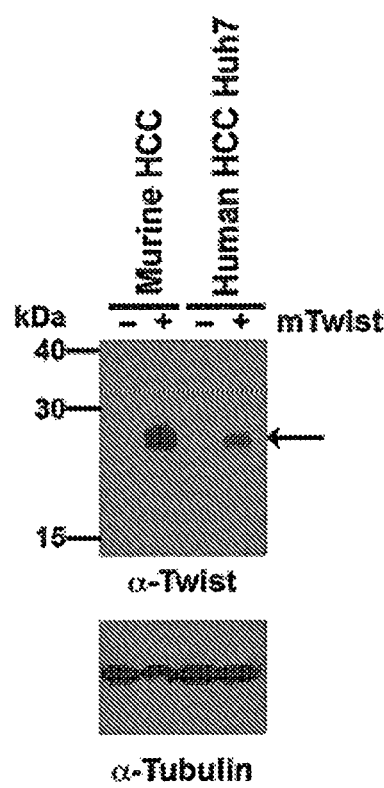
Figure 13:
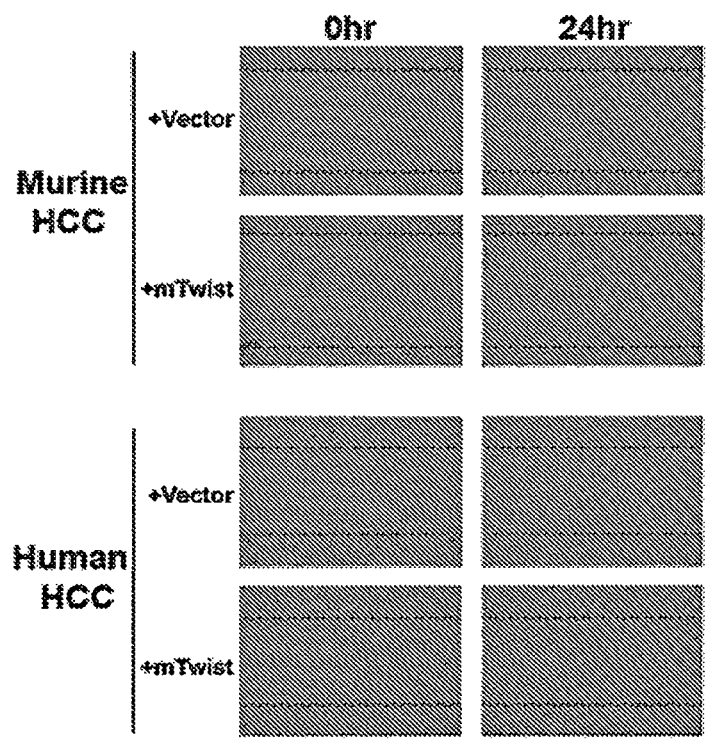

Identification of a 12-Gene Signature that is Prognostic of Human HCC Metastasis and Overall Survival To identify the most critical genes within our MYC/Twist1 HCC+MET signature that are associated with malignant progression of HCC, the up-regulated genes in that signature were compared to the up-regulated genes encompassed in the five previously characterized human HCC metastasis signatures to which the murine signature of the present disclosure had been previously compared (Coulouarn et al., (2009) Oncogene 28: 3526-3536; Coulouarn et al., (2008) *Hepatology* 47: 2059-2067; Kaposi-Novak et al., (2006) *J. Clin. Invest.* 116: 1582-1595; Roessler et al., *Cancer Res.* 70: 10202-10212; Ye et al., (2003) *Nat. Med.* 9: 416-423) (hereafter these genes are referred to as the Human HCC Total Metastasis Up-regulated Signature). This comparison was meant to pinpoint any genes within the highly predictive mouse signature of the disclosure that were so crucial to HCC metastasis that they were up-regulated in at least one other metastasis signature driven by a different genetic aberration. When the MYC/Twist1 HCC+MET signature gene list was compared to the Human HCC Total Metastasis Up-regulated Signature gene list, 12 such regulated genes were revealed (FIGS. 7, 18, and 19; Table 2). These regulated genes were hbegf, aldoa, arid3a, lgals1, hbegf, afp, slc35d2, cyp2c9, cyp4v2, limk2, acp2, lgals3, and ndrg1 comprise the gene signature of the present disclosure.

The set of 12 identified genes were examined for their ability to prognosticate patient outcome and disease progression. From a Z-score survival analysis, the 12-gene metastasis signature had greater prognostic power for HCC overall survival than did other individual or compiled HCC signatures from the mouse transgenic model of the disclosure or previously reported (Table 2; p=0.0079, NES=1.774, FDR=0.0125).

The prognostic capability of our 12-gene signature was examined for overall survival/clinical outcome in human HCC through both univariate and multivariate Cox regression analyses in comparison to, and in combination with, other clinical staging methods including Cancer of the Liver Italian Program (CLIP), Classification of Malignant Tumors (TNM), and Barcelona Clinic Liver Cancer (BCLC) (Pons et al., (2005) *HPB (Oxford)* 7: 35-41).

The present disclosure provides a 12-gene signature, aldoa, arid3a, lgals1, hbegf, afp, slc35d2, cyp2c9, cyp4v2, limk2, acp2, lgals3, and ndrg1, as disclosed in Example 17, and the uses thereof that has been found to further predict the prognostic outcome of survival of a patient having HCC. The 12-gene signature also was able to predict metastatic capability of primary human. Thus, the 12-gene signature has the ability to predict disease progression in the form of metastasis and overall survival in human patients. It is contemplated, therefore, that the production of a differential gene expression profile using the 12-gene signature of the disclosure, can be presented as a report generated by such as a computer-based system that indicates to a physician or other person attending to the subject patient the metastasis status of the carcinoma, and providing a prediction of the prognostic outcome of the disease in the patient. With this information available, a physician can introduce or adjust a treatment administered to the patient having the hepatocellular carcinoma according to the metastatic status of the carcinoma.

Accordingly, the conditional transgenic mouse models of HCC show that expression of Twist1 alone can facilitate autochthonous tumor intravasation, as measured by CTCs, and markedly increased metastasis, as demonstrated by gross and microscopic pathology; and induce a gene expression program that predicts invasion and clinical outcome in human patients with HCC. A direct comparison of gene expression in tumors in non-metastatic versus metastatic HCC caused by Twist1 was examined, which identified a 12-gene signature highly predictive of human HCC metastasis and clinical outcome. This gene signature is equally or more predictive than other gene signatures that include more than 200 genes (Coulouarn et al., (2009) *Oncogene* 28: 3526-3536; Coulouarn et al., (2008) *Hepatology* 47: 2059-2067; Kaposi-Novak et al., (2006) *J. Clin. Invest.* 116: 1582-1595; Roessler et al., *Cancer Res.* 70: 10202-10212; Ye et al., (2003) *Nat. Med.* 9: 416-423). This approach was complimentary to analyses of primary human tumor tissues or human-derived cell lines (Barrier et al., (2006) *J. Clinical Oncol.* 24: 4685-4691; Bos et al., (2009) *Nature* 459: 1005-1009; Bueno-de-Mesquita et al., (2007) *Lancet Oncol.* 8: 1079-108; Kang et al., (2003) *Cancer Cell* 3: 537-549; Paik et al., (2004) *New Eng. J. Med.* 351: 2817-2826; Salazar et al., (2011) *J. Clin. Oncol.* 29: 17-24; Wan et al., (2010) *PLoS One* 5, e12222), but which do not readily enable an in situ analysis of the stepwise changes in malignant progression conferred by the introduction of a single oncogene. The results generally illustrate how a comparative genomic analysis of stepwise transgenic mouse models of malignant progression can be used to identify prognostic gene signatures.

Twist1 expression alone was sufficient to induce metastasis and that this was associated with specific changes in gene expression that are highly predictive of HCC invasion, metastasis, and overall survival in humans. The 12-gene list is shorter than previously identified signatures, and therefore is more generally amenable to measurement in a clinical setting from biopsy material of patients to assist in prognostication. Importantly, this gene signature was shown to be independently prognostic by multivariate analysis when compared to current clinical staging systems, indicating that these genes in concert with conventional HCC clinical and pathological staging can further predict clinical outcome.

While not wishing to be bound by any one theory, Twist1 has been suggested to contribute to metastasis through the induction of EMT. Twist1 alone is sufficient to induce metastasis in primary MYC-induced HCC. Twist1 also markedly increased the ability of HCC to exhibit hematogenous dissemination, as measured by CTCs. However, Twist1 was not associated with changes in the gene expression of primary tumors that have been associated with EMT, as measured by IHC or qPCR analysis. There is also evidence for EMT in metastases. Accordingly, Twist1 is necessary for, but alone may not be sufficient, for the induction of EMT during tumor progression, as previously suggested (Eckert et al., (2011) *Cancer Cell* 19: 372-386; Casas et al., (2011) *Cancer Res.* 71: 245-254).

Amongst the genes in the 12-gene signature of the present disclosure, have been genes reported to be associated with metastasis of: breast cancer (hbegf, and lglals1) (Bos et al., (2009) *Nature* 459: 1005-1009; Demydenko & Berest (2009) *Exp. Oncol.* 31: 74-79; colorectal cancer (lgals1) (Demydenko & Berest (2009) *Exp. Oncol.* 31: 74-79); and lung cancer (aldoa) (Lin et al., (2010) *Euro. Resp. J. Clin. Resp. Physiol*). Only lgals1, afp, and ndrg1 have been previously implicated in the mechanism of HCC invasion and metastasis (Spano et al., (2010) *Mol. Med.* 16: 102-115; Zhou et al., *World J. Gastroenterol.* 12: 1175-1181; Akiba et al., (2008) *Oncol. Rep.* 20: 1329-1335). Although increased ndrg1 is associated with HCC metastasis, it previously has been shown to suppress metastasis in multiple other tissues (Kovacevic & Richardson (2006) *Carcinogenesis* 27: 2355-2366), suggesting tissue-dependent effects of Twist1 expression.

The suppression of both MYC and Twist1 expression resulting in a sustained regression of both primary and metastatic HCC. Invasive HCC may be treatable through the inactivation of both these oncogenes. Twist1 may provide an effective target to prevent metastasis as well as for the therapy of advanced HCC. In particular, the experimental approach according to this disclosure demonstrates that transgenic mouse models of stepwise malignant progression can be employed through a comparative genomic analysis to yield short gene signatures useful as a tractable approach to predict clinical outcome in human patients.

One aspect of the disclosure encompasses embodiments of a method for determining whether a hepatocellular carcinoma tissue of a patient has a differential gene expression signature of a metastatic hepatocellular carcinoma tissue, the method comprising the steps: (a) obtaining a first gene expression signature from a first tissue sample from a first subject by determining the levels of expression of the genes aldoa, arid3a, lgals1, hbegf, afp, slc35d2, cyp2c9, cyp4v2, limk2, acp2, lgals3, and ndrg1 in the first tissue sample, wherein the first tissue sample is a hepatocellular carcinoma; (b) obtaining a gene expression signature from a second tissue sample from a second subject by determining the levels of expression of the genes aldoa, arid3a, lgals1, hbegf, afp, slc35d2, cyp2c9, cyp4v2, limk2, acp2, lgals3, and ndrg1 in the second tissue sample, wherein the second tissue sample is from a subject not having an hepatocellular carcinoma or suspected of not having developed a metastatic hepatocellular carcinoma; wherein step (a) and step (b) each independently consists of the steps: (i) isolating RNA from the tissue sample and generating cDNA copies therefrom; (ii) quantitatively measuring the RNA levels expressed by the genes aldoa, arid3a, lgals1, hbegf, afp, slc35d2, cyp2c9, cyp4v2, limk2, acp2, lgals3, and ndrg1 by a Reverse Transcription Polymerase Chain Reaction (RT-PCR) assay, wherein the RT-PCR uses the PCR primer pairs: aldoa-specific SEQ ID NOs: 1 and 2; arid3a-specific SEQ ID NOs: 3 and 4; lgals1-specific SEQ ID NOs: 5 and 6; hbegf-specific SEQ ID NOs: 7 and 8; afp-specific SEQ ID NOs: 9 and 10; slc35d2-specific SEQ ID NOs: 11 and 12; cyp2c9-specific SEQ ID NOs: 13 and 14; cyp4v2-specific SEQ ID NOs: 15 and 16; limk2-specific SEQ ID NOs: 17 and 18; acp2-specific SEQ ID NOs: 19 and 20; lgals3-specific SEQ ID NOs: 21 and 22; and ndrg1-specific SEQ ID NOs: 23 and 24; and further uses the chemically-modified probes: aldoa-specific SEQ ID NO: 25; arid3a-specific SEQ ID NO: 26; lgals1-specific SEQ ID NO: 27; hbegf-specific SEQ ID NO: 28; afp-specific SEQ ID NO: 29; slc35d2-specific SEQ ID NO: 30; cyp2c9-specific SEQ ID NO: 31; cyp4v2-specific SEQ ID NO: 32; limk2-specific SEQ ID NO: 33; acp2-specific SEQ ID NO: 34; lgals3-specific SEQ ID NO: 35; and ndrg1-specific SEQ ID NO: 36, wherein each of the chemically-modified probes has a terminally attached fluorescent moiety and a terminally attached quenching moiety, and wherein the expression level of each gene is quantifiably measured by measuring the intensity of fluorescence from each of said gene-specific chemically-modified probes.

In some embodiments of this aspect of the disclosure, the method can further comprise the steps of: (c) comparing the levels of gene expression of the first and the second gene expression signatures, wherein the relative levels of gene expression indicate the presence or absence of metastatic hepatocellular carcinoma cells in the first subject suspected of having a metastatic hepatocellular carcinoma; and (d) generating a report indicating the metastatic status of a hepatocellular carcinoma of the patient, wherein: (i) if the expression of the genes aldoa, arid3a, lgals1, hbegf, afp, slc35d2 of the first tissue sample is elevated compared to the expression level of the same genes of the second tissue sample, there is a reduced likelihood of survival of the first subject development from the carcinoma in the patient; and (ii) if the expression of the genes cyp2c9, cyp4v2, limk2, acp2, lgals3, and ndrg1 in the first tissue sample is elevated compared to the expression level of the same genes of the second tissue sample, said levels indicate an extended period of the first subject survival.

In some embodiments of this aspect of the disclosure, the first and the second tissue samples are from the same subject and isolated therefrom at successive time-points.

In some embodiments of this aspect of the disclosure, the terminally attached fluorescent moiety is attached to the 3' terminus of a probe and the terminally attached quenching moiety is attached to the 5' terminus of a probe.

In some embodiments of this aspect of the disclosure, the terminally attached fluorescent moiety is attached to the 5' terminus of a probe and the terminally attached quenching moiety is attached to the 3' terminus of a probe.

In some embodiments of this aspect of the disclosure, the products of the RT-PCR steps can be hybridized to complimentary nucleotide sequences arrayed on a substrate and detected thereon.

Accordingly, in embodiments of this aspect of the disclosure, the method for determining whether a hepatocellular carcinoma tissue of a patient has a differential gene expression signature of a metastatic hepatocellular carcinoma tissue can comprise any of the preceding embodiments.

Another aspect of the disclosure encompasses embodiments of a method of determining a mode of treatment of a hepatocellular carcinoma of a patient, comprising: (a) obtaining a first gene expression signature from a first tissue sample from a first subject by determining the levels of expression of the genes aldoa, arid3a, lgals1, hbegf, afp, slc35d2, cyp2c9, cyp4v2, limk2, acp2, lgals3, and ndrg1 in the first tissue sample, wherein the first tissue sample is a hepatocellular carcinoma; (b) obtaining a gene expression signature from a second tissue sample from a second subject by determining the levels of expression of the genes aldoa, arid3a, lgals1, hbegf, afp, slc35d2, cyp2c9, cyp4v2, limk2, acp2, lgals3, and ndrg1 in the second tissue sample, wherein the second tissue sample is from a subject not having an hepatocellular carcinoma or suspected of not having developed a metastatic hepatocellular carcinoma; wherein step (a) and step (b) each independently consists of the steps: (i) isolating RNA from the tissue sample and generating cDNA copies therefrom; (ii) quantitatively measuring the RNA levels expressed by the genes aldoa, arid3a, lgals1, hbegf, afp, slc35d2, cyp2c9, cyp4v2, limk2, acp2, lgals3, and ndrg1 by a Reverse Transcription Polymerase Chain Reaction (RT-PCR) assay, wherein the RT-PCR uses the PCR primer pairs: aldoa-specific SEQ ID NOs: 1 and 2; arid3a-specific SEQ ID NOs: 3 and 4; lgals1-specific SEQ ID NOs: 5 and 6; hbegf-specific SEQ ID NOs: 7 and 8; afp-specific SEQ ID NOs: 9 and 10; slc35d2-specific SEQ ID NOs: 11 and 12; cyp2c9-specific SEQ ID NOs: 13 and 14; cyp4v2-specific SEQ ID NOs: 15 and 16; limk2-specific SEQ ID NOs: 17 and 18; acp2-specific SEQ ID NOs: 19 and 20; lgals3-specific SEQ ID NOs: 21 and 22; and ndrg1-specific SEQ ID NOs: 23 and 24; and further uses the chemically-modified probes: aldoa-specific SEQ ID NO: 25; arid3a-specific SEQ ID NO: 26; lgals1-specific SEQ ID NO: 27; hbegf-specific SEQ ID NO: 28; afp-specific SEQ ID NO: 29; slc35d2-specific SEQ ID NO: 30; cyp2c9-specific SEQ ID NO: 31; cyp4v2-specific SEQ ID NO: 32; limk2-specific SEQ ID NO: 33; acp2-specific SEQ ID NO: 34; lgals3-specific SEQ ID NO: 35; and ndrg1-specific SEQ ID NO: 36, wherein each of the chemically-modified probes has a terminally attached fluorescent moiety and a terminally attached quenching moiety, and wherein the expression level of each gene is quantifiably measured by measuring the intensity of fluorescence from each of said gene-specific chemically-modified probes; (c) comparing the levels of gene expression of the first and the second gene expression signatures, wherein the relative levels of gene expression indicate the presence or absence of metastatic hepatocellular carcinoma cells in the first subject suspected of having a metastatic hepatocellular carcinoma; and (d) generating a report indicating the metastatic status of a hepatocellular carcinoma of the patient, wherein: (i) if the expression of the genes aldoa, arid3a, lgals1, hbegf, afp, slc35d2 of the first tissue sample is elevated compared to the expression level of the same genes of the second tissue sample, there is a reduced likelihood of survival of the first subject development from the carcinoma in the patient; and (ii) if the expression of the genes cyp2c9, cyp4v2, limk2, acp2, lgals3, and ndtg1 in the first tissue sample is elevated compared to the expression level of the same genes of the second tissue sample, said levels indicate an extended period of the first subject survival; and (e) adjusting a mode of treatment of a hepatocellular carcinoma of the patient from whom the first tissue sample was obtained.

In some embodiments of this aspect of the disclosure, the second tissue sample is obtained from a subject not having a hepatocellular carcinoma or suspected of not having developed a metastatic hepatocellular carcinoma.

In some embodiments of this aspect of the disclosure, the first and the second tissue samples are from the same subject and isolated therefrom at successive time-points, thereby indicating the progression of the hepatocellular carcinoma in the patient.

In some embodiments of this aspect of the disclosure, the terminally attached fluorescent moiety is attached to the 3' terminus of a probe and the terminally attached quenching moiety is attached to the 5' terminus of a probe.

In some embodiments of this aspect of the disclosure, the terminally attached fluorescent moiety is attached to the 5' terminus of a probe and the terminally attached quenching moiety is attached to the 3' terminus of a probe.

In some embodiments of this aspect of the disclosure, the products of the RT-PCR steps are hybridized to complimentary nucleotide sequences arrayed on a substrate and detected thereon.

Accordingly, in embodiments of this aspect of the disclosure, the method for determining whether a hepatocellular carcinoma tissue of a patient has a differential gene expression signature of a metastatic hepatocellular carcinoma tissue can comprise any of the preceding embodiments.

Yet another aspect of the disclosure encompasses embodiments of a composition comprising at least one of the PCR primer pairs of the group consisting of: aldoa-specific SEQ ID NOs: 1 and 2; arid3a-specific SEQ ID NOs: 3 and 4; lgals1-specific SEQ ID NOs: 5 and 6; hbegf-specific SEQ ID NOs: 7 and 8; afp-specific SEQ ID NOs: 9 and 10; slc35d2-specific SEQ ID NOs: 11 and 12; cyp2c9-specific SEQ ID NOs: 13 and 14; cyp4v2-specific SEQ ID NOs: 15 and 16; limk2-specific SEQ ID NOs: 17 and 18; acp2-specific SEQ ID NOs: 19 and 20; lgals3-specific SEQ ID NOs: 21 and 22; and ndrg1-specific SEQ ID NOs: 23 and 24.

In some embodiments of this aspect of the disclosure, the composition further comprise at least one of the chemically-modified probes selected from the group consisting of: aldoa-specific SEQ ID NO: 25; arid3a-specific SEQ ID NO: 26; lgals1-specific SEQ ID NO: 27; hbegf-specific SEQ ID NO: 28; afp-specific SEQ ID NO: 29; slc35d2-specific SEQ ID NO: 30; cyp2c9-specific SEQ ID NO: 31; cyp4v2-specific SEQ ID NO: 32; limk2-specific SEQ ID NO: 33; acp2-specific SEQ ID NO: 34; lgals3-specific SEQ ID NO: 35; and ndrg1-specific SEQ ID NO: 36, wherein each of the chemically-modified probes has a terminally attached fluorescent moiety and a terminally attached quenching moiety.

In some embodiments of this aspect of the disclosure, the composition can comprise at least one of the PCR primer pairs and a chemically-modified probe of the group consisting of: aldoa-specific SEQ ID NOs: 1 and 2, and SEQ ID NO: 25; arid3a-specific SEQ ID NOs: 3 and 4, and SEQ ID NO: 26; lgals1-specific SEQ ID NOs: 5 and 6, and SEQ ID NO: 27; hbegf-specific SEQ ID NOs: 7 and 8, and SEQ ID NO: 28; afp-specific SEQ ID NOs: 9 and 10, and SEQ ID NO: 29; slc35d2-specific SEQ ID NOs: 11 and 12, and SEQ ID NO: 30; cyp2c9-specific SEQ ID NOs: 13 and 14, and SEQ ID NO: 31; cyp4v2-specific SEQ ID NOs: 15 and 16, and SEQ ID NO: 32; limk2-specific SEQ ID NOs: 17 and 18, and SEQ ID NO: 33; acp2-specific SEQ ID NOs: 19 and 20, and SEQ ID NO: 34; lgals3-specific SEQ ID NOs: 21 and 22, and SEQ ID NO: 35; and ndrg1-specific SEQ ID NOs: 23 and 24, and SEQ ID NO: 36.

In some embodiments of this aspect of the disclosure, the terminally attached fluorescent moiety is attached to the 3' terminus of a probe and the terminally attached quenching moiety is attached to the 5' terminus of a probe.

In some embodiments of this aspect of the disclosure, the terminally attached fluorescent moiety is attached to the 5' terminus of a probe and the terminally attached quenching moiety is attached to the 3' terminus of a probe.

Accordingly, in embodiments of this aspect of the disclosure, the composition for determining whether a hepatocellular carcinoma tissue of a patient has a differential gene expression signature of a metastatic hepatocellular carcinoma tissue can comprise any of the preceding embodiments.

Still another aspect of the disclosure encompasses embodiments of a kit comprising at least one container having at least one of the PCR primer pairs and a chemically-modified probe of the group consisting of: aldoa-specific SEQ ID NOs: 1 and 2, and SEQ ID NO: 25; arid3a-specific SEQ ID NOs: 3 and 4, and SEQ ID NO: 26; lgals1-specific SEQ ID NOs: 5 and 6, and SEQ ID NO: 27; hbegf-specific SEQ ID NOs: 7 and 8, and SEQ ID NO: 28; afp-specific SEQ ID NOs: 9 and 10, and SEQ ID NO: 29; slc35d2-specific SEQ ID NOs: 11 and 12, and SEQ ID NO: 30; cyp2c9-specific SEQ ID NOs: 13 and 14, and SEQ ID NO: 31; cyp4v2-specific SEQ ID NOs: 15 and 16, and SEQ ID NO: 32; limk2-specific SEQ ID NOs: 17 and 18, and SEQ ID NO: 33; acp2-specific SEQ ID NOs: 19 and 20, and SEQ ID NO: 34; lgals3-specific SEQ ID NOs: 21 and 22, and SEQ ID NO: 35; and ndrg1-specific SEQ ID NOs: 23 and 24, and SEQ ID NO: 36; and instructions for a method for determining whether a hepatocellular carcinoma tissue of a patient has a differential gene expression signature of a metastatic hepatocellular carcinoma tissue.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified.

EXAMPLES

Example 1

Transgenic mice: Mouse Twist1 cDNA was PCR cloned into the bidirectional tetO7 vector S2f-IMCg57 at EcoRI and NotI sites, replacing the eGFPORF. The resultant construct, Twist1-tetO7-luc, was sequenced, digested with KpnI and XmnI, and used for injection of FVB/N pronuclei. Founders were screened by genotyping using PCR.

Founders were mated to LAP-tTA mice, and BLI was used to additionally screen for functional Twist1-tetO7-luc founders, subsequently termed TRE-Twist/Luc. The LAP-tTA and TetO-MYC transgenic lines have been described previously (Kistner et al., (1996) *Proc. Natl. Acad. Sci. U.S.A.* 93: 10933-10938; Shachaf et al., (2004) *Nature* 431: 1112-1117; Felsher & Bishop (1999) *Mol. Cell* 4: 199-207). TRE-Twist/Luc mice were mated to LAP-tTA/TRE-MYC mice, and progeny were screened by PCR. Doxycycline (Sigma) was administered in the drinking water weekly (0.1 mg/mL) during mating and continuing until mice reached approximately 6 weeks of age. Animals were euthanized upon disease morbidity as assessed by tumor burden. Macrometastases were assessed upon necropsy and tissues were collected and stored for further analysis.

Example 2

Circulating tumor cells: To analyze circulating tumor cells (CTCs), peripheral blood (200-300 µL) was collected from the tail vein of 10 transgenic mice (3 MYC and 7 MYC/Twist1) prior to apparent disease onset and at time of morbidity. From these, 4 MYC/Twist1 mice were treated with Dox, and peripheral blood was collected 2 weeks and 2 months after transgene inactivation. As a control, peripheral blood was collected from two healthy FVB/N mice. Red blood cells were removed by incubation with PHARMLYSE™ (BD Biosciences) for 15 mins at room temperature. RNA was isolated from the remaining cells using NUCLEOSPIN™ mRNA extraction kits (Macherey-Nagel). cDNA was synthesized via reverse transcriptase reaction performed with Superscript II (Invitrogen) using 2 µg of total RNA. Quantitative PCR was performed for human MYC (hMYC), Luciferase (Luc), and ubiquitin on an ABI PRISM 7900HT cycler (Applied Biosystems) using SYBR green for detection. Values were normalized to ubiquitin and averaged for each genotype. Statistical significance of the difference between groups was assessed by Mann-Whitney test, with two-tailed $p<0.05$ considered significant.

Example 3

Small animal imaging: In vivo bioluminescent imaging was utilized to confirm oncogene activation in transgenic mice beginning one week before, and continuing each week following Dox removal. BLI was performed on an IVIS Spectrum (Caliper Life Sciences, Hopkinton, Mass.). Briefly, mice were injected intraperitoneally with the substrate D-Luciferin (150 mg/kg) and then anesthetized with 2% isofluorane delivered by the Xenogen XGI-8 5-port Gas Anesthesia System. Animals were then placed into the IVIS Spectrum, and Living Image Software was used to collect, archive, and analyze photon fluxes and transform them into pseudocolor images.

Micro-computed tomography (microCT) scans were performed to examine for metastatic lesions to the lungs of transgenic mice. Mice were imaged beginning 2 months after transgene activation and every 2-4 weeks thereafter until disease morbidity. A cohort of 4 mice was treated with Dox to inactivate MYC and Twist1 upon disease morbidity to measure sustained disease regression. This cohort was imaged on the day of inactivation, every two weeks after Dox treatment for the first two months, and each month thereafter. MicroCT was performed on a custom GEHC (London, Ontario) eXplore RS150 cone-beam scanner, which uses a fixed anode with tungsten target source. Animals were anesthetized with 2% isofluorane in a nitrogen/oxygen mixture. Scans were performed at 97 µm resolution, using a 70 kV (40 mA) beam to acquire images at 286 radial views over 200 degrees around the subject. Four frames were exposed and averaged in each position. Data were corrected using the GEHC reconstruction utility and volumes generated using the same application, which were viewed using the GEHC Microview software. Mice were exposed to 19.4 rads per microCT scan.

Example 4

Immunohistochemistry and Immunofluorescence: Paraffin-embedded tumor sections were deparaffined by successive incubations in xylene, graded washes in ethanol, and PBS. Epitope unmasking was performed by steaming in DAKO antigen retrieval solution for 45 mins. Paraffin embedded sections were immunostained with MYC (1:150, Epitomics), E-cadherin (1:100, BD Pharmingen), or β-Catenin (1:100, BD Pharmingen) overnight at 4° C. The tissue was washed with TBST and incubated with biotinylated anti-rabbit or anti-mouse for 30 mins at room temperature (1:300 Vectastain ABC kit, Vector Labs). Sections were developed using 3,3'-Diaminobenzidine (DAB), counterstained with hematoxylin and mounted with Permount. Images were obtained with a Nikon microscope.

Example 5

Microarray Analysis: Tissue was collected from MYC primary, MYC/Twist primary, and MYC/Twist metastatic tumors, and RNA was isolated. RNA from the samples was run on Illumina WG-6 murine high-density expression arrays. The arrays were read and the data exported using Illumina Bead Studio 3.4. The data were loaded into Genespring GX 10 for basic statistical analysis.

The initial filtering of the significant genes was done by conducting an ANOVA (p=0.05, Benjamini Hochberg test used for multiple testing correction) between the four sample types: normal liver, MYC HCC, MYC/Twist1 HCC, and MYC/Twist1 metastases. The genes were filtered for a greater than 2-fold change from gene expression in normal liver. The data was clustered via a hierarchal clustering algorithm, using Euclidian distances and a centroid linkage, as shown in FIG. 3.

For the GSEA (Subramanian et al., (2005) *Proc. Natl. Acad. Sci. U.S.A.* 102: 15545-15550, incorporated herein by reference in its entirety) pre-rank analysis performed in FIG. 4, a less stringent filtering system was used. For each tumor type, MYC HCC, MYC/Twist1 HCC, and MYC/Twist1 MET, a simple volcano plot filtering was conducted comparing these sample groups to the normal liver group (two-tailed, unpaired, student t-test, $p<0.05$; Benjamini Hochberg test used for multiple testing correction; fold Change greater than 2-fold). These same lists were then compared via Venn diagram to ascertain significant genes that were unique to each tumor type and that overlapped between various sample combinations. Hierarchal clustering, heat maps, and Venn diagrams were generated in Genespring GX 10. GSEA pre-rank analysis comparing the gene profiles to previously generated gene sets was performed using GSEA desktop v2.07 and symbol curated data sets (c2.cgp.v3.0.symbols.gmt) from the Broad Institute. The curated data sets were downloaded and then refined to include only those relevant to HCC, metastasis, tumor EMT, and tumor invasiveness. GSEA pre-rank analysis comparing our gene profiles to MeSH pathway term gene sets was performed using GSEA desktop v2.07. MeSH pathway term data sets were created by using the Agilent Literature Search Plug-in in Cytoscape v2.6.3 to generate pathways associated with "tumor EMT", "tumor metastasis", and "tumor invasion" or "tumor invasiveness" in "*Homo sapiens*" or human, and then exporting the gene lists associated with these pathways to .gmt files.

Example 6

Survival Analysis: Raw expression data for four HCC data sets (Ye et al., (2003) *Nat. Med.* 9: 416-423; Lee et al., (2004) *Nat. Genet.* 36: 1306-1311; Lee et al., (2006) *Nat. Med.* 12: 410-416; Tsuchiya et al., *Mol. Cancer* 9: 7418; incorporated herein by reference in their entireties) were downloaded from the Gene Expression Omnibus (GEO), converted to log(2) values if required, missing values were imputed, and expression values were quantile normalized within each study.

For dye swap experiments, Cy3 and Cy5 labeled sample microarrays were merged by averaging paired sample profiles. Survival analysis was performed by univariate Cox regression analysis in each cohort to test associations between expression levels of each microarray probe and clinical outcomes (including overall survival (OS) and relapse free survival (RFS)). Finally, Z-scores (log of the hazard ratio divided by its standard deviation) were averaged for multiple probes corresponding to a given gene, yielding a single survival Z-score for each gene.

A ranked list of each of these Z-scores for HCC was created for each dataset, and a publically available pre-rank GSEA algorithm was employed to test whether each of the gene signatures derived from the murine HCC model was enriched for poor prognosis (positive Z-score) or good prognosis (negative Z-score) genes, including up- and down-regulated genes from: MYC HCC, MYC/Twist1 HCC, MYC/Twist1 MET, MYC/Twist1 HCC+MYC/Twist1 MET, MYC HCC+MYC/Twist1 HCC, MYC HCC+MYC/Twist1 MET, MYC HCC+MYC/Twist1 HCC+MYC/Twist1 MET. Each gene set was thereby assigned a GSEA Normalized Enrichment Score (NES) assessing the skew of its members towards positively or negatively prognostic genes (Subramanian et al., (2005) *Proc. Natl. Acad. Sci. U.S.A.* 102: 15545-15550). Gene lists of both up- and down-regulated genes for each of four publically available human HCC metastasis signatures (Coulouarn et al., (2009) *Oncogene* 28: 3526-3536; Coulouarn et al., (2008) *Hepatology* 47: 2059-2067; Kaposi-Novak et al., (2006) *J. Clin. Invest.* 116: 1582-1595; Roessler et al., *Cancer Res.* 70: 10202-10212) were similarly evaluated, as well as a combination of all four (Human HCC Total Metastasis) to encompass any gene that had been previously implicated in these studies. The survival NES was also established for the overlapping genes from the cross comparisons of our murine signatures to each of the human HCC metastasis signatures as well as the Human HCC Total Metastasis signature. Gene sets were ranked by their NES and p values of $p<0.05$ and listed in Table 2.

For any signature that was determined significantly correlated to poor prognosis in the Z score analysis, its ability to stratify patients into high- and low-risk groups was tested in publically available human HCC cohorts that had overall survival (OS) available (Ye et al., (2003) *Nat. Med.* 9: 416-423; Lee et al., (2006) *Nat. Med.* 12: 410-416) (GSE364 and GSE1898; Table 3). Genes comprising the murine MYC/Twist1 HCC+MET signature, as well as the 17-gene signature, were used to perform a k-means clustering analysis to group samples into two groups: patients whose gene expression aligned with the signature (high expression of signature genes) and patients that did not. Survival curves for these two groups were generated by Kaplan-Meier analysis. The k-means clustering was also performed on a third, larger human HCC cohort17 (GSE14520) to independently validate our findings. Statistical significance of the difference between stratification groups was assessed by Mantel-Cox log-rank test, with $p<0.05$ considered significant.

Example 7

Metastasis Analysis: The difference in the expression of genes comprising the murine, human, and overlapping signatures from the survival analyses was compared between primary human HCCs from patients with and without metastases in the one dataset that had this information available (Ye et al., (2003) *Nat. Med.* 9: 416-423) (GSE364).

The average expression of genes was calculated separately for each signature in each patient sample. Statistical significance of the difference between samples (primary tumors with/without metastases) was determined by a two-tailed, unpaired student t-test of the respective group means with $p<0.05$ considered significant.

Example 8

Univariate and Multivariate Analysis: Cox proportional hazards regression was used to analyze the effect of clinical variables on patient survival, using STATA 11.0. Clinical variables included age, gender, pre-resection AFP, cirrhosis, tumor size or size of the largest tumor when multiple tumors are present, and the HCC prognosis staging systems Barcelona Clinic Liver Cancer (BCLC), Cancer Liver Italian Program (CLIP) or Tumor Node Metastasis (TNM) classification. An AFP cutoff of 300 ng/mL and tumor size of 5 cm were used in Cox regression analysis and are clinically relevant values used to distinguish patient survival. A univariate test was used to examine the influence of the 17-gene signature or each clinical variable on patient survival. A multivariate analysis was done to estimate the hazards ratio of the predictor while controlling for clinical variables that were significantly associated with survival in the univariate analysis. Because tumor size was collinear with tumor staging, this variable was not included in the multivariate analysis. It was determined that the final model met the proportional hazards assumption.

Example 9

Migration, Invasion, and Metastasis Assays: Human Huh7 HCC cells or a murine cell line derived from the liver of an adult LAP-tTA/TRE-MYC (MYC) mice bearing HCC were retrovirally transduced with either murine Twist1 or a vector control. Following selection, protein expression was verified via SDS-PAGE followed by PVDF immunoblot using an antibody against TWIST1 (Santa Cruz Biotechnology, Santa Cruz, Calif.). For the wound healing assay, HCC cells were grown to confluency, the monolayer was scratched, non-adherent cells were removed via wash with sterile PBS, and media containing 2% FBS was added.

For invasion assays, Transwell chambers (6.5 mm diameter, 0.22 μm pore size; Corning, Corning, N.Y.) were coated on both sides with Collagen (Vitrogen, Cohesion Technologies Catalog #FXP-019) at 4° C. overnight. HCC cells were added to the upper chamber ($1\times10^5$/chamber) with medium containing 2% FBS in the upper and lower chambers. After incubating for 6 hours at 37° C., cells were removed from the upper chamber, Transwell membranes were fixed in 100% methanol and mounted on a glass slide in Vectashield medium with 4',6-diamidino-2-phenylindole (Vector Laboratories, Burlingame, Calif.), and the number of cells that had migrated was quantified by immunofluorescence on a Nikon Eclipse E800 microscope.

To examine the metastatic potential, murine HCC cells ($2.5\times10^6$) were injected into the peritoneal cavity of immunocompromised SCID mice (n=4 for each of vector or Twist1). Similarly, human Huh7 cell line ($5\times10^4$) were injected into the tail vein of SCID mice (n=4 for each of vector or Twist1). Mice were euthanized upon morbidity and liver, lymph node, spleen, kidney and lung tissues were collected, fixed in formalin, embedded in paraffin, and analyzed by H&E for the presence of metastases. The identification of metastases was confirmed by immunohistochemistry against human MYC protein.

Example 10

Quantitative PCR: Tissue was harvested from wild type FVB/N and Twist1 livers or MYC and MYC/mTwist1 HCC upon disease morbidity and was snap frozen in liquid nitrogen and stored at −80° C. RNA was extracted from frozen tumor samples using Nucleospin mRNA extraction kits (Machery-Nagel). cDNA was synthesized using a reverse transcriptase reaction performed with Superscript II (Invitrogen) by using 2 μg of total RNA. Quantitative PCR was performed with an ABI PRISM 7900HT cycler (Applied Biosystems) using SYBR green as a method of detection.

To analyze Twist1 expression in a cohort of human HCC, Tissue qPCR Arrays (OriGene Technologies, Rockville, Md.) were used according to manufacturer specifications.

Example 11

A database was constructed that merged gene expression data with paired survival data from published human HCC studies (a total of 4 studies). The normalized enrichment score (or the Z-score) is the combined survival score associated with each of the genes within each of the signatures. The signatures were then ranked by the Z-score to determine which is the most prognostic for poor patient survival.

TABLE 2

Survival analysis of signatures derived from the MYC/Twist1 HCC model compared to human metastasis signatures.

| | SIZE | NES (Z-Score) | p-value | FDR |
|---|---|---|---|---|
| Gene Signatures with Positive Z-Scores | | | | |
| Coulouarn et al., TGFβ_UP | 80 | 1.952798 | <0.00001 | 0.012737518 |
| HUMAN HCC Total Metastasis_UP | 438 | 1.791612 | <0.00001 | 0.012622777 |
| MYC/Twist1 HCC + MET + HCC Total Metastasis_UP (17 Gene) | 17 | 1.774229 | 0.007936508 | 0.012511895 |
| MYC/Twist1 HCC + MET_UP | 215 | 1.748574 | <0.00001 | 0.013197329 |
| Kaposi-Novak et al., c-MET_UP (Early &Late) | 37 | 1.729859 | 0.007827789 | 0.013034524 |
| Roessler et al. Human HCC Metastasis_UP | 99 | 1.617141 | 0.001904762 | 0.024850149 |
| MYC/Twist1 MET_UP | 32 | 1.588162 | 0.020661157 | 0.028800592 |
| Coulouarn et al. miR122 Loss_DOWN | 234 | 1.411826 | 0.00845666 | 0.085526034 |
| MYC/Twist1 HCC_UP | 1218 | 1.324624 | <0.00001 | 0.12559737 |
| MYC/Twist1 MET_DOWN | 29 | 0.792686 | 0.7832031 | 0.87137 |
| MYC HCC + MYC/Twist1 MET_UP | 1 | 0.765893 | 0.840954 | 0.801432 |
| MYC HCC + MYC/Twist1 HCC + MYC/Twist1 MET_UP | 46 | 0.699141 | 0.9384328 | 0.92864406 |

TABLE 2-continued

Survival analysis of signatures derived from the MYC/Twist1 HCC model compared to human metastasis signatures.

|  | SIZE | NES (Z-Score) | p-value | FDR |
|---|---|---|---|---|
| Gene Signatures with Negative Z-Scores |  |  |  |  |
| Couloaum et al. miR122 Loss_UP | 171 | −2.85968 | <0.00001 | <0.00001 |
| HUMAN HCC Total Metastasis_DOWN | 331 | −2.77636 | <0.00001 | <0.00001 |
| MYC/Twist1 HCC_DOWN | 954 | −2.35784 | <0.00001 | <0.00001 |
| Couloaum et al., TGFβ_DOWN | 104 | −2.16702 | <0.00001 | <0.00001 |
| MYC/Twist1 HCC + MET_DOWN | 84 | −2.01843 | <0.00001 | 6.33E−04 |
| Kaposi-Novak et al. c-MET_DOWN | 18 | −1.8849 | <0.00001 | 0.002562043 |
| MYC HCC + MYC/Twist1 HCC_DOWN | 35 | −1.78791 | 0.002119 | 0.001387 |
| MYC HCC + MYC/Twist1 HCC + MYC/Twist1 MET_DOWN | 9 | −1.63356 | 0.021526419 | 0.017714437 |
| Kaposi-Novak et al. c-MET_PERSISTANT | 16 | −1.21163 | 0.20661157 | 0.25295463 |
| Roessler et al., Human HCC Metastasis_DOWN | 44 | −1.15629 | 0.21941748 | 0.31861624 |
| MYC HCC_DOWN | 24 | −0.92964 | 0.5458248 | 0.69933766 |
| MYC HCC + MYC/Twist1 MET_DOWN | 5 | −0.80368 | 0.715152 | 1 |
| MYC HCC + MYC/Twist1 HCC_UP | 52 | −0.60385 | 0.993827 | 0.984743 |
| MYC HCC_UP | 29 | −0.58789 | 0.9873684 | 0.9809853 |

_UP: up-regulated
_DOWN: down-regulated

Example 12

GSEA Analysis of Cytoscape-generated Agilent literature search pathways: MYC/Twist HCC, MYC/Twist MET, and MYC/Twist HCC+MET were compared to MeSH pathway term gene sets using GSEA desktop v2.07. MeSH pathways associated with "tumor EMT", "tumor metastasis", and "tumor invasion" or "tumor invasiveness" in "*Homo sapiens*" or human as defined by Cytoscape were used. Gene sets were ranked in order of p-value and normalized enrichment score (NES). Tumor EMT was the only pathway deemed significant at p<0.05.

TABLE 3

GSEA Analysis of Cytoscape-generated Agilent literature search pathways.

|  | SIZE | NES | p-value | FDR |
|---|---|---|---|---|
| Gene Sets Compared to MYC/Twist1 HCC + MET p-0.05, FC = 1 |  |  |  |  |
| TUMOR EMT | 38 | 1.385597 | 0.024291 | 0.211021 |
| TUMOR METASTASIS | 23 | 1.36786 | 0.074713 | 0.167071 |
| TUMOR INVASION or TUMOR INVASIVENESS | 18 | 1.330785 | 0.097297 | 0.135713 |
| Gene Sets Compared to MYC/Twist1 MET p-0.05, FC = 1 |  |  |  |  |
| TUMOR EMT | 55 | 1.429947 | 0.026639 | 0.168315 |
| TUMOR METASTASIS | 34 | 1.266555 | 0.170825 | 0.303986 |
| Gene Sets Compared to MYC/Twist1 HCC p-0.05, FC = 1 |  |  |  |  |
| TUMOR INVASION or TUMOR INVASIVENESS | 30 | 1.210396 | 0.223092 | 0.26702 |
| TUMOR EMT | 169 | 1.496296 | 0.021113 | 0.096357 |
| TUMOR METASTASIS | 134 | 1.027785 | 0.444238 | 0.923486 |
| TUMOR INVASION or TUMOR INVASIVENESS | 159 | 0.780026 | 0.8 | 0.764866 |

Example 13

Hazard ratio calculations for human and murine metastasis signatures: Hazard ratio analyses were performed on each murine signature in two publically available human HCC cohorts that had overall survival (OS) individually. From this hazard ratio analysis and the Z-score analysis (Table 3), the best murine "metastasis" signature was determined to test for its ability to prognosticate survival in human HCC patients was MYC/Twist HCC+MET_UP.

TABLE 4

Hazard ratio calculations to determine which signatures would be chosen for k-means clustering and ultimately Kaplan-Meyer survival analysis.

| Gene Signature | coef | HR | secoef | Z-score | P-value | HR_low | HR_high |
|---|---|---|---|---|---|---|---|
| GSE364 # NSAMPLES_USED: 50 | | | | | | | |
| MYC/Twist1 HCC + MET_UP | 1.118114 | 3.059078 | 0.332766 | 3.360056 | 0.000779 | 1.593453 | 5.872754 |
| MYC/Twist1 HCC + MET + HUMAN HCC Total Metastasis_UP (17 Gene) | 1.043478 | 2.839073 | 0.320525 | 3.255525 | 0.001132 | 1.514764 | 5.321181 |
| MYC HCC + MYC/Twist1 HCC + MYC/Twist1 MET_DOWN | 0.776974 | 2.17488 | 0.294659 | 2.636852 | 0.008368 | 1.220733 | 3.874805 |
| MYC HCC + MYC/Twist1 HCC + MYC/Twist1 MET_UP | 0.663123 | 1.940845 | 0.274633 | 2.414579 | 0.015753 | 1.132981 | 3.32475 |
| MYC/Twist1 HCC_UP | 0.265279 | 1.303795 | 0.255723 | 1.037368 | 0.299564 | 0.789837 | 2.152192 |
| MYC/Twist1 HCC + HUMAN HCC Total Metastasis_DOWN | −0.23288 | 0.79225 | 0.280044 | −0.83158 | 0.405648 | 0.457602 | 1.371628 |
| MYC/Twist1 MET_UP | 0.218734 | 1.244501 | 0.273636 | 0.799363 | 0.42408 | 0.727907 | 2.12772 |
| MYC HCC_UP | 0.235665 | 1.265751 | 0.299643 | 0.786486 | 0.431583 | 0.703544 | 2.27722 |
| MYC HCC_DOWN | 0.225953 | 1.253517 | 0.292233 | 0.773195 | 0.439407 | 0.706937 | 2.222695 |
| MYC/Twist1 HCC + HUMAN HCC Total Metastasis_UP | 0.168129 | 1.183089 | 0.271715 | 0.618767 | 0.53607 | 0.694597 | 2.015125 |
| MYC/Twist1 HCC + MET_DOWN | −0.1582 | 0.853681 | 0.275534 | −0.57415 | 0.565865 | 0.497463 | 1.464975 |
| MYC/Twist1 MET_DOWN | 0.081691 | 1.085121 | 0.270688 | 0.301791 | 0.762811 | 0.638363 | 1.844541 |
| MYC/Twist1 HCC_DOWN | −0.07977 | 0.923326 | 0.298027 | −0.26767 | 0.788954 | 0.514842 | 1.655908 |
| GSE1898, OS # NSAMPLES_USED: 76 | | | | | | | |
| MYC HCC + MYC/Twist1 HCC + MYC/Twist1 MET_DOWN | −0.59511 | 0.551499 | 0.161872 | −3.67646 | 0.000236 | 0.401568 | 0.757409 |
| MYC/Twist1 HCC_DOWN | −0.62742 | 0.533969 | 0.170678 | −3.67603 | 0.000237 | 0.382151 | 0.746101 |
| MYC HCC + MYC/Twist1 HCC + MYC/Twist1 MET_UP | 0.564255 | 1.758137 | 0.160078 | 3.524876 | 0.000424 | 1.284678 | 2.406087 |
| MYC/Twist1 HCC + HUMAN HCC Total Metastasis_DOWN | −0.60545 | 0.545826 | 0.173428 | −3.4911 | 0.000481 | 0.388537 | 0.76679 |
| MYC/Twist1 HCC_UP | 0.574207 | 1.775722 | 0.166013 | 3.458816 | 0.000543 | 1.282522 | 2.458585 |
| MYC/Twist1 HCC + MET_DOWN | −0.53159 | 0.587669 | 0.163647 | −3.2484 | 0.001161 | 0.426418 | 0.809897 |
| MYC/Twist1 HCC + MET_UP | 0.535823 | 1.708854 | 0.167079 | 3.207009 | 0.001341 | 1.23165 | 2.370951 |
| MYC/Twist1 HCC + HUMAN HCC Total Metastasis_UP | 0.557349 | 1.746038 | 0.17396 | 3.2039 | 0.001356 | 1.241592 | 2.455434 |
| MYC/Twist1 HCC + MET + HUMAN HCC Total Metastasis_UP (17 Gene) | 0.387924 | 1.473918 | 0.160276 | 2.420355 | 0.015505 | 1.07658 | 2.017903 |
| MYC/Twist1 MET_DOWN | 0.257504 | 1.293697 | 0.163759 | 1.572456 | 0.115845 | 0.938514 | 1.783301 |

TABLE 4-continued

Hazard ratio calculations to determine which signatures would be chosen for k-means clustering and ultimately Kaplan-Meyer survival analysis.

| Gene Signature | coef | HR | secoef | Z-score | P-value | HR_low | HR_high |
|---|---|---|---|---|---|---|---|
| MYC/Twist1 MET_UP | 0.248767 | 1.282444 | 0.164347 | 1.513675 | 0.130108 | 0.929279 | 1.769826 |
| MYC HCC_DOWN | −0.1033 | 0.901854 | 0.130948 | −0.78888 | 0.430181 | 0.697707 | 1.165734 |
| MYC HCC_UP | 0.073974 | 1.076779 | 0.162362 | 0.45561 | 0.64867 | 0.783292 | 1.48023 |

Example 14

Table 5 shows the relative prognostic power of the 20-gene signature compared to previously-published human HCC metastasis signatures.

TABLE 5

| | P-value | HR | 95% CI | P-value | HR | 95% CI | P-value | HR | 95% CI |
|---|---|---|---|---|---|---|---|---|---|
| 20-Gene Signature | 0.001 | 6.8 | 1.9-24.5 | 0.0004 | 2.6 | 1.54-4.41 | 0.04 | 1.9 | 1.0-3.4 |
| MYC/Twist 1 HCC + MET_UP | 0.17 | 2.1 | 0.7-6.2 | 0.0001 | 2.5 | 1.43-3.33 | 0.002 | 2.5 | 1.4-4.6 |
| Met (Kaposi-Novak, et al.) | 0.34 | 0.6 | 0.2-1.7 | 0.0107 | 1.8 | 1.1-2.8 | 0.0001 | 3.2 | 1.7-5.9 |
| miR-122 (Coulounarn, et al) | 0.58 | 1.3 | 0.5-3.9 | 0.0102 | 1.9 | 1.2-3.0 | 0.02 | 2.2 | 1.1-4.2 |
| TGF-$_\beta$ (Coulouarn, et al) | 0.27 | 2.3 | 0.6-10.1 | 0.00054 | 1.9 | 1.2-3.0 | 0.002 | 2.6 | 1.4-4.9 |
| Total Human HCC | 0.01 | 4.6 | 1.3-16.6 | 0.0390 | 1.7 | 1.03-2.86 | 0.0004 | 3.0 | 1.6-5.7 |

Three independent Human HCC patient cohorts were stratified using both the MYC/Twist1 HCC+Met Up-regulated, and the 20-gene signatures derived from our mouse model, three previously published HCC metastasis signatures and the combined list of all genes implicated in predicting metastasis in four independent studies.

Example 15

Method for Identifying a Gene Signature Prognostic for Outcome in Human Hepatocellular Carcinoma: A new mouse model was generated whereby primary MYC-induced non-metastatic hepatocellular carcinoma (HCC) was progressed stepwise to metastatic disease by expression of Twist1. Second, gene expression analysis was performed comparing non-metastatic MYC HCC with metastatic Twist1/MYC HCC, as well as paired metastases from the Twist1/MYC HCC. The differentially expressed genes in the transgenic mouse models of HCC progression were assessed to identify a signature that predicts human HCC outcome. Third, murine-derived gene expression profiles were compared to previously identified human HCC metastasis signatures to isolate the most significant genes for prognosis and metastasis in human liver cancer.

Example 16

Figure 26A:
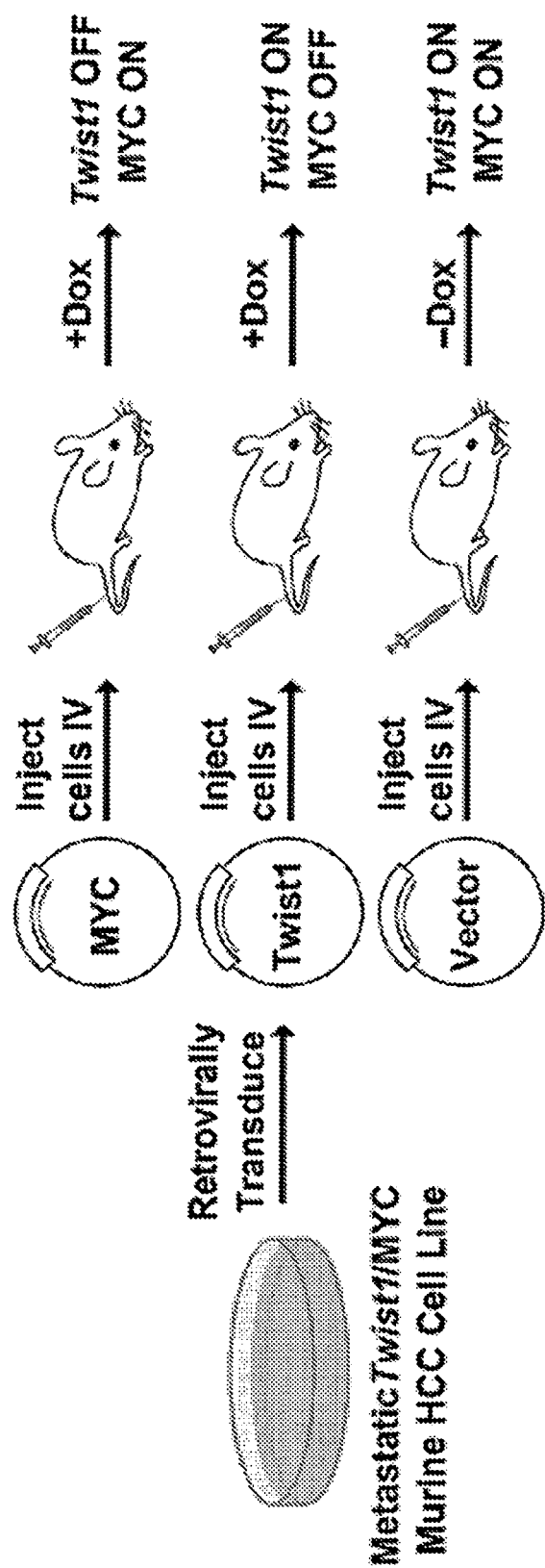
FIGS. 26A and 26B illustrate that HCC metastases require both MYC and Twist1 Expression.
Figure 26B:
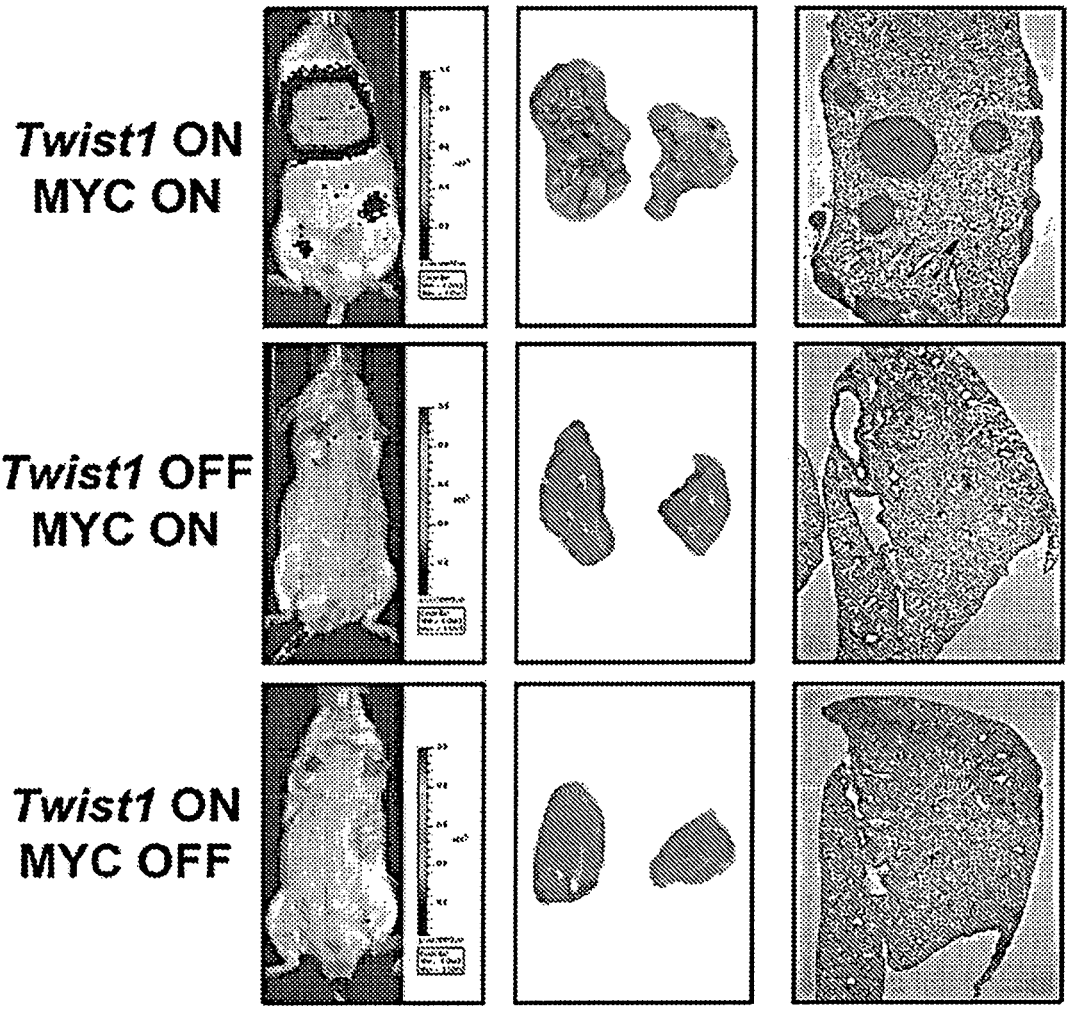

FIGS. 26A and 26B provide data that HCC metastases require both MYC and Twist1 expression. Cell lines derived from the mouse Twist1/MYC HCC were generated and retrovirally transduced with constitutive MYC or Twist1 and injected intravenously (IV) into immunocompromised SCID mice (FIG. 26A). Animals were treated with Dox to singly inactivate either MYC or Twist1. Mice not treated with Dox were used as a control for continued expression of both MYC and Twist1. IV injection of HCC cells resulted in the formation of lung metastases when MYC and Twist1 are expressed (FIG. 26B). Importantly, MYC and Twist1 were each required for maintenance of the metastatic ability of these cells, as suppression of either was sufficient to eliminate growth of HCC in the lungs of recipient animals.

Example 17

To identify specific genes causally associated with malignant progression of HCC, a cross-species analysis was performed. A 592-gene signature was compared to 1008 genes characterized from prior studies of the metastatic human HCC (Coulouarn et al., (2009) Oncogene 28: 3526-3536; Coulouarn et al., (2008) Hepatology 47: 2059-2067; Kaposi-Novak et al., (2006) J. Clin. Invest. 116: 1582-1595; Roessler et al., (2010) Cancer Res. 70: 10202-10212; Ye et al., (2003) Nat. Med. 9: 416-423).

The lasso-regularized proportional hazards model (Simon et al., (2011) J. Statistical Software. 39: 1-13) was applied with cross-validation to choose the tuning parameter. This produced a continuous score for each patient. The resulting score was divided at its median to produce two groups, and Kaplan-Meier curves were computed. This method was applied for all test patients and also separately for each test set.

The comparison of the MYC/Twist1 HCC+MET signature to the Human HCC Total Metastasis Signature gene identified 12 genes specifically involved in cell signaling (Lgals1, Lgals3, Ndrg1 and Hbegf); metabolism (AldoA, ACP2, CYP4V2, CYP2C9 and SLC35D2); Cell motility (Limk2) DNA binding protein (ARID3A); and serum biomarker (AFP). Their respective functions are given in Table 6'

TABLE 6

| Gene | Name | Function | Reported Link to Cancer-Metastasis |
|---|---|---|---|
| AFP | Alpha-fetoprotein | Serum Biomarker | Elevated in HCC patients, tumor marker (blood) |
| ARID3A | AT Rich Interactive Domain 3A | DNA binding protein, TF activity | Alterations in this gene were found in HCC |
| LIMK2 | LIM domain kinase 2 | Cell motility | Important for metastatic behavior and angiogenesis of pancreatic cancer cells |
| LGALS1 | Galectin 1 Galactoside-Binding Lectin | Apoptosis, cell proliferation and cell differentiation | Hallmark genes that are over-expressed in HCC, triggers EMT in HCC |
| LGALS3 | Galectin 3 Galactoside-Binding Lectin | Apoptosis, innate immunity, cell adhesion and T cell regulation | Upregulated in HCC human tissues, suggested to be involved in HCC metastasis |
| Hbegf | Heparin-binding EGF-like growth factor | Growth factor that mediates smooth muscle cell proliferation | Potent inducer of tumor growth and angiogenesis |
| Ndrg1 | N-myc downstream regulated 1 | Stress-responsive protein involved in cell growth, and differentiation | Overexpressed in HCC, biomarker for recurrence and poor prognosis in HCC |
| AldoA | Fructose-bisphosphate aldolase A | Sugar metabolism; expression is repressed in adult liver | Target for the liver specific mir-122 |
| ACP2 | Lysosomal Acid Phosphatase 2 | Enzymatic activity in the Lysosome | Prostate cancer |
| CYP4V2 | Cytochrome P450, Family 4, Subfamily V, Polypeptide 2 | Metabolism of fatty acid precursors | Breast cancer |
| CYP2C9 | Cytochrome P450, Family 2, Subfamily C, Polypeptide 9 | Drug metabolism and synthesis of cholesterol, steroids and other lipids | Suppression of CYP2C9 expression has been reported as a biomarker of HCC |
| SLC35D2 | Solute Carrier Family 35 | Member UDP-GlcNAc/UDP-Glucose Transporter | Lung cancer cells |

By Kaplan-Meier analysis, it was found that the 12-gene signature stratified human HCC patients on the basis of survival from three independent cohorts (Ye et al., (2003) Nat. Med. 9: 416-423; Lee et al., (2004) Nat. Genet. 36: 1306-1311) (FIG. 1-3; Ye, p=0.008; Lee, p=0.2; Overall combined, p=0.0002).

Figure 27:
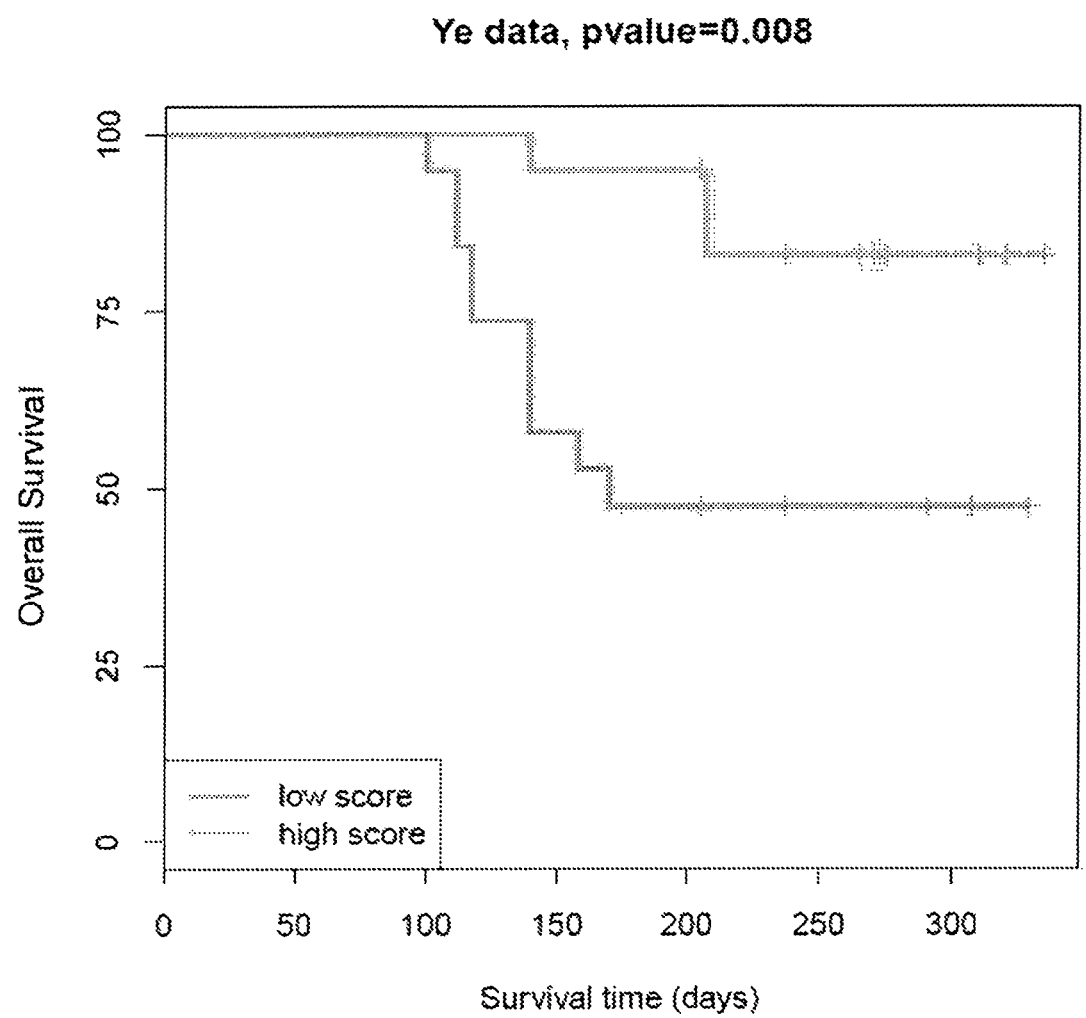
FIGS. 27-29 illustrate that a 12-gene signature of the disclosure was prognostic for poor overall survival in human HCC patients.
Figure 28:
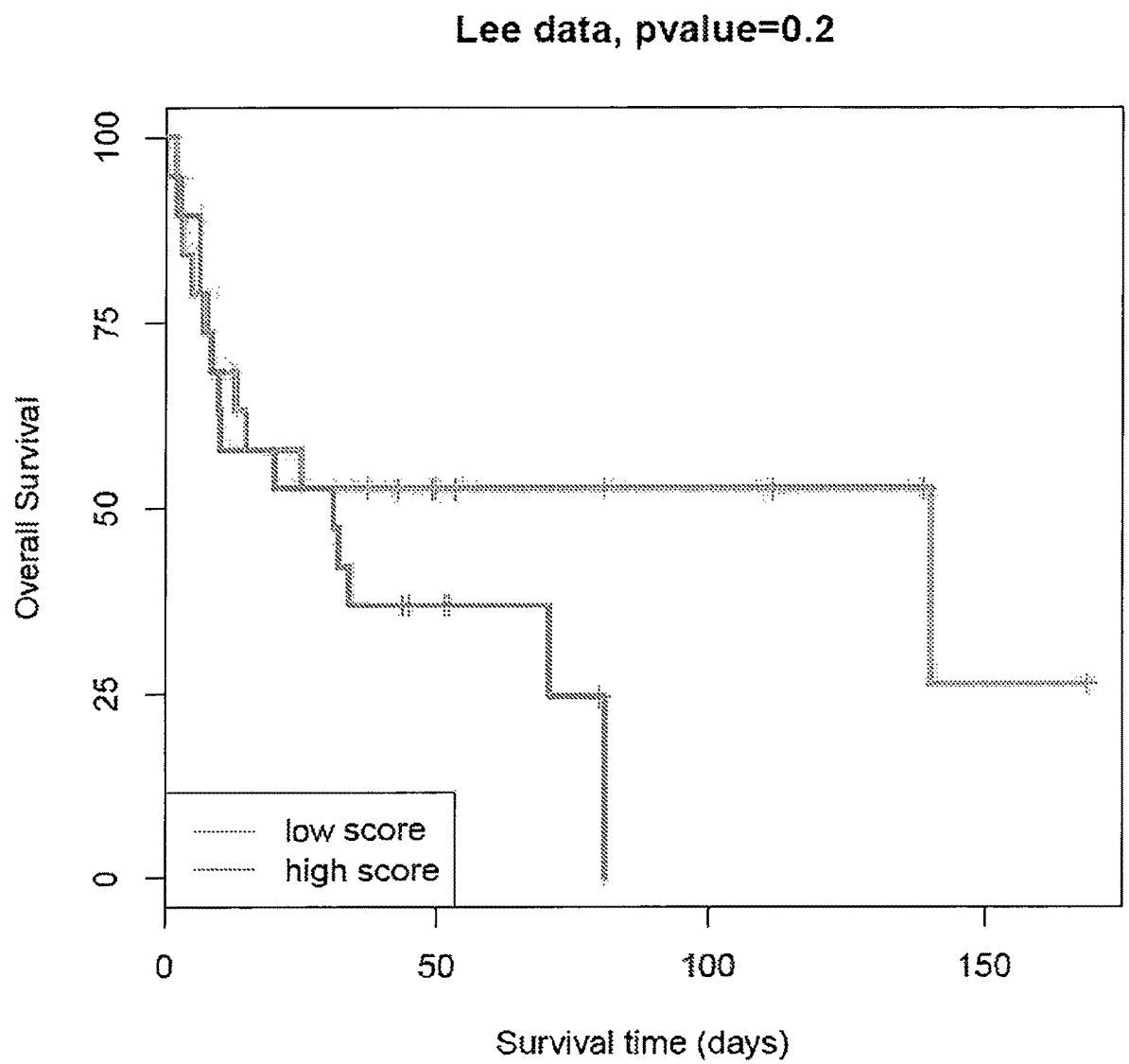
Figure 29:
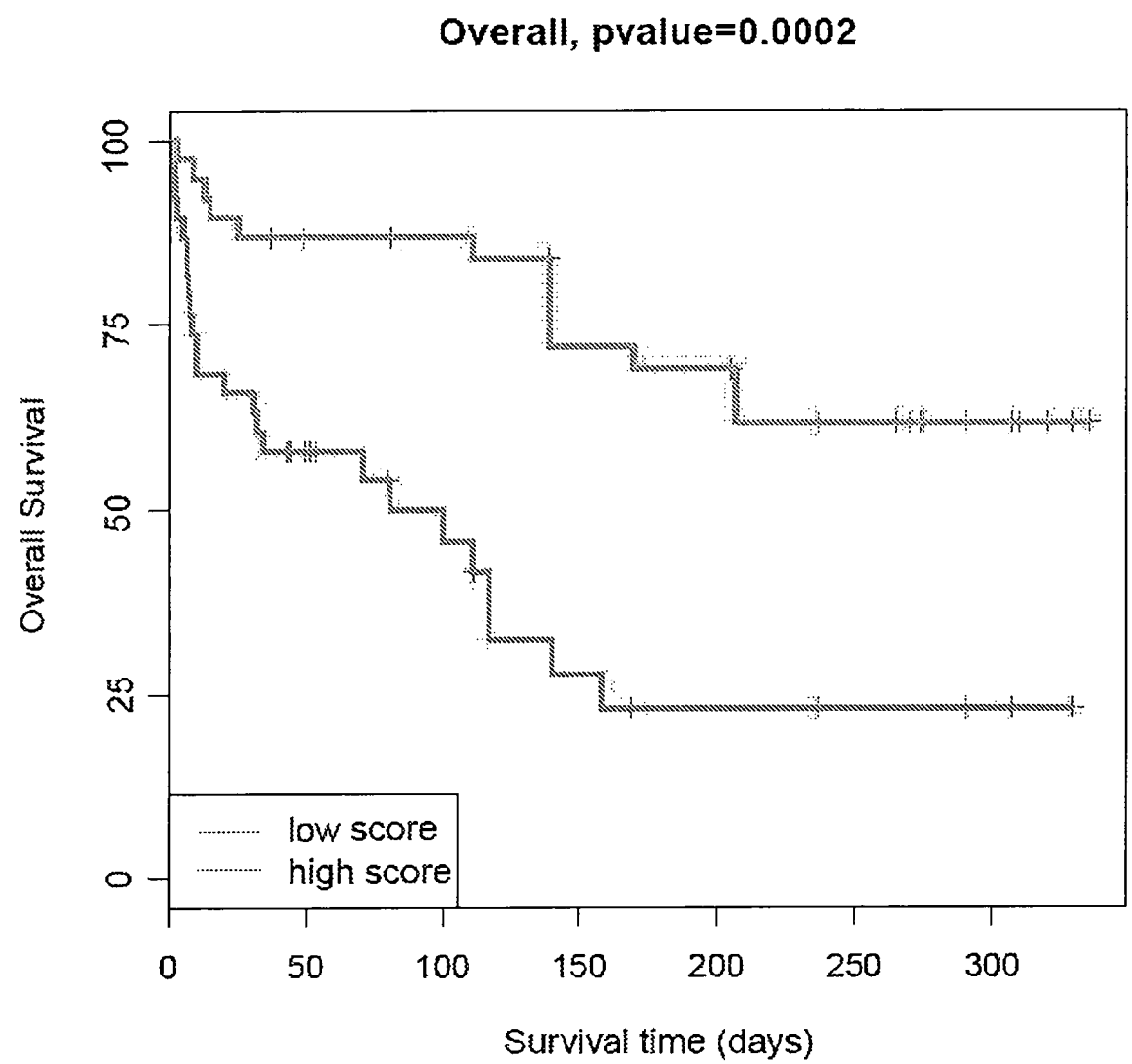
Figure 31:
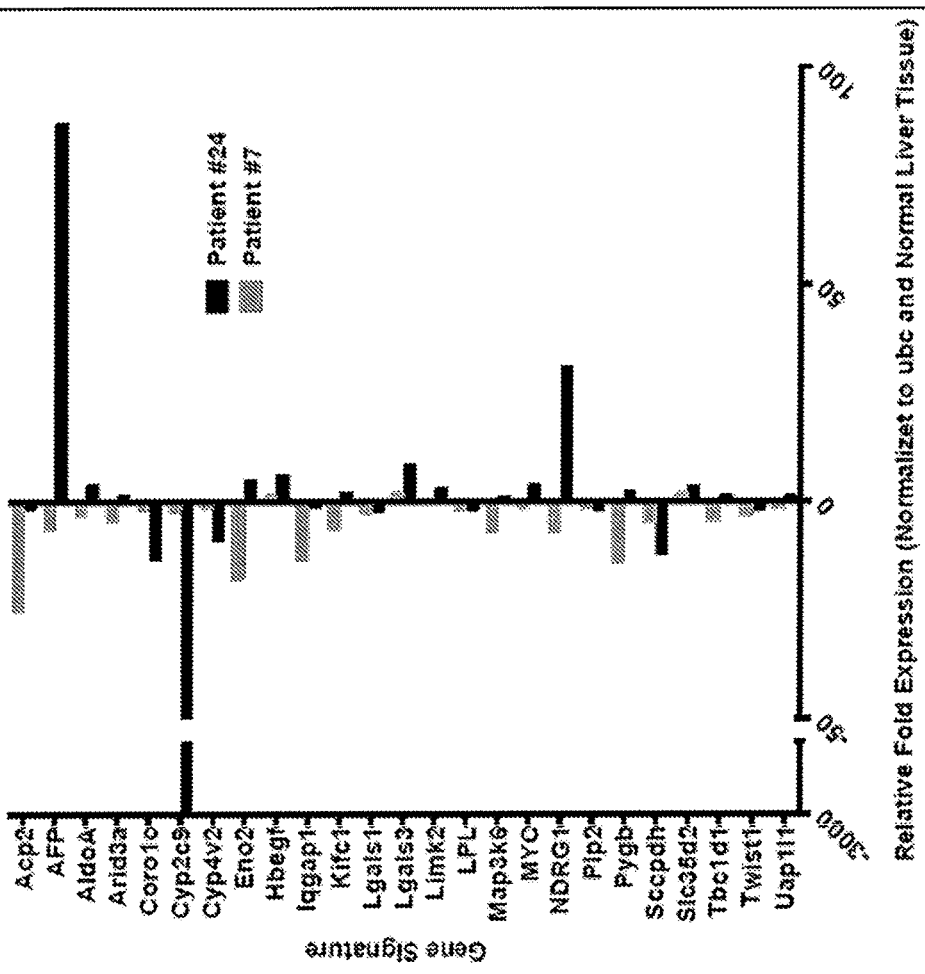
FIG. 31 is a bar-graph illustrating validation of the fluorescence probes of the disclosure FIG. 32 schematically illustrates the validation of the 12-gene signature of the disclosure for predicting human survival of hepatocellular carcinoma using the primers and probes of the disclosure.
Figure 32:
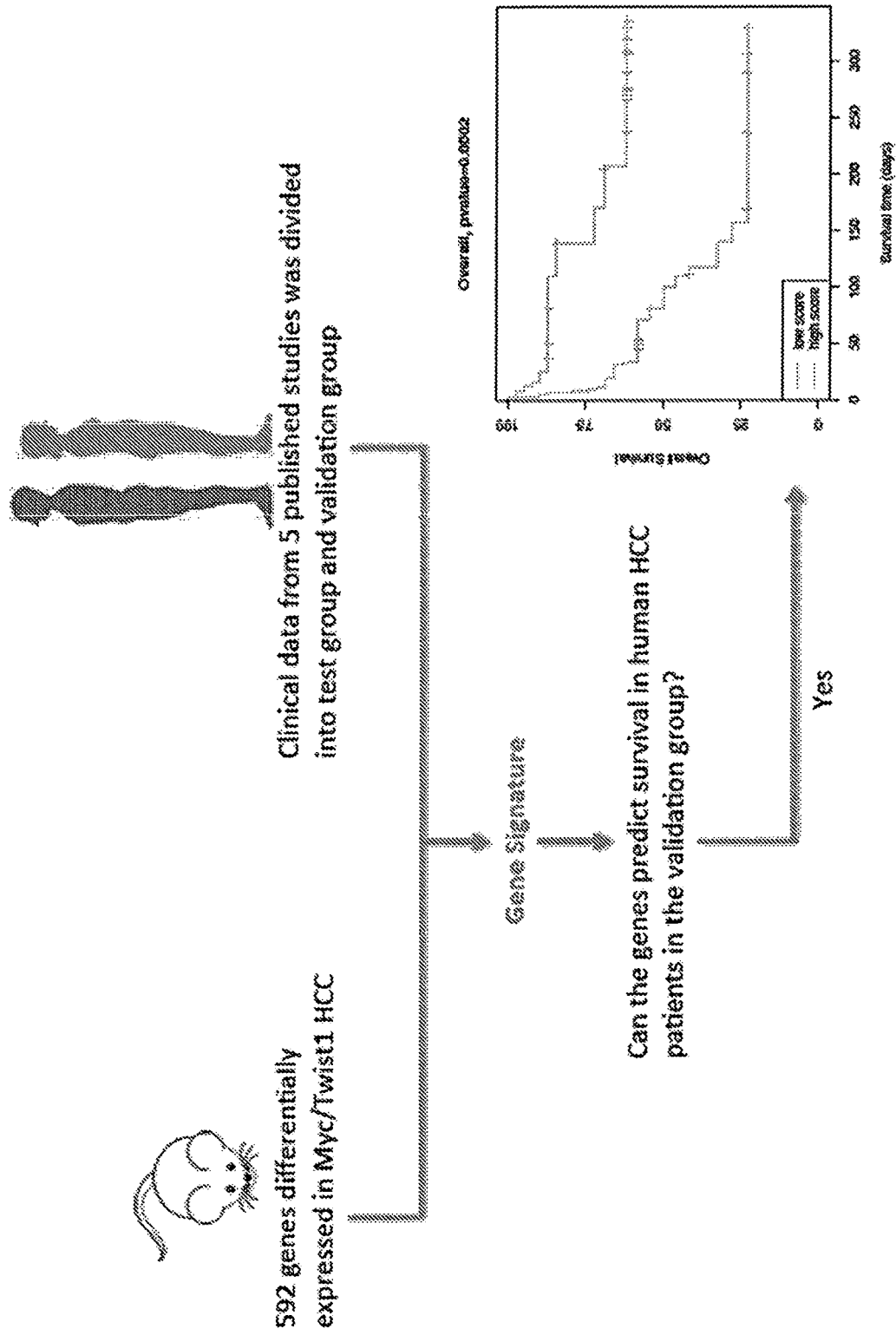
Figure 33:
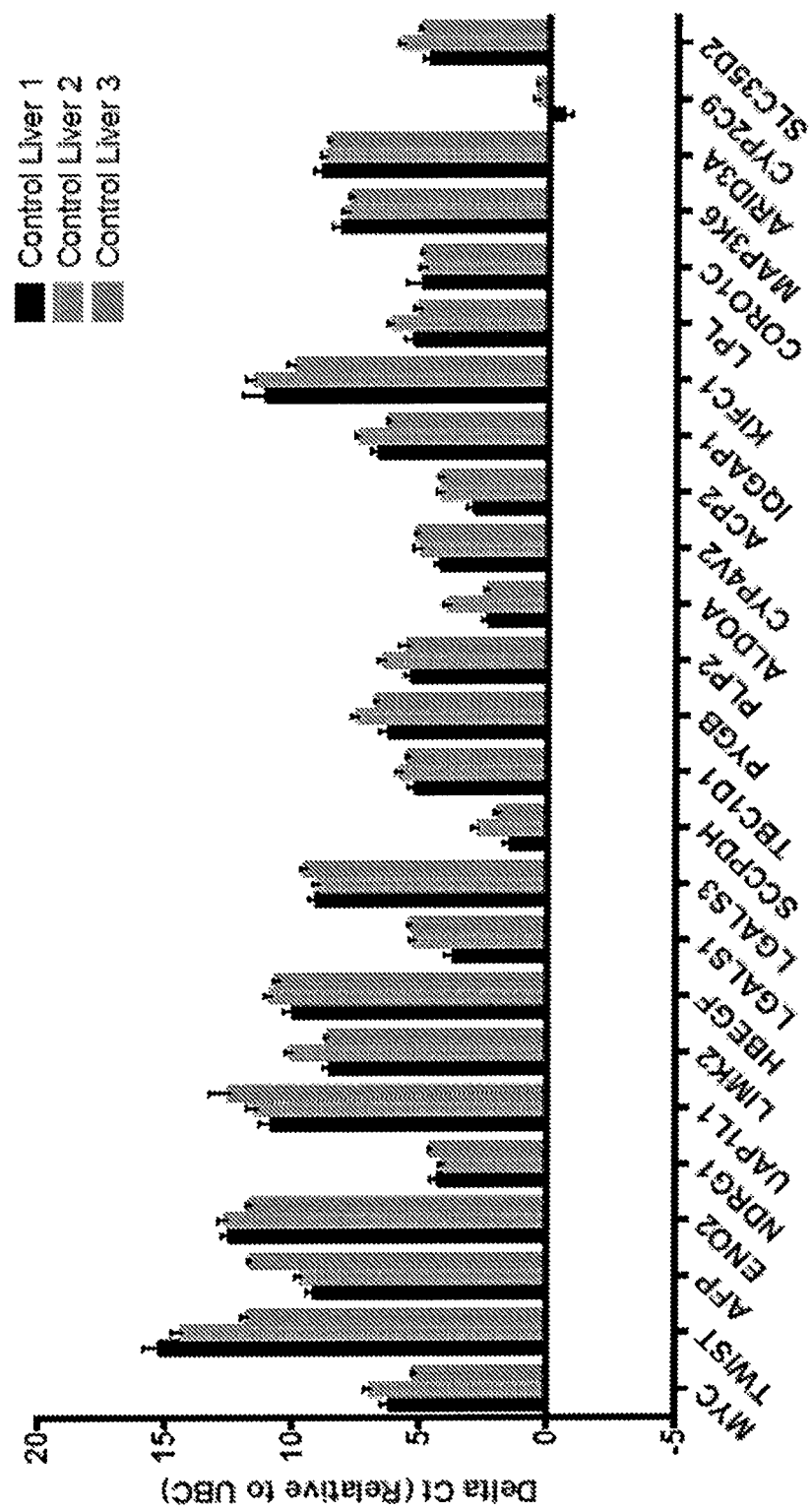
FIG. 33 is a bar-graph illustrating signature gene expression in three control adult liver donor patients.
Figure 34:
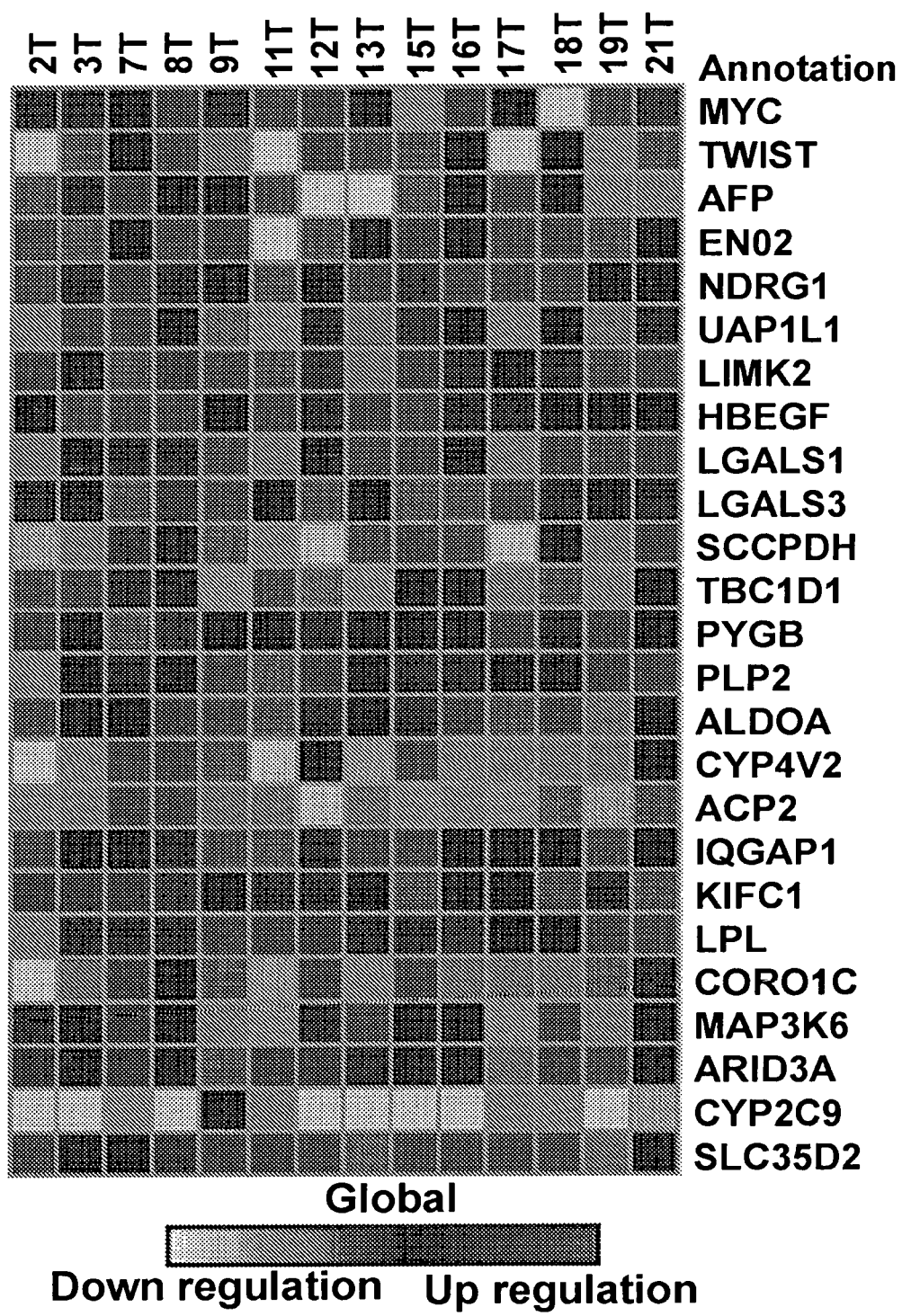
FIG. 34 illustrates the signature gene expression in adult HCC patients.
Figure 35:
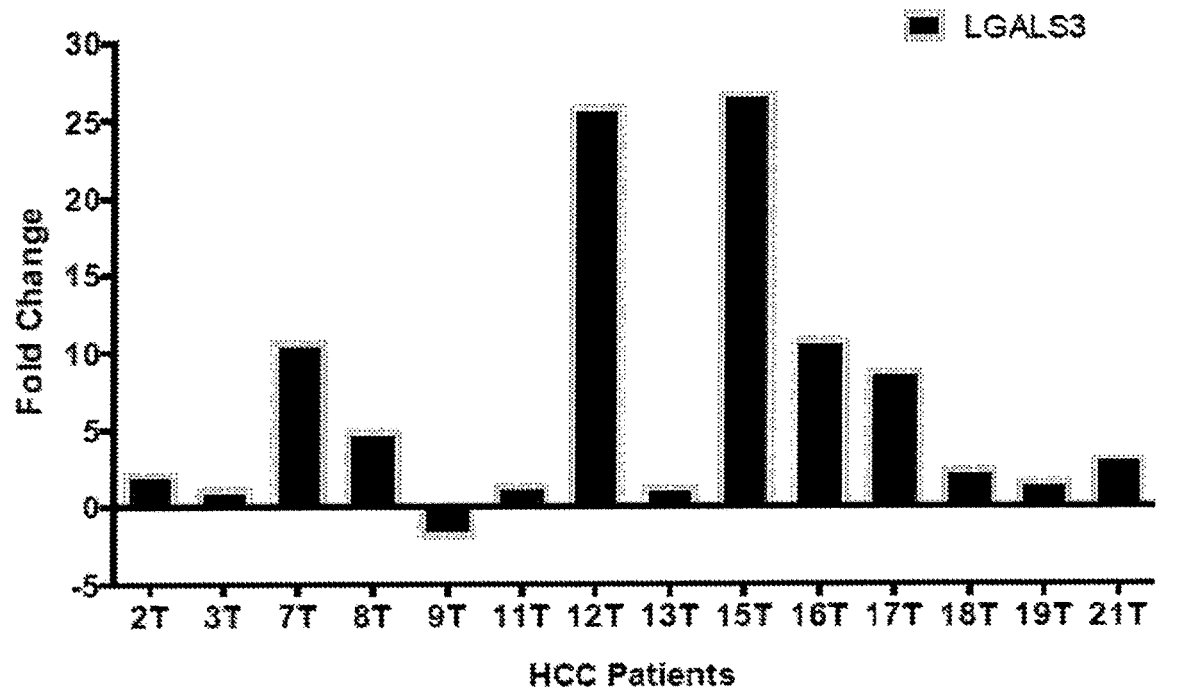
FIG. 35 illustrates the signature gene expression in adult HCC patients-up-regulated genes
Figure 36:
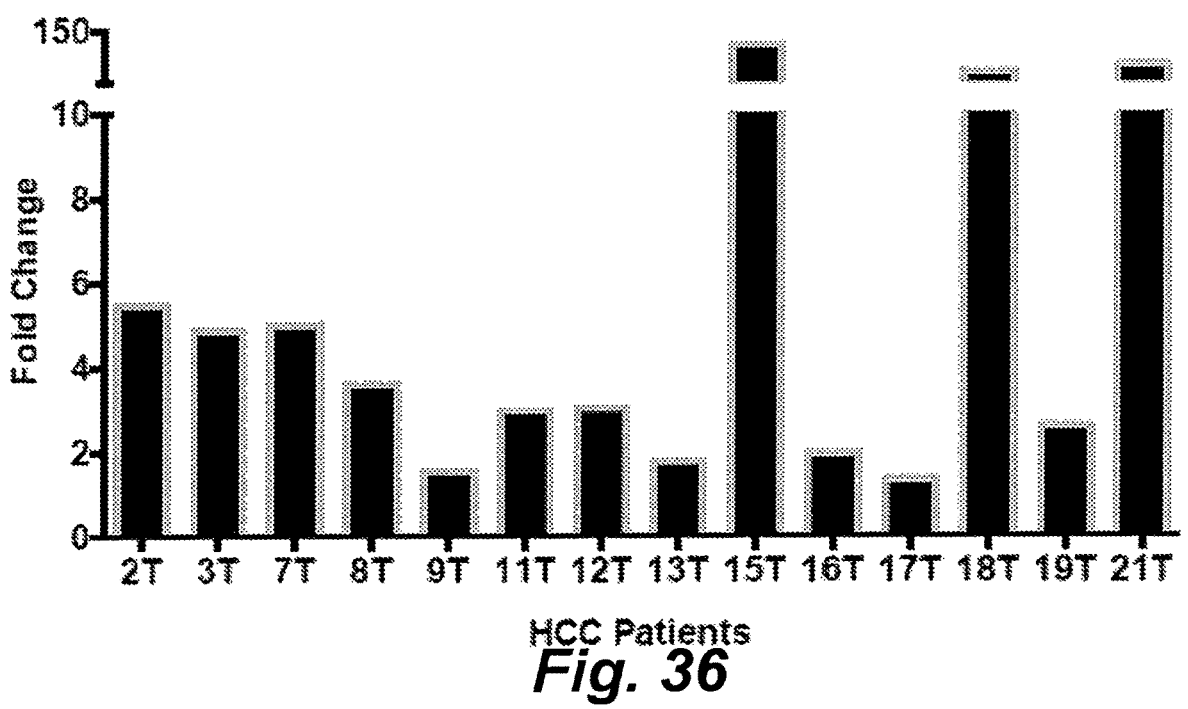
FIG. 36 illustrates the signature gene expression in adult HCC patients-up-regulated genes.
Figure 37:
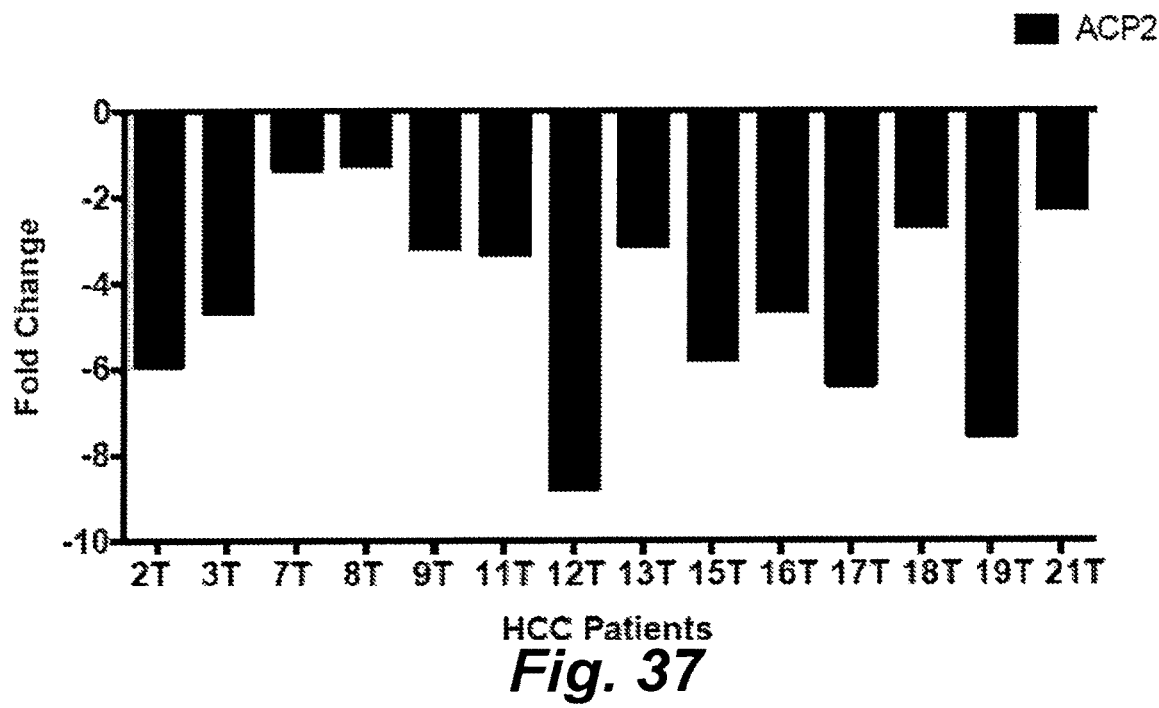
FIG. 37 illustrates the signature gene expression in adult HCC patients-down-regulated genes.
Figure 38:
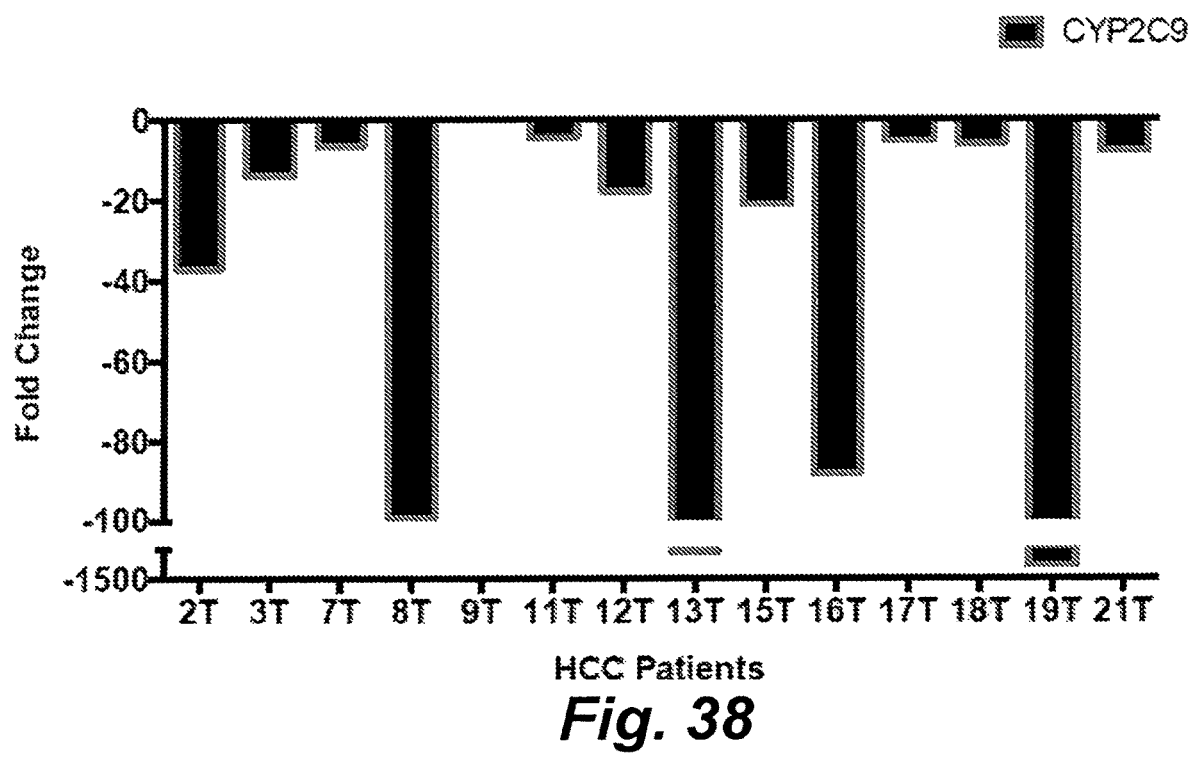
FIG. 38 illustrates the signature gene expression in adult HCC patients-down-regulated genes.

Each of the 12 genes was assigned a score; a positive score indicated that higher expression of the gene is associated with poor survival, whereas a negative score indicated that higher expression of the gene is associated with longer survival (Table 7) and FIGS. 27-29):

TABLE 7

| Gene Name | Score |
|---|---|
| ALDOA | 3.1968 |
| ARID3A | 1.7599 |
| LGALS1 | 1.4320 |
| HBEGF | 0.9818 |
| AFP | 0.7382 |
| SLC35D2 | 0.0627 |
| CYP2C9 | −0.5399 |
| CYP4V2 | −0.7029 |
| LIMK2 | −0.9806 |
| ACP2 | −2.2464 |

TABLE 7-continued

| Gene Name | Score |
|---|---|
| LGALS3 | −2.5003 |
| NDRG1 | −2.8716 |

Example 18

Taqman™ gene expression assays consisted of a pair of unlabeled PCR primers and a Taqman™ probe with a FAM™ or VIV™ dye label attached the 5' end of each probe and a minor groove binder (MBG) nonfluorescent quencher (NFQ) on the 3' end.

RNA from samples of interest was reverse transcribed into cDNA and the synthesized served as the template for real-time PCR.

Primer and probe sequences for each gene are shown in FIG. 30.

Quantitative levels of differential expression of the genes that comprise the genetic signature related to levels of or propensity for metastasis of hepatocellular carcinomas are shown I FIGS. 33-38.

We claim:

1. A method for determining whether a hepatocellular carcinoma tissue of a patient has a differential gene expression signature of a metastatic hepatocellular carcinoma tissue, the method comprising the steps:

(a) obtaining a first gene expression signature from a first tissue sample from a first subject by determining the levels of expression of the genes aldoa, arid3a, lgals1, hbegf, afp, slc35d2, cyp2c9, cyp4v2, limk2, acp2, lgals3, and ndrg1 in the first tissue sample, wherein the first tissue sample is a hepatocellular carcinoma;

(b) obtaining a gene expression signature from a second tissue sample from a second subject by determining the levels of expression of the genes aldoa, arid3a, lgals1, hbegf, afp, slc35d2, cyp2c9, cyp4v2, limk2, acp2, lgals3, and ndrg1 in the second tissue sample, wherein the second tissue sample is from a subject not having an hepatocellular carcinoma or suspected of not having developed a metastatic hepatocellular carcinoma;

wherein step (a) and step (b) each independently consists of the steps:
(i) isolating RNA from the tissue sample and generating cDNA copies therefrom;
(ii) quantitatively measuring the RNA levels expressed by the genes aldoa, arid3a, lgals1, hbegf, afp, slc35d2, cyp2c9, cyp4v2, limk2, acp2, lgals3, and ndrg1 by a Reverse Transcription Polymerase Chain Reaction (RT-PCR) assay, wherein the RT-PCR uses the PCR primer pairs: aldoa-specific SEQ ID NOs: 1 and 2; arid3a-specific SEQ ID NOs: 3 and 4; lgals1-specific SEQ ID NOs: 5 and 6; hbegf-specific SEQ ID NOs: 7 and 8; afp-specific SEQ ID NOs: 9 and 10; slc35d2-specific SEQ ID NOs: 11 and 12; cyp2c9-specific SEQ ID NOs: 13 and 14; cyp4v2-specific SEQ ID NOs: 15 and 16; limk2-specific SEQ ID NOs: 17 and 18; acp2-specific SEQ ID NOs: 19 and 20; lgals3-specific SEQ ID NOs: 21 and 22; and ndrg1-specific SEQ ID NOs: 23 and 24; and further uses the chemically-modified probes: aldoa-specific SEQ ID NO: 25; arid3a-specific SEQ ID NO: 26; lgals1-specific SEQ ID NO: 27; hbegf-specific SEQ ID NO: 28; afp-specific SEQ ID NO: 29; slc35d2-specific SEQ ID NO: 30; cyp2c9-specific SEQ ID NO: 31; cyp4v2-specific SEQ ID NO: 32; limk2-specific SEQ ID NO: 33; acp2-specific SEQ ID NO: 34; lgals3-specific SEQ ID NO: 35; and ndrg1-specific SEQ ID NO: 36, wherein each of the chemically-modified probes has a terminally attached fluorescent moiety and a terminally attached quenching moiety, and wherein the expression level of each gene is quantifiably measured by measuring the intensity of fluorescence from each of said gene-specific chemically-modified probes.

2. The method of claim 1, further comprising the steps of:
(c) comparing the levels of gene expression of the first and the second gene expression signatures, wherein the relative levels of gene expression indicate the presence or absence of metastatic hepatocellular carcinoma cells in the first subject suspected of having a metastatic hepatocellular carcinoma; and
(d) generating a report indicating the metastatic status of a hepatocellular carcinoma of the patient, wherein:
(i) an expression level of the genes aldoa, arid3a, lgals1, hbegf, afp, slc35d2 of the first tissue sample is greater than the expression level of the same genes in the second tissue sample indicates that the first subject has a lower probability of survival than does the second subject not having a metastatic hepatocellular carcinoma; and
(ii) if the expression level of the genes cyp2c9, cyp4v2, limk2, acp2, lgals3, and ndrg1 in the first tissue sample is greater than the expression level of the genes cyp2c9, cyp4v2, limk2, acp2, lgals3, and ndrg1 in the second tissue sample, said levels indicate an extended period of the first subject survival than does the second subject not having a metastatic hepatocellular carcinoma the first subject has a survival period greater than if the expression level of the genes cyp2c9, cyp4v2, limk2, acp2, lgals3, and ndrg1 in the first tissue sample is the same as or lower than the expression level of the genes cyp2c9, cyp4v2, limk2, acp2, lgals3, and ndrg1 in the second tissue sample.

3. The method of claim 1, wherein the first and the second tissue samples are from the same subject and isolated therefrom at successive time-points.

4. The method of claim 1, wherein the terminally attached fluorescent moiety is attached to the 3' terminus of a probe and the terminally attached quenching moiety is attached to the 5' terminus of a probe.

5. The method of claim 1, wherein the terminally attached fluorescent moiety is attached to the 5' terminus of a probe and the terminally attached quenching moiety is attached to the 3' terminus of a probe.

6. The method of claim 1, wherein the products of the RT-PCR steps are hybridized to complimentary nucleotide sequences arrayed on a substrate and detected thereon.

7. A method of determining a mode of treatment of a hepatocellular carcinoma of a patient, comprising:
(a) obtaining a first gene expression signature from a first tissue sample from a first subject by determining the levels of expression of the genes aldoa, arid3a, lgals1, hbegf, afp, slc35d2, cyp2c9, cyp4v2, limk2, acp2, lgals3, and ndrg1 in the first tissue sample, wherein the first tissue sample is a hepatocellular carcinoma;
(b) obtaining a gene expression signature from a second tissue sample from a second subject by determining the levels of expression of the genes aldoa, arid3a, lgals1, hbegf, afp, slc35d2, cyp2c9, cyp4v2, limk2, acp2, lgals3, and ndrg1 in the second tissue sample, wherein the second tissue sample is from a subject not having an hepatocellular carcinoma or suspected of not having developed a metastatic hepatocellular carcinoma;

wherein step (a) and step (b) each independently consists of the steps:
(i) isolating RNA from the tissue sample and generating cDNA copies therefrom;
(ii) quantitatively measuring the RNA levels expressed by the genes aldoa, arid3a, lgals1, hbegf, afp, slc35d2, cyp2c9, cyp4v2, limk2, acp2, lgals3, and ndrg1 by a Reverse Transcription Polymerase Chain Reaction (RT-PCR) assay, wherein the RT-PCR uses the PCR primer pairs: aldoa-specific SEQ ID NOs: 1 and 2; arid3a-specific SEQ ID NOs: 3 and 4; lgals1-specific SEQ ID NOs: 5 and 6; hbegf-specific SEQ ID NOs: 7 and 8; afp-specific SEQ ID NOs: 9 and 10; slc35d2-specific SEQ ID NOs: 11 and 12; cyp2c9-specific SEQ ID NOs: 13 and 14; cyp4v2-specific SEQ ID NOs: 15 and 16; limk2-specific SEQ ID NOs: 17 and 18; acp2-specific SEQ ID NOs: 19 and 20; lgals3-specific SEQ ID NOs: 21 and 22; and ndrg1-specific SEQ ID NOs: 23 and 24; and further uses the chemically-modified probes: aldoa-specific SEQ ID NO: 25; arid3a-specific SEQ ID NO: 26; lgals1-specific SEQ ID NO: 27; hbegf-specific SEQ ID NO: 28; afp-specific SEQ ID NO: 29; slc35d2-specific SEQ ID NO: 30; cyp2c9-specific SEQ ID NO: 31; cyp4v2-specific SEQ ID NO: 32; limk2-specific SEQ ID NO: 33; acp2-specific SEQ ID NO: 34; lgals3-specific SEQ ID NO: 35; and ndrg1-specific SEQ ID NO: 36, wherein each of the chemically-modified probes has a terminally attached fluorescent moiety and a terminally attached quenching moiety, and wherein the expression level of each gene is quantifiably measured by measuring the intensity of fluorescence from each of said gene-specific chemically-modified probes;
(c) comparing the levels of gene expression of the first and the second gene expression signatures, wherein the relative levels of gene expression indicate the presence or absence of metastatic hepatocellular carcinoma cells in the first subject suspected of having a metastatic hepatocellular carcinoma; and (d) generating a report indicating the metastatic status of a hepatocellular carcinoma of the patient, wherein:

(i) an expression level of the genes aldoa, arid3a, lgals1, hbegf, afp, slc35d2 of the first tissue sample is greater than the expression level of the same genes in the second tissue sample indicates that the first subject has a lower probability of survival than does the second subject not having a metastatic hepatocellular carcinoma; and (ii) if the expression level of the genes cyp2c9, cyp4v2, limk2, acp2, lgals3, and ndrg1 in the first tissue sample is greater than the expression level of the genes cyp2c9, cyp4v2, limk2, acp2, lgals3, and ndrg1 in the second tissue sample, the first subject has a survival period greater than if the expression level of the genes cyp2c9, cyp4v2, limk2, acp2, lgals3, and ndrg1 in the first tissue sample is the same as or lower than the expression level of the genes cyp2c9, cyp4v2, limk2, acp2, lgals3, and ndrg1 in the second tissue sample; and (e) adjusting a mode of treatment of a hepatocellular carcinoma of the patient from whom the first tissue sample was obtained.

8. The method of claim 7, wherein the second tissue sample is obtained from a subject not having an hepatocellular carcinoma or suspected of not having developed a metastatic hepatocellular carcinoma.

9. The method of claim 7, wherein the first and the second tissue samples are from the same subject and isolated therefrom at successive time-points, thereby indicating the progression of the hepatocellular carcinoma in the patient.

10. The method of claim 7, wherein the terminally attached fluorescent moiety is attached to the 3' terminus of a probe and the terminally attached quenching moiety is attached to the 5' terminus of a probe.

11. The method of claim 7, wherein the terminally attached fluorescent moiety is attached to the 5' terminus of a probe and the terminally attached quenching moiety is attached to the 3' terminus of a probe.

12. The method of claim 7, wherein the products of the RT-PCR steps are hybridized to complimentary nucleotide sequences arrayed on a substrate and detected thereon.

* * * * *

SEQUENCE LISTING

<160> NUMBER OF SEQ ID NOS: 78

<210> SEQ ID NO 1
<211> LENGTH: 19
<212> TYPE: DNA
<213> ORGANISM: Artificial Sequence
<220> FEATURE:
<223> OTHER INFORMATION: ALDOA Forward Primer

<400> SEQUENCE: 1
aagcgctgcc agtatgtga                                                    19

<210> SEQ ID NO 2
<211> LENGTH: 22
<212> TYPE: DNA
<213> ORGANISM: Artificial Sequence
<220> FEATURE:
<223> OTHER INFORMATION: ALDOA Reverse Primer

<400> SEQUENCE: 2
gtcactcaga gccttgtaga ca                                                22

<210> SEQ ID NO 3
<211> LENGTH: 18
<212> TYPE: DNA
<213> ORGANISM: Artificial Sequence
<220> FEATURE:
<223> OTHER INFORMATION: ARID3A Forward Primer

<400> SEQUENCE: 3
gctgcccatg agcattcg                                                     18

<210> SEQ ID NO 4
<211> LENGTH: 20
<212> TYPE: DNA
<213> ORGANISM: Artificial Sequence
<220> FEATURE:
<223> OTHER INFORMATION: ARID3A Reverse Primer

<400> SEQUENCE: 4
cgtcaggttc acagcagagt                                                   20

<210> SEQ ID NO 5
<211> LENGTH: 20
<212> TYPE: DNA
<213> ORGANISM: Artificial Sequence
<220> FEATURE:
<223> OTHER INFORMATION: LGALS1 Forward Primer

<400> SEQUENCE: 5
gaggctgtct ttcccttcca                                                   20

<210> SEQ ID NO 6
<211> LENGTH: 19
<212> TYPE: DNA
<213> ORGANISM: Artificial Sequence
<220> FEATURE:
<223> OTHER INFORMATION: LGALS1 Reverse Primer

<400> SEQUENCE: 6
gcagcttgac ggtcaggtt                                                    19

<210> SEQ ID NO 7
<211> LENGTH: 27
<212> TYPE: DNA
<213> ORGANISM: Artificial Sequence

```
<220> FEATURE:
<223> OTHER INFORMATION: HBEGF Forward Primer

<400> SEQUENCE: 7
ccatggagaa tgcaaatatg tgaagga                                        27

<210> SEQ ID NO 8
<211> LENGTH: 20
<212> TYPE: DNA
<213> ORGANISM: Artificial Sequence
<220> FEATURE:
<223> OTHER INFORMATION: HBEGF Reverse Primer

<400> SEQUENCE: 8
tcagcccatg acacctctct                                                20

<210> SEQ ID NO 9
<211> LENGTH: 25
<212> TYPE: DNA
<213> ORGANISM: Artificial Sequence
<220> FEATURE:
<223> OTHER INFORMATION: HAFP Forward Primer

<400> SEQUENCE: 9
gccaactcag tgaggacaaa ctatt                                          25

<210> SEQ ID NO 10
<211> LENGTH: 27
<212> TYPE: DNA
<213> ORGANISM: Artificial Sequence
<220> FEATURE:
<223> OTHER INFORMATION: HAFP Reverse Primer

<400> SEQUENCE: 10
ggtttactgg agtcatttca tgtctga                                        27

<210> SEQ ID NO 11
<211> LENGTH: 22
<212> TYPE: DNA
<213> ORGANISM: Artificial Sequence
<220> FEATURE:
<223> OTHER INFORMATION: SLC35D2 Forward Primer

<400> SEQUENCE: 11
tcctcatcgt gcttgtcaac aa                                             22

<210> SEQ ID NO 12
<211> LENGTH: 24
<212> TYPE: DNA
<213> ORGANISM: Artificial Sequence
<220> FEATURE:
<223> OTHER INFORMATION: SLC35D2 Reverse Primer

<400> SEQUENCE: 12
gccatctgtc caattccaag gaaa                                           24

<210> SEQ ID NO 13
<211> LENGTH: 25
<212> TYPE: DNA
<213> ORGANISM: Artificial Sequence
<220> FEATURE:
<223> OTHER INFORMATION: CYP2C9 Forward Primer

<400> SEQUENCE: 13
ccatgcagtg acctgtgaca ttaaa                                          25
```

<210> SEQ ID NO 14
<211> LENGTH: 25
<212> TYPE: DNA
<213> ORGANISM: Artificial Sequence
<220> FEATURE:
<223> OTHER INFORMATION: CYP2C9 Reverse Primer

<400> SEQUENCE: 14
atgtagcaca gaagtcaggg aaatt                                    25

<210> SEQ ID NO 15
<211> LENGTH: 25
<212> TYPE: DNA
<213> ORGANISM: Artificial Sequence
<220> FEATURE:
<223> OTHER INFORMATION: CYP4V2 Forward Primer

<400> SEQUENCE: 15
tgttccttta tttgcccgta gtgtt                                    25

<210> SEQ ID NO 16
<211> LENGTH: 23
<212> TYPE: DNA
<213> ORGANISM: Artificial Sequence
<220> FEATURE:
<223> OTHER INFORMATION: CYP4V2 Reverse Primer

<400> SEQUENCE: 16
cggcttcagt gccttttaga act                                      23

<210> SEQ ID NO 17
<211> LENGTH: 19
<212> TYPE: DNA
<213> ORGANISM: Artificial Sequence
<220> FEATURE:
<223> OTHER INFORMATION: LIMK2 Forward Primer

<400> SEQUENCE: 17
gtgctccctg ctgatgaca                                           19

<210> SEQ ID NO 18
<211> LENGTH: 23
<212> TYPE: DNA
<213> ORGANISM: Artificial Sequence
<220> FEATURE:
<223> OTHER INFORMATION: LIMK2 Reverse Primer

<400> SEQUENCE: 18
cactctgggt ggtacttgaa ctc                                      23

<210> SEQ ID NO 19
<211> LENGTH: 21
<212> TYPE: DNA
<213> ORGANISM: Artificial Sequence
<220> FEATURE:
<223> OTHER INFORMATION: ACP2 Forward Primer

<400> SEQUENCE: 19
ctggagaccg tctggaatgt c                                        21

<210> SEQ ID NO 20
<211> LENGTH: 19
<212> TYPE: DNA
<213> ORGANISM: Artificial Sequence
<220> FEATURE:
<223> OTHER INFORMATION: ACP2 Reverse Primer

```
<400> SEQUENCE: 20
gagacgctgc atggtttgg                                                      19

<210> SEQ ID NO 21
<211> LENGTH: 23
<212> TYPE: DNA
<213> ORGANISM: Artificial Sequence
<220> FEATURE:
<223> OTHER INFORMATION: LGALS3 Forward Primer

<400> SEQUENCE: 21
gcctcgcatg ctgataacaa ttc                                                 23

<210> SEQ ID NO 22
<211> LENGTH: 23
<212> TYPE: DNA
<213> ORGANISM: Artificial Sequence
<220> FEATURE:
<223> OTHER INFORMATION: LGALS3 Reverse Primer

<400> SEQUENCE: 22
ggcaacatca ttccctcttt gga                                                 23

<210> SEQ ID NO 23
<211> LENGTH: 21
<212> TYPE: DNA
<213> ORGANISM: Artificial Sequence
<220> FEATURE:
<223> OTHER INFORMATION: NDRG1 Forward Primer

<400> SEQUENCE: 23
ggacccaaca aagaccactc t                                                   21

<210> SEQ ID NO 24
<211> LENGTH: 17
<212> TYPE: DNA
<213> ORGANISM: Artificial Sequence
<220> FEATURE:
<223> OTHER INFORMATION: NDRG1 Reverse Primer

<400> SEQUENCE: 24
gccggctggg agatctg                                                        17

<210> SEQ ID NO 25
<211> LENGTH: 16
<212> TYPE: DNA
<213> ORGANISM: Artificial Sequence
<220> FEATURE:
<223> OTHER INFORMATION: ALDOA Reporter-probe-quencher construct

<400> SEQUENCE: 25
cagccagcac cttctc                                                         16

<210> SEQ ID NO 26
<211> LENGTH: 16
<212> TYPE: DNA
<213> ORGANISM: Artificial Sequence
<220> FEATURE:
<223> OTHER INFORMATION: ARID3A Reporter-probe-quencher construct

<400> SEQUENCE: 26
ccaagcctcc gaaagc                                                         16

<210> SEQ ID NO 27
```

```
<211> LENGTH: 17
<212> TYPE: DNA
<213> ORGANISM: Artificial Sequence
<220> FEATURE:
<223> OTHER INFORMATION: LGALS1 Reporter-probe-quencher construct

<400> SEQUENCE: 27
cagaggtgtg catcacc                                                    17

<210> SEQ ID NO 28
<211> LENGTH: 16
<212> TYPE: DNA
<213> ORGANISM: Artificial Sequence
<220> FEATURE:
<223> OTHER INFORMATION: HBEGF Reporter-probe-quencher construct

<400> SEQUENCE: 28
cctgcatctg ccaccc                                                     16

<210> SEQ ID NO 29
<211> LENGTH: 16
<212> TYPE: DNA
<213> ORGANISM: Artificial Sequence
<220> FEATURE:
<223> OTHER INFORMATION: HAFP Reporter-probe-quencher construct

<400> SEQUENCE: 29
aatgtcagcc gctccc                                                     16

<210> SEQ ID NO 30
<211> LENGTH: 15
<212> TYPE: DNA
<213> ORGANISM: Artificial Sequence
<220> FEATURE:
<223> OTHER INFORMATION: SLC35D2 Reporter-probe-quencher construct

<400> SEQUENCE: 30
cacctacggt ttccc                                                      15

<210> SEQ ID NO 31
<211> LENGTH: 16
<212> TYPE: DNA
<213> ORGANISM: Artificial Sequence
<220> FEATURE:
<223> OTHER INFORMATION: CYP2C9 Reporter-probe-quencher construct

<400> SEQUENCE: 31
tcccaagggc acaacc                                                     16

<210> SEQ ID NO 32
<211> LENGTH: 19
<212> TYPE: DNA
<213> ORGANISM: Artificial Sequence
<220> FEATURE:
<223> OTHER INFORMATION: CYP4V2 Reporter-probe-quencher construct

<400> SEQUENCE: 32
ctgtaacctg ccacttcac                                                  19

<210> SEQ ID NO 33
<211> LENGTH: 16
<212> TYPE: DNA
<213> ORGANISM: Artificial Sequence
<220> FEATURE:
<223> OTHER INFORMATION: LIMK2 Reporter-probe-quencher construct

<400> SEQUENCE: 33
```

-continued

```
ccagccacca taaaag                                                  16

<210> SEQ ID NO 34
<211> LENGTH: 16
<212> TYPE: DNA
<213> ORGANISM: Artificial Sequence
<220> FEATURE:
<223> OTHER INFORMATION: ACP2 Reporter-probe-quencher construct

<400> SEQUENCE: 34
ccgtgcgttt gctcac                                                  16

<210> SEQ ID NO 35
<211> LENGTH: 17
<212> TYPE: DNA
<213> ORGANISM: Artificial Sequence
<220> FEATURE:
<223> OTHER INFORMATION: LGALS3 Reporter-probe-quencher construct

<400> SEQUENCE: 35
aatgcaaaca gaattgc                                                 17

<210> SEQ ID NO 36
<211> LENGTH: 16
<212> TYPE: DNA
<213> ORGANISM: Artificial Sequence
<220> FEATURE:
<223> OTHER INFORMATION: NDRG1 Reporter-probe-quencher construct

<400> SEQUENCE: 36
acagtccgcc atcttg                                                  16

<210> SEQ ID NO 37
<211> LENGTH: 24
<212> TYPE: DNA
<213> ORGANISM: Artificial Sequence
<220> FEATURE:
<223> OTHER INFORMATION: SCCPDH Forward Primer

<400> SEQUENCE: 37
gcagccatga ctcttctaag tgat                                         24

<210> SEQ ID NO 38
<211> LENGTH: 19
<212> TYPE: DNA
<213> ORGANISM: Artificial Sequence
<220> FEATURE:
<223> OTHER INFORMATION: SCCPDH Reverse Primer

<400> SEQUENCE: 38
agctgctcca ggtgtgaag                                               19

<210> SEQ ID NO 39
<211> LENGTH: 20
<212> TYPE: DNA
<213> ORGANISM: Artificial Sequence
<220> FEATURE:
<223> OTHER INFORMATION: KIFC1 Forward Primer

<400> SEQUENCE: 39
agaagccagt tcctgctgtt                                              20

<210> SEQ ID NO 40
<211> LENGTH: 19
<212> TYPE: DNA
```

```
<213> ORGANISM: Artificial Sequence
<220> FEATURE:
<223> OTHER INFORMATION: KIFC1 Reverse Primer

<400> SEQUENCE: 40
cctgccatgg gaggaacac                                              19

<210> SEQ ID NO 41
<211> LENGTH: 18
<212> TYPE: DNA
<213> ORGANISM: Artificial Sequence
<220> FEATURE:
<223> OTHER INFORMATION: HMYC Forward Primer

<400> SEQUENCE: 41
cccctggtgc tccatgag                                               18

<210> SEQ ID NO 42
<211> LENGTH: 26
<212> TYPE: DNA
<213> ORGANISM: Artificial Sequence
<220> FEATURE:
<223> OTHER INFORMATION: HMYC Reverse Primer

<400> SEQUENCE: 42
cctcttttcc acagaaacaa catcga                                      26

<210> SEQ ID NO 43
<211> LENGTH: 25
<212> TYPE: DNA
<213> ORGANISM: Artificial Sequence
<220> FEATURE:
<223> OTHER INFORMATION: HLPL Forward Primer

<400> SEQUENCE: 43
gcacaccaag ataccattca tcaac                                       25

<210> SEQ ID NO 44
<211> LENGTH: 22
<212> TYPE: DNA
<213> ORGANISM: Artificial Sequence
<220> FEATURE:
<223> OTHER INFORMATION: HLPL Reverse Primer

<400> SEQUENCE: 44
ggtagaggat tgccgctatg ag                                          22

<210> SEQ ID NO 45
<211> LENGTH: 25
<212> TYPE: DNA
<213> ORGANISM: Artificial Sequence
<220> FEATURE:
<223> OTHER INFORMATION: IQGAP1 Forward Primer

<400> SEQUENCE: 45
cccaaagaac aaataccagg aactg                                       25

<210> SEQ ID NO 46
<211> LENGTH: 19
<212> TYPE: DNA
<213> ORGANISM: Artificial Sequence
<220> FEATURE:
<223> OTHER INFORMATION: IQGAP1 Reverse Primer

<400> SEQUENCE: 46
cggtacctcc gctgattcc                                              19
```

<210> SEQ ID NO 47
<211> LENGTH: 24
<212> TYPE: DNA
<213> ORGANISM: Artificial Sequence
<220> FEATURE:
<223> OTHER INFORMATION: TBC1D1 Forward Primer

<400> SEQUENCE: 47
cagcagcatg cgattcttat tgac            24

<210> SEQ ID NO 48
<211> LENGTH: 23
<212> TYPE: DNA
<213> ORGANISM: Artificial Sequence
<220> FEATURE:
<223> OTHER INFORMATION: TBC1D1 Reverse Primer

<400> SEQUENCE: 48
ggcagagaag tatgggtgtg tag             23

<210> SEQ ID NO 49
<211> LENGTH: 17
<212> TYPE: DNA
<213> ORGANISM: Artificial Sequence
<220> FEATURE:
<223> OTHER INFORMATION: TWIST1 Forward Primer

<400> SEQUENCE: 49
agcgcggcaa gaagtct                    17

<210> SEQ ID NO 50
<211> LENGTH: 17
<212> TYPE: DNA
<213> ORGANISM: Artificial Sequence
<220> FEATURE:
<223> OTHER INFORMATION: TWIST Reverse Primer

<400> SEQUENCE: 50
cgcacgttgg ccatgac                    17

<210> SEQ ID NO 51
<211> LENGTH: 16
<212> TYPE: DNA
<213> ORGANISM: Artificial Sequence
<220> FEATURE:
<223> OTHER INFORMATION: UAP1L1 Forward Primer

<400> SEQUENCE: 51
cagcgacccc gagaca                     16

<210> SEQ ID NO 52
<211> LENGTH: 21
<212> TYPE: DNA
<213> ORGANISM: Artificial Sequence
<220> FEATURE:
<223> OTHER INFORMATION: UAP1L1 Reverse Primer

<400> SEQUENCE: 52
cggccacctt gttcagagaa a               21

<210> SEQ ID NO 53
<211> LENGTH: 15
<212> TYPE: DNA
<213> ORGANISM: Artificial Sequence
<220> FEATURE:

<223> OTHER INFORMATION: ENO2 Forward Primer

<400> SEQUENCE: 53
cgcgccagcc ctcat                                                     15

<210> SEQ ID NO 54
<211> LENGTH: 23
<212> TYPE: DNA
<213> ORGANISM: Artificial Sequence
<220> FEATURE:
<223> OTHER INFORMATION: ENO2 Reverse Primer

<400> SEQUENCE: 54
caggttgtcc agtttctctt gct                                            23

<210> SEQ ID NO 55
<211> LENGTH: 18
<212> TYPE: DNA
<213> ORGANISM: Artificial Sequence
<220> FEATURE:
<223> OTHER INFORMATION: MAP3K6 Forward Primer

<400> SEQUENCE: 55
gctgcccatg agcattcg                                                  18

<210> SEQ ID NO 56
<211> LENGTH: 20
<212> TYPE: DNA
<213> ORGANISM: Artificial Sequence
<220> FEATURE:
<223> OTHER INFORMATION: MAP3K6 Reverse Primer

<400> SEQUENCE: 56
cgtcaggttc acagcagagt                                                20

<210> SEQ ID NO 57
<211> LENGTH: 25
<212> TYPE: DNA
<213> ORGANISM: Artificial Sequence
<220> FEATURE:
<223> OTHER INFORMATION: PLP2 Forward Primer

<400> SEQUENCE: 57
gcacaccaag ataccattca tcaac                                          25

<210> SEQ ID NO 58
<211> LENGTH: 22
<212> TYPE: DNA
<213> ORGANISM: Artificial Sequence
<220> FEATURE:
<223> OTHER INFORMATION: PLP2 Reverse Primer

<400> SEQUENCE: 58
ggtagaggat tgccgctatg ag                                             22

<210> SEQ ID NO 59
<211> LENGTH: 22
<212> TYPE: DNA
<213> ORGANISM: Artificial Sequence
<220> FEATURE:
<223> OTHER INFORMATION: PYGB Forward Primer

<400> SEQUENCE: 59
tggagaacta ccgtgtgtcc tt                                             22

```
<210> SEQ ID NO 60
<211> LENGTH: 19
<212> TYPE: DNA
<213> ORGANISM: Artificial Sequence
<220> FEATURE:
<223> OTHER INFORMATION: PYGB Reverse Primer

<400> SEQUENCE: 60
tgcctgcagt ggagatctg                                                 19

<210> SEQ ID NO 61
<211> LENGTH: 24
<212> TYPE: DNA
<213> ORGANISM: Artificial Sequence
<220> FEATURE:
<223> OTHER INFORMATION: HUBC Forwrad Primer

<400> SEQUENCE: 61
aaggcaaaga tccaagacaa ggaa                                           24

<210> SEQ ID NO 62
<211> LENGTH: 22
<212> TYPE: DNA
<213> ORGANISM: Artificial Sequence
<220> FEATURE:
<223> OTHER INFORMATION: HUBC Reverse Primer

<400> SEQUENCE: 62
cagctgtttt ccggcaaaga tc                                             22

<210> SEQ ID NO 63
<211> LENGTH: 25
<212> TYPE: DNA
<213> ORGANISM: Artificial Sequence
<220> FEATURE:
<223> OTHER INFORMATION: CORO1C Forward Primer

<400> SEQUENCE: 63
tgttccttta tttgcccgta gtgtt                                          25

<210> SEQ ID NO 64
<211> LENGTH: 23
<212> TYPE: DNA
<213> ORGANISM: Artificial Sequence
<220> FEATURE:
<223> OTHER INFORMATION: CORO1C Reverse Primer

<400> SEQUENCE: 64
cggcttcagt gcctttttaga act                                           23

<210> SEQ ID NO 65
<211> LENGTH: 14
<212> TYPE: DNA
<213> ORGANISM: Artificial Sequence
<220> FEATURE:
<223> OTHER INFORMATION: SCCPDH Reporter-probe-quencher construct

<400> SEQUENCE: 65
ccccgcccgc ctta                                                      14

<210> SEQ ID NO 66
<211> LENGTH: 17
<212> TYPE: DNA
<213> ORGANISM: Artificial Sequence
<220> FEATURE:
<223> OTHER INFORMATION: KIFC1 Reporter-probe-quencher construct
```

<400> SEQUENCE: 66
ctgatgtgcc agacttc                                                    17

<210> SEQ ID NO 67
<211> LENGTH: 17
<212> TYPE: DNA
<213> ORGANISM: Artificial Sequence
<220> FEATURE:
<223> OTHER INFORMATION: HMYC Reporter-probe-quencher construct

<400> SEQUENCE: 67
cctcctcaga gtcgctg                                                    17

<210> SEQ ID NO 68
<211> LENGTH: 15
<212> TYPE: DNA
<213> ORGANISM: Artificial Sequence
<220> FEATURE:
<223> OTHER INFORMATION: HLPL Reporter-probe-quencher construct

<400> SEQUENCE: 68
ccctggagtg atttc                                                      15

<210> SEQ ID NO 69
<211> LENGTH: 16
<212> TYPE: DNA
<213> ORGANISM: Artificial Sequence
<220> FEATURE:
<223> OTHER INFORMATION: IQGAP1 Reporter-probe-quencher construct

<400> SEQUENCE: 69
attgccaggg atattc                                                     16

<210> SEQ ID NO 70
<211> LENGTH: 16
<212> TYPE: DNA
<213> ORGANISM: Artificial Sequence
<220> FEATURE:
<223> OTHER INFORMATION: TBC1D1 Reporter-probe-quencher construct

<400> SEQUENCE: 70
cttgggcgaa cctttc                                                     16

<210> SEQ ID NO 71
<211> LENGTH: 18
<212> TYPE: DNA
<213> ORGANISM: Artificial Sequence
<220> FEATURE:
<223> OTHER INFORMATION: TWIST1 Reporter-probe-quencher construct

<400> SEQUENCE: 71
cagctcctcg taagactg                                                   18

<210> SEQ ID NO 72
<211> LENGTH: 16
<212> TYPE: DNA
<213> ORGANISM: Artificial Sequence
<220> FEATURE:
<223> OTHER INFORMATION: UAP1L1 Reporter-probe-quencher construct

<400> SEQUENCE: 72
tctgacggaa accttc                                                     16

<210> SEQ ID NO 73
<211> LENGTH: 17

```
<212> TYPE: DNA
<213> ORGANISM: Artificial Sequence
<220> FEATURE:
<223> OTHER INFORMATION: ENO2 Reporter-probe-quencher construct

<400> SEQUENCE: 73
cagctcaggt ctctctg                                                  17

<210> SEQ ID NO 74
<211> LENGTH: 16
<212> TYPE: DNA
<213> ORGANISM: Artificial Sequence
<220> FEATURE:
<223> OTHER INFORMATION: MAP3K6 Reporter-probe-quencher construct

<400> SEQUENCE: 74
ccaagcctcc gaaagc                                                   16

<210> SEQ ID NO 75
<211> LENGTH: 15
<212> TYPE: DNA
<213> ORGANISM: Artificial Sequence
<220> FEATURE:
<223> OTHER INFORMATION: PLP2 Reporter-probe-quencher construct

<400> SEQUENCE: 75
ccctggagtg atttc                                                    15

<210> SEQ ID NO 76
<211> LENGTH: 16
<212> TYPE: DNA
<213> ORGANISM: Artificial Sequence
<220> FEATURE:
<223> OTHER INFORMATION: PYGB Reporter-probe-quencher construct

<400> SEQUENCE: 76
ccgggatcac tttctc                                                   16

<210> SEQ ID NO 77
<211> LENGTH: 16
<212> TYPE: DNA
<213> ORGANISM: Artificial Sequence
<220> FEATURE:
<223> OTHER INFORMATION: HUBC Reporter-probe-quencher construct

<400> SEQUENCE: 77
ctgaccagca gaggtt                                                   16

<210> SEQ ID NO 78
<211> LENGTH: 19
<212> TYPE: DNA
<213> ORGANISM: Artificial Sequence
<220> FEATURE:
<223> OTHER INFORMATION: CORO1C Reporter-probe-quencher construct

<400> SEQUENCE: 78
ctgtaacctg ccacttcac                                                19
```